(12) United States Patent
Nienhouse

(10) Patent No.: US 11,200,304 B2
(45) Date of Patent: Dec. 14, 2021

(54) SYSTEM AND METHOD FOR LOCATING AND DETERMINING SUBSTANCE USE

(71) Applicant: Robert F. Nienhouse 1997 Declaration of Trust, Hinsdale, IL (US)

(72) Inventor: Robert Frank Nienhouse, Hinsdale, IL (US)

(73) Assignee: Robert F. Nienhouse 1997 Declaration of Trust, Hinsdale, IL (US)

( * ) Notice: Subject to any disclaimer, the term of this patent is extended or adjusted under 35 U.S.C. 154(b) by 0 days.

(21) Appl. No.: 16/379,572

(22) Filed: Apr. 9, 2019

(65) Prior Publication Data

US 2019/0311101 A1    Oct. 10, 2019

Related U.S. Application Data

(60) Provisional application No. 62/655,034, filed on Apr. 9, 2018.

(51) Int. Cl.

| | |
|---|---|
| *G06F 21/32* | (2013.01) |
| *H04W 64/00* | (2009.01) |
| *H04N 5/232* | (2006.01) |
| *G06K 9/00* | (2006.01) |
| *G01N 33/497* | (2006.01) |
| *A61B 5/1171* | (2016.01) |
| *A61B 10/00* | (2006.01) |

(52) U.S. Cl.
CPC ............ *G06F 21/32* (2013.01); *A61B 5/1176* (2013.01); *A61B 10/00* (2013.01); *G01N 33/4972* (2013.01); *G06K 9/00288* (2013.01); *G06K 9/00912* (2013.01); *H04N 5/23219* (2013.01); *H04N 5/23222* (2013.01); *H04W 64/00* (2013.01); *A61B 2010/0009* (2013.01); *A61B 2010/0087* (2013.01); *G06K 2009/00939* (2013.01)

(58) Field of Classification Search
None
See application file for complete search history.

(56) References Cited

U.S. PATENT DOCUMENTS

| | | | |
|---|---|---|---|
| 3,437,449 | A | 4/1969 | Luckey |
| 4,843,377 | A | 6/1989 | Fuller |
| 6,229,908 | B1 | 5/2001 | Edmonds |
| 6,748,792 | B1 | 6/2004 | Freund |

(Continued)

OTHER PUBLICATIONS

"Electronic Monitoring System, MEMS 3000 Home station Installation Guide," Elmo Tech Ltd., Mar. 2006.

(Continued)

*Primary Examiner* — Christopher G Findley
(74) *Attorney, Agent, or Firm* — Lathrop GPM LLP

(57) ABSTRACT

In devices that determine levels of substance use, a substance level in a test sample provided to the testing device by a test subject is determined. A sequence of images are captured to include a portion of the face of the test subject providing the test sample and a display of the testing device. A value indicative of the substance level detected within the test sample is determined. A validity indicator indicating validity of the value indicative of the substance level is determined. A current location is determined. The value indicative of the substance level, the validity indicator, and the current location are sent to a remote server.

20 Claims, 23 Drawing Sheets

(56) References Cited

U.S. PATENT DOCUMENTS

| | | |
|---|---|---|
| 8,060,308 B2 | 11/2011 | Breed |
| 8,280,436 B2 | 10/2012 | Harris, Jr. |
| 2002/0127145 A1 | 9/2002 | Der Ghazarian |
| 2003/0093187 A1 | 5/2003 | Walker |
| 2004/0023951 A1 | 12/2004 | Karsten |
| 2006/0202838 A1 | 9/2006 | Hawthorne |
| 2009/0201138 A1 | 8/2009 | Der Ghazarian |
| 2009/0293589 A1 | 12/2009 | Freund |
| 2010/0012417 A1 | 1/2010 | Walter |
| 2010/0136903 A1 | 6/2010 | Lee et al. |
| 2010/0138166 A1 | 6/2010 | Do |
| 2010/0316261 A1 | 12/2010 | Sugimura et al. |
| 2011/0309932 A1 | 12/2011 | Arringdale |
| 2012/0031166 A1 | 2/2012 | Lopez |
| 2013/0021153 A1 | 1/2013 | Keays |
| 2013/0035602 A1* | 2/2013 | Gemer .................. A61B 5/332 600/484 |
| 2013/0070043 A1 | 3/2013 | Geva |
| 2013/0212655 A1 | 8/2013 | Hoyos et al. |
| 2015/0212063 A1* | 7/2015 | Wojcik ............... G06K 9/00261 340/576 |
| 2018/0306776 A1* | 10/2018 | Cado .................. G01N 33/4972 |

OTHER PUBLICATIONS

CNET Reviews, "iBreath: the iPhone Breathalyzer," Dec. 15, 2008.
"MEMS 3000 Cellular Receiver and Transmitter Installation Guide," Elmo Tech, Ltd., 2002-2008.
U.S. Appl. No. 15/393,911; Non-Final Rejection dated Nov. 16, 2017; 47 pgs.

* cited by examiner

500

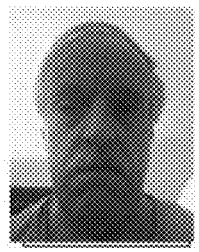

Richard Smith
2937 Main Street
Anywhere, IL 60517
5/10/1947
Male
5' 11"
205
Brown
Gray NOVEMBER 2011
1 2 3 4 5
6 7 8 9 10 11 12
13 14 15 16 17 18 19
20 21 22 23 24 25 26
27 28 29 30

Client Report Detail
12/03/2012 - 01/03/2013

Other Court
INFO here
TBD

Activity:

Thursday, January 3, 2013 Location: 37 23.516 -122 02.625
11:30 AM CST   BAC scheduled
12:00 PM CST   Reminder sent SMS 630-430-2000
12:15 PM CST   Late reminder sent SMS 630-430-2000
12:30 PM CST   Missed Report email alert sent to Robert Smith at r.smith@cam-sys.net Wednesday, January 2, 2013 Location: 37 23.516 -122 02.625
11:30 AM CST   BAC scheduled
12:00 PM CST   Reminder sent SMS 630-430-2000
12:15 PM CST   Late reminder sent SMS 630-430-2000
12:30 PM CST   Missed Report email alert sent to Robert Smith at r.smith@cam-sys.net Tuesday, January 1, 2013 Location: 37 23.516 -122 02.625
11:30 AM CST   BAC scheduled
12:00 PM CST   Reminder sent SMS 630-430-2000
12:15 PM CST   Late reminder sent SMS 630-430-2000
12:30 PM CST   Missed Report email alert sent to Robert Smith at r.smith@cam-sys.net Tuesday, January 1, 2013 Location: 37 23.516 -142 02.625
11:30 AM CST   BAC scheduled
12:00 PM CST   Reminder sent SMS 630-430-2000
12:15 PM CST   Late reminder sent SMS 630-430-2000
12:30 PM CST   Missed Report email alert sent to Robert Smith at r.smith@cam-sys.net Tuesday, January 1, 2013 Location: 37 23.516 -300 02.625
1:30 PM CST   BAC scheduled
2:00 PM CST   Reminder sent SMS 630-430-2000
2:15 PM CST   Late reminder sent SMS 630-430-2000
2:16 PM CST   BAC Sample taken reading: .01
2:17 PM CST   BAC Reported to CAM system @ cam-sys.net

*FIG. 5*

SYSTEM AND METHOD FOR LOCATING AND DETERMINING SUBSTANCE USE

RELATED APPLICATION

This application claims priority to U.S. Provisional Patent Application No. 62/655,034, filed Apr. 9, 2018, and incorporated herein by reference.

FIELD OF THE INVENTION

The present invention concerns measuring various levels of substance use, a location, and vital signs. The drugs may be controlled substances, like alcohol or uncontrolled substances like heroin or marijuana. These measurements are taken and communicated to monitoring authorities and/or interested parties.

BACKGROUND

Prison systems are overcrowded with abusers of alcohol and various drugs. These offenders are in prison to control and monitor their abuse of alcohol and various drugs. Current methods of determining alcohol use include breathalyzer units of various types, some that use electronic testing of blood alcohol levels (BAC) and some that use fuel cell technology to determine blood alcohol levels. Other methods may also be used to determine levels of drug use, for example urine testing.

SUMMARY

Remote monitoring of drug use by these offenders (also known as "users") of either controlled or uncontrolled substances reduces the cost of housing the offenders in the prison system or in a hospital. By providing systems and methods that securely monitor offender drug use at determined remote locations, the need to keep certain of these offenders within the prison systems may be removed, thereby reducing cost. To maintain security of the remote monitoring, the testing device is made foolproof such that collected evidence cannot be faked or altered.

When a patient is in hospital, vital conditions of the patient may be monitored remotely at nurse's stations using one or more sensing devices. Similarly, the systems and methods disclosed herein may also be used to monitor health conditions such that a stay in hospital is avoided, such as where monitoring of a condition by a health professional is needed. The sensors and devices employed may interface to a Smart Phone or the Internet. The invention further provides an ability to monitor offenders' or patients' vitals or drug levels with their location, since it is also important to know the location of the offender or patient at various intervals or at all times. Certain location devices have waterproof ankle bracelets that are not removable without a signal being sent to the group monitoring these individuals by various methods.

The invention may also just be used to locate an individual for court, commercial, and/or personal use. Prisons also may be depopulated when the offender's location is controlled in the community through monitoring. Monitoring of vitals in real time regardless of location is useful to the health care industry and to others.

In accordance with one aspect of the present invention, a method is provided for locating and determining substance use by a test subject. The method involves sensing a level of the substance within a test sample provided by the test subject, communicating the level and a unique serial number of the testing device to a communication device, determining a location of the test subject, and the sending the level, the location, and the unique serial number from the communication device to a remote server. In this manner, both the substance level and location of a patient, offender, or other individual can be verifiably monitored.

The method may involve monitoring the substance for a controlled or uncontrolled substance. For example, the method may involve providing a breathalyzer to monitor a level of alcohol or marijuana. The location of the test subject is preferably determined at a communication device. In this regard, the communication device may determine location, for example, based on GPS information or a network-based technology such as cell, cell sector, time difference of arrival determinations, angle of arrival determinations, or combinations thereof.

Additional information may be sent from the communication device to the remote server. For example, the communication device may acquire and send biometric information concerning the test subject, security code information identifying the specific test at issue or a photograph including a display of the unique serial number, security code, or the like that can be matched to a digital transmission of the same information. The biometric information may include, for example, an image of at least a portion of the subject's face for facial recognition analysis, an image of the patient's iris, fingerprint information, or the like.

In accordance with another aspect of the present invention, a testing device is provided for determining a substance level within a test subject. The testing device comprises a sensor capable of sensing a substance level within a test sample provided by the test subject, a display capable of displaying visual representation of the substance, and an interface capable of communicating the substance level to a communication device or a vehicle module. For example, the communication device may communicate the information to a remote server for monitoring purposes. The vehicle module may be operative to selectively enable or disable operation of the vehicle depending on the substance level.

In one embodiment, the testing device is designed so that it is compact for storage in a pocket or similar compartment and allows for acquiring image information as may be desired. Such image information may be patient's face, an iris, a display including serial number, security code information, or other image that may be used test verification or some other purpose. In this regard, the testing device may include a housing that is movable between extended and collapsed configurations. In the extended configuration the coupling mechanism positions a camera of the communication device for acquiring an image of a face of the test subject. The camera is preferably positioned at least five inches and, in one implementation, about seven inches from the patient's face. For example, the housing may be hinged such that it flips open or closed to define the extended and retracted configurations.

In accordance with a still further aspect of the present invention, a testing device is provided including a display. More specifically, the testing device includes a sensor capable of sensing a substance level within a test sample provided by a test subject; a display capable of displaying a visual representation of test information including at least one of the substance level, a testing device identification, a test identification, and biometric information for the test subject; and an interface capable of communicating the test information to a communication device or a vehicle module.

In one implementation, the visual representation of the test information is compared to a digital version of the same information for test verification. In other implementations, the test information is compared to stored information for verification or other purposes.

In accordance with a still further aspect of the present invention, a method is provided for operating a communication device in connection with monitoring substance use. The method includes: obtaining, at the communication device, a level of the substance within a test sample provided by a subject; operating the communication device to obtain test verification information correlated to the test sample; and sending the level and the test verification information from the communication device to a remote server. For example, the test verification information may include one or more of an identification of the testing device, an identification of a test by which the test sample is provided, and biometric information obtained using the communication device. Additionally or alternatively, the test verification information may include a picture of a display of the testing device.

In accordance with another aspect of the present invention, a collapsible testing device is provided for determining a substance in a test subject. The testing device includes a sensor capable of sensing a substance level within a test sample provided by the test subject; an interface capable of communicating the substance level to one of a communication device and a vehicle module; and a coupling mechanism for physically coupling the communication device to the testing device. The testing device includes a housing that is movable between extended and collapsed configurations wherein, in the extended configuration, the coupling mechanism positions a camera of the communication device for acquiring an image of one or more of a face of the test subject and a display of the testing device. In this manner, the testing device can be moved to the collapsed configuration for compact storage and extended the extended configuration for acquiring images that may be used, for example, for test verification.

In one embodiment, a software product has instructions, stored on non-transitory computer-readable media, that when executed by a digital processor of a communication device, perform steps for controlling a testing device to determine a substance level in a test sample provided to the testing device by a test subject. The communication device generates a prompt for the test subject to provide the test sample to the testing device. The communication device captures, using a camera of the communication device, a sequence of images that include the test subject providing the test sample to the testing device. The camera is positioned by a physical positioning mechanism of the testing device to include a portion of the face of the test subject providing the test sample and a display of the testing device. The communication device receives, from the test device, a value indicative of the substance level detected within the test sample. A validity indicator indicative of validity of the value indicative of the substance level is determined. The communication device determines a current location and sends the value indicative of the substance level, the validity indicator, and the current location to a remote server.

In another embodiment, a method detects fraudulent use of a testing device that measures a substance level within a test sample provided by a test subject. A camera physically positioned to have a field of view of at least part of a face of the test subject providing the test sample captures an image sequence of the test subject providing the test sample. From detected differences between images of the image sequence, a liveness probability for the portion of the face in the image sequence is determined and sent together with the level of the substance within the test sample to a remote server.

In another embodiment, a mouthpiece couples with a testing device of the type that measures a substance level contained in a breath sample provided by a test subject through the mouthpiece. The mouthpiece includes a flange having a substantially oval outer shape and forming a substantially round inner passage through the flange having a first inner surface and a first plurality of first protrusions formed on the first inner surface such that the first inner surface is irregularly shaped and not smooth. The plurality of first protrusions preventing a tube from sealing with the first inner surfaces such that pressure of a sample provided through the tube does not reach sufficient pressure to trigger the testing device.

In another embodiment, a testing device detects a substance level within a test sample provided by a test subject. The testing device includes at least one sensor for detecting the substance level within the test sample, a camera positioned to have a field of view that includes the test subject providing the test sample to the testing device, a location device for determining a current location of the testing device, a processor communicatively coupled with the at least one sensor and the camera, and a memory communicatively coupled with the processor. The memory stores machine readable instructions that when executed by the processor perform the steps of: capturing, using the camera, a sequence of images that include the test subject providing the test sample to the testing device; determining, based upon the at least one sensor, a value indicative of the substance level detected within the test sample; determining, using the location device, a current location of the testing device; determining, based upon the sequence of images, a validity indicator indicative of validity of one or both of an identity of the test subject and a liveness of the test subject; and sending, to a remote server, the value indicative of the substance level, the current location, and the validity indicator.

In another embodiment, a software product has instructions, stored on non-transitory computer-readable media, that, when executed by a digital processor of a communication device, perform steps for controlling a testing device separate and distinct from the communication device to determine a substance level in a test sample provided to the testing device by a test subject, the stored instructions comprising instructions for: generating, from the communication device, a prompt for the test subject to provide the test sample to the testing device, capturing, using a camera of the communication device, a sequence of images that include the test subject providing the test sample to the testing device, the camera being positioned by a physical positioning mechanism of the testing device to include a portion of a face of the test subject providing the test sample and a display of the testing device, detecting a position of the face within a field of view of the camera, instructing the test subject to reposition the camera when the position indicates that the image may be unsuitable for authenticating an identity of the test subject, receiving, within the communication device and from the testing device, a value indicative of the substance level detected within the test sample, determining a validity indicator defining validity of the value indicative of the substance level, determining, within the communication device, a current location, and sending, from the communication device, the value indicative of the substance level, the validity indicator, and the current location to a remote server.

In another embodiment, a method detects fraudulent use of a testing device that measures a substance level within a test sample provided by a test subject. A camera, physically positioned to have a field of view of at least part of a face of the test subject providing the test sample, captures an image sequence of the test subject providing the test sample. A position of the face within a field of view of the camera is determined and the test subject is instructed to reposition the camera when the position indicates that the image may be unsuitable for authenticating an identity of the test subject. A liveness probability for the portion of the face in the image sequence is determined from detected differences between images of the image sequence. The liveness probability together with the level of the substance within the test sample is sent to a remote server.

In another embodiment, a testing device detects a substance level within a test sample provided by a test subject. The testing device includes at least one sensor for detecting the substance level within the test sample, a camera positioned to have a field of view that includes the test subject providing the test sample to the testing device, a location device for determining a current location of the testing device, a processor communicatively coupled with the at least one sensor and the camera, and a memory communicatively coupled with the processor. The memory stores machine readable instructions that when executed by the processor perform the steps of: detecting a position of a face within the field of view of the camera, instructing the test subject to reposition the testing device when the position indicates that images captured by the camera may be unsuitable for authenticating an identity of the test subject, capturing, using the camera, a sequence of images that include the test subject providing the test sample to the testing device, determining, based upon the at least one sensor, a value indicative of the substance level detected within the test sample, determining, using the location device, a current location of the testing device, determining, based upon the sequence of images, a validity indicator indicative of validity of one or both of an identity of the test subject and a liveness of the test subject, and sending, to a remote server, the value indicative of the substance level, the current location, and the validity indicator.

BRIEF DESCRIPTION OF THE FIGURES

FIG. 5 shows one exemplary BAC web application report generated by the web application of the server of FIG. 1.

DETAILED DESCRIPTION

An example of a blood alcohol monitoring and tracking system and method is shown in FIGS. 1 through 7 as an embodiment of the invention. Other substances may be monitored without departing from the scope hereof.

Figure 1:
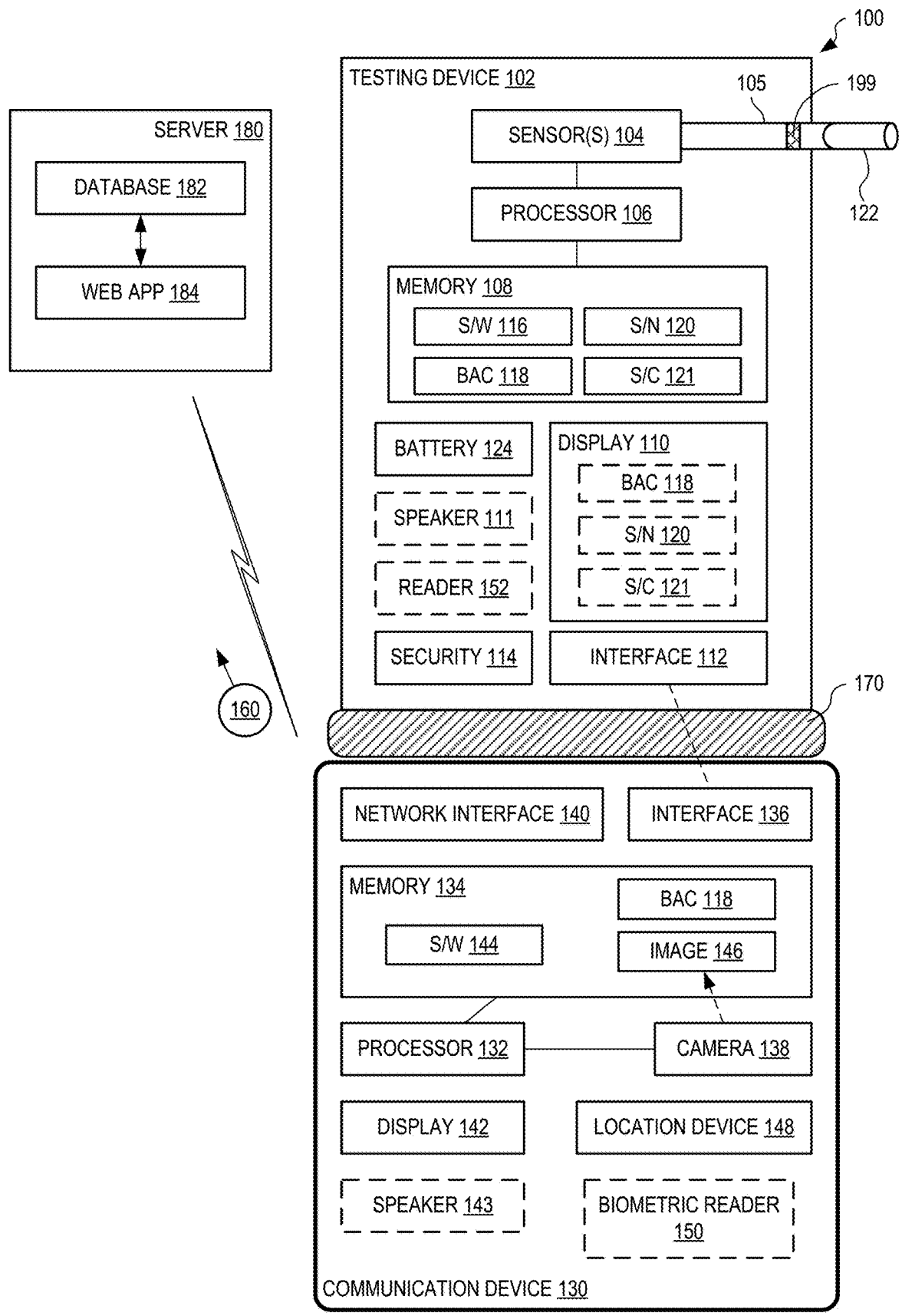
FIG. 1 shows one exemplary system for locating and determining substance use, in an embodiment.

FIG. 1 specifically shows one exemplary system 100 for locating and determining use of controlled and uncontrolled substances by a test subject. System 100 includes a testing device 102 that automatically senses a condition of the test subject. Testing device 102 includes one or more sensors 104, a processor 106, a memory 108, a display 110, a secure interface 112, and a battery 124. Optionally, testing device 102 includes a security unit 114 for monitoring integrity of testing device 102 and indicating whether testing device 102 has been compromised (e.g., opened and/or tampered with). Battery 124 is selected to be of a common type with a long life and that is easily replaceable. The battery may be rechargeable and the system 100 may include an appropriate recharging port. Calibration of testing device 102 is quick and simple.

In one embodiment, sensor 104 detects Breath Alcohol Concentration (BAC) and is for example implemented using fuel cell technology. Testing device 102 thus operates as a Breathalyzer and includes a tube 105 that is coupled with sensor 104 and a distal portion 122 coupled with tube 105 and into which the test subject blows. Base portion of tube 105 is permanently coupled with testing device 102 to prevent tampering and a distal portion 122 is replaceable.

Tube 105 may be configured with sensor protection device 199, such as a cross-hair or mesh, to prevent the test subject from tampering with sensor(s) 104. For example, the cross-hair and/or mesh prevents the test subject from inserting a foreign object into tube 105 in an attempt to damage sensor(s) 104.

Testing device 102 includes software 116, stored within memory 108, having machine readable instructions that when executed by processor 106 control sensor 104 to measure BAC value 118. BAC value 118 is stored in memory 108 and optionally displayed on display 110, as illustratively shown in dashed outline. Software 116 may also include instructions for operating testing device 102 that are displayed on display 110. Security unit 114 may include a serial number 120 (shown stored within memory 108) and an integrity indication (e.g., from security unit 114) that are also displayed on display 110 to indicate authenticity of the measured BAC value 118.

Testing device 102 also includes an interface 112 that couples with a mobile communication device 130. Communication device 130 represents any device that incorporates wireless (e.g., cellular, Wi-Fi) communication, and one or more of processing capability, interface capability, location capability, liveness detection capability, user authentication capability, user identity confirmation capability, and that may include any or all of a processor, interface, memory, a location device (e.g., GPS), a camera, and display capability. Although embodiments described below advantageously use camera and location features available in many communication devices, as well as user interface screens displayed on the device, it will be appreciated that there may be scenarios where the communication device primarily functions to forward information from the testing device (with or without location or other communication device generated information) with minimal or no visual or other user interface. For example, tests by the testing device may be timed or initiated automatically in response to trigger signals from a server without requiring user interaction with a user interface. This may be desirable, for example, to reduce power consumption and extend battery life of the communication device. Communication device 130 is shown with a processor 132, a memory 134, an interface 136, a camera 138, a network interface 140 (e.g., wired and/or wireless interface), and a display 142. Display 142 is for example a touch screen that allows a user of communication device 130 to make selections, receive instructions, and confirm notifications. Network interface 140 represents a wireless transceiver for communicating with a cellular communication network or Wi-Fi network for example. Interface 112 of testing device 102 and interface 136 of communication device 130 communicate with one another and may represent either a wired electrical interface (e.g., using a physical plug and socket) or a wireless interface (e.g., wireless transceivers that implement Wi-Fi, Bluetooth, NFC or other similar wireless protocols). Interface 112 may also implement a wired connection such as USB or other such connections without departing from the scope hereof.

In one embodiment, interface 136 is configured to ensure that only one testing device 102 communicates with communication device 130 at any time, and thereby only one testing device 102 may submit a test result to communication device 130. This configuration thereby prevents other testing devices from being used to submit bogus test values to communication device 130. Testing device 102 may include a flow meter or other device known in the art of Breathalyzers for determining that a full breath has been applied through tube 105.

Testing device 102 also includes a physical positioning mechanism 170 (that may include interface 112 when interface 112 is implemented as a physical connector) for physically coupling with communication device 130. Communication device 130 is for example one of an iPhone, an Android smart phone, a tablet computer, a laptop computer, other types of mobile computer, an iPod, and an iPad, etc., that is capable of determining its location (e.g., using a GPS receiver or other location determining device) and wherein camera 138 is front facing. Communication device 130 may belong to the test subject, or may be loaned to the test subject by a third party.

When physically coupled together, testing device 102 and communication device 130 are oriented such that camera 138 has a field of view to capture a face image 146 of the test subject providing a sample into tube 105 of testing device 102. Camera 138 may be controlled (e.g., using one or more of flash, auto focus, face detection, blink detection, liveness detection, and so on) by software 144 to improve quality/accuracy of identity determination of the test subject with captured image 146.

In one embodiment, the image is a plurality of images captured periodically during the provision of the sample. In particular, testing device 102 is configured such that, when physically coupled with communication device 130, tube 105, distal portion 122 and display 110 are visible within image 146 captured by camera 138. Further, testing device 102 is configured such that camera 138 also captures image 146 to include a front view of the face of the test subject providing a breath sample into tube 105.

Upon completion of a measurement, BAC value 118 and at least serial number 120 are communicated as digital values from testing device 102 to communication device 130 via interface 112 and interface 136.

Testing device 102 is controlled from communication device 130 via interface 112 and interface 136. Software 144, stored within memory 134 of communication device 130, includes machine readable instructions that when executed by processor 132 interact with testing device 102 to control sensing of BAC value 118 within a breath sample and transfer of BAC value 118 to memory 134. Communication device 130 and testing device 102 are thus synchronized in operation. For example, where communication device 130 is a smartphone, software 144 may represent an app loaded onto and executed by the smartphone.

In one embodiment, communication device 130 includes a biometric reader 150 that is utilized by software 144 to obtain a biometric image (e.g., a finger print, a retinal scan, facial recognition, and so on) of the test subject, wherein the biometric image may be used to provide additional verification of the identity of the test subject. In another embodiment, testing device 102 includes a biometric reader 152 that is utilized by software 116 to capture a biometric image of the test subject, wherein the biometric image is used to provide additional verification of the identity of the test subject.

In one example of operation, a test subject is required to provide between four and six BAC values throughout each day. Software 144 is thereby configured to instruct the test subject to provide a sample at the appropriate times. For example, as shown in steps 1 through 5 of FIG. 2, software 144 provides instructions to the test subject to perform the test and then generates a message 160 containing at least BAC value 118 and image 146. Optionally message 160 also includes one or more of location information, determined from a location device 148 of communication device 130 for example, that defines a location of where the measurement was performed, and serial number 120 of testing device 102.

Figure 2:
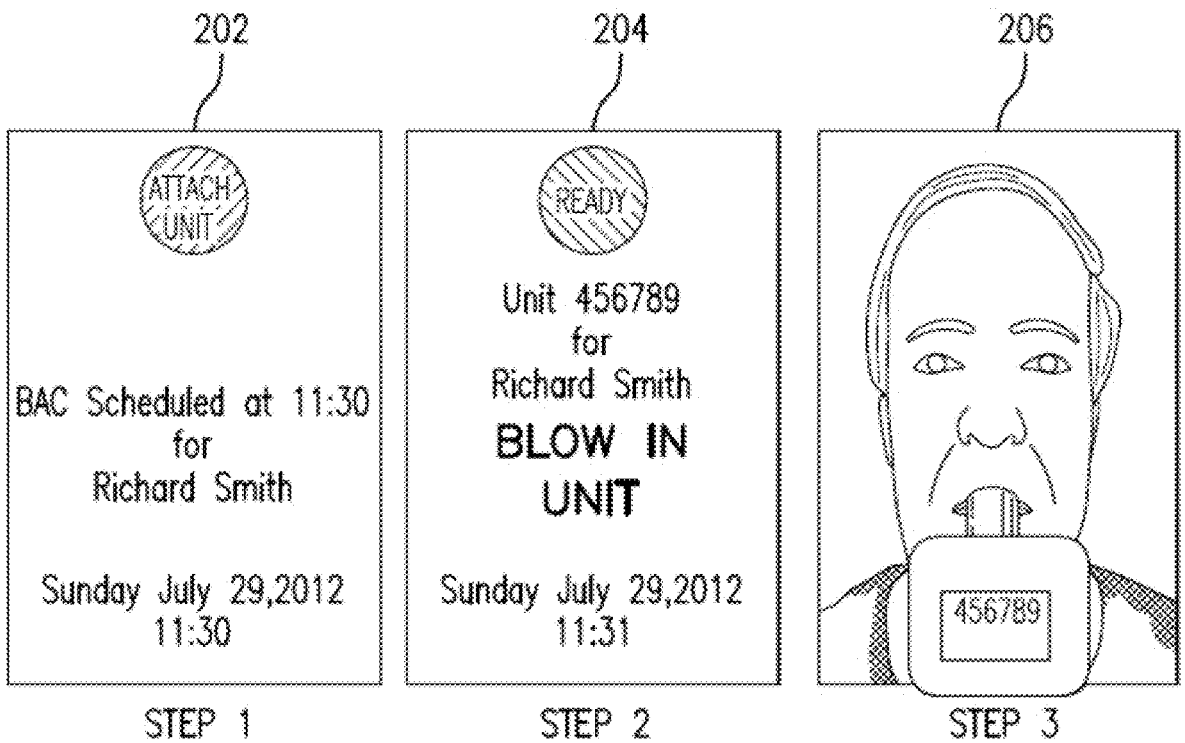
FIG. 2 shows exemplary screen shots from the system of FIG. 1 during use.

In particular, FIG. 2 shows: a screenshot 202 of display 142 of communication device 130 shows step 1 which indicates that the user is scheduled for a BAC test at a specific time and date with instructions to attach the BAC testing device 102 to communication device 130. A screenshot 204 of display 142 of communication device 130 shows step 2 that indicates that testing device 102 is communicating with communication device 130 (using either Bluetooth or some other means via interfaces 112 and 136) and that testing device 102 is ready to measure BAC, and displays instructions for the test subject to blow into tube 105. A screenshot 206 of display 142 of communication device 130 shows step 3 displaying image 146 taken of the test subject blowing into testing device 102 and including a view of display 110 showing serial number 120 of testing device 102 and optionally BAC value 118. BAC value 118, serial number 120, and image 146 captured digitally are disseminated to a server 180 via communication device 130 under control of software 144. For example, software 144, executed by processor 132 generates and sends message 160, including a GPS location, to server 180. One or more of a web application 184 running on server 180, software 144, and software 116, includes facial recognition functionality for automatically recognizing the face of the test subject within image 146 based upon stored images of the test subject within a database 182 of server 180, wherein an alert may be automatically generated and sent to an administrator and/or operator of system 100 if the face of the test subject is not recognized. Thus, the alert may indicate possible fraudulent use of testing device 102. Server 180 is a computer, or network of computers, that includes at least one processor and memory for storing database 182 and web application 184. Web application 184 includes machine readable instructions that are executed by at least one processor to implement functionality of server 180 as described herein.

Where system 100 includes one or both of biometric readers 150 and 152, the captured biometric image may also be included within message 160, wherein web application 184 of server 180 may implement additional validation of the test subject based upon the biometric image and a master biometric image stored within database 182 in association with the test subject, for example. Where the biometric image does not match the master biometric image, web application 184 may generate an alert to an administrator and/or operator of system 100 and/or third party. Thus, the alert may indicate the possibility of fraudulent use of testing device 102.

A screenshot 208 of display 142 of communication device 130 shows step 4 that indicates that the information has been sent successfully to server 180 and that the test is complete. Testing device 102 may then be detached from communication device 130. A screenshot 210 of display 142 of communication device 130 shows step 5 that indicates that testing device 102 has been detached from communication device 130.

Optionally, one or both of testing device 102 and communication device 130 includes a speaker 111, 143 that under control of software 116, 144, respectively, may generate audio to alert the test subject. For example, web application 184 may send a message to communication device 130 that causes speaker 143 to generate a sound, for example to remind the test subject that a next test is overdue. In another example of operation, upon receiving a message from web application 184, communication device 130 sends a message to testing device 102 causing speaker 111 to generate a sound. Thus, system 100 allows a monitoring authority, via one or both of web application 184 and/or communication device 130, to audibly notify the test subject of an overdue test or to request a random sampling for example. One or both of testing device 102 and communication device 130 may include actuators and visual indicators that generate distinctive vibration patterns and/or colored/blinking light patterns for attracting the attention of the test subject.

Communication device 130, under control of software 144, sends message 160 to a server 180 where BAC value 118 and image 146 are processed by a web application 184. Web application 184 is for example a software based control process running within server 180 that automatically processes message 160 against stored requirements of the test subject. In one example of operation, web application 184 may generate a notification (e.g., to an external organization) when message 160 was not received within an expected time window. In another example, when message 160 is received, web application 184 automatically checks that BAC value 118 is below a required threshold for the test subject and then validates the measurement using image 146. Web application 184 may also check other parameters, such as location, within message 160 against permitted values to determine when the test subject is in violation of an agreement and/or requirement.

In one embodiment, for each operation, testing device 102 receives a security code (S/C) 121 that is a randomly generated number from communication device 130 or server 180 and stores S/C 121 within memory 108. S/C 121 is displayed on display 110 such that it is captured within image 146 by camera 138 of communication device 130, and optionally added to message 160. Use of S/C 121 prevents fraudulent use of testing device 102 since S/C 121 cannot be predicted and is generated for each use of testing device 102.

In another embodiment, security unit 114 (or software 116) includes a pseudo random number generator that generates S/C 121 that appears to be random to the test subject. In this embodiment, security unit 114 generates a next number in the sequence for each use of testing device 102, where the same sequence of numbers generated by security unit 114 is also generated within server 180 and thereby allows server 180 to validate each use of testing device 102 to detect misuse thereof. For example, upon receiving message 160, web application 184 automatically detects and recognizes S/C 121 within image 146 and compares the recognized value against the generated (or predicted) S/C 121 and generates a notification when there is a mismatch. Thus, potential misuse (e.g., where the test subject attempts to reuse a previously determined BAC value and image or attempts to use a testing device assigned to another test subject) of testing device 102 is quickly identified.

Figure 18:
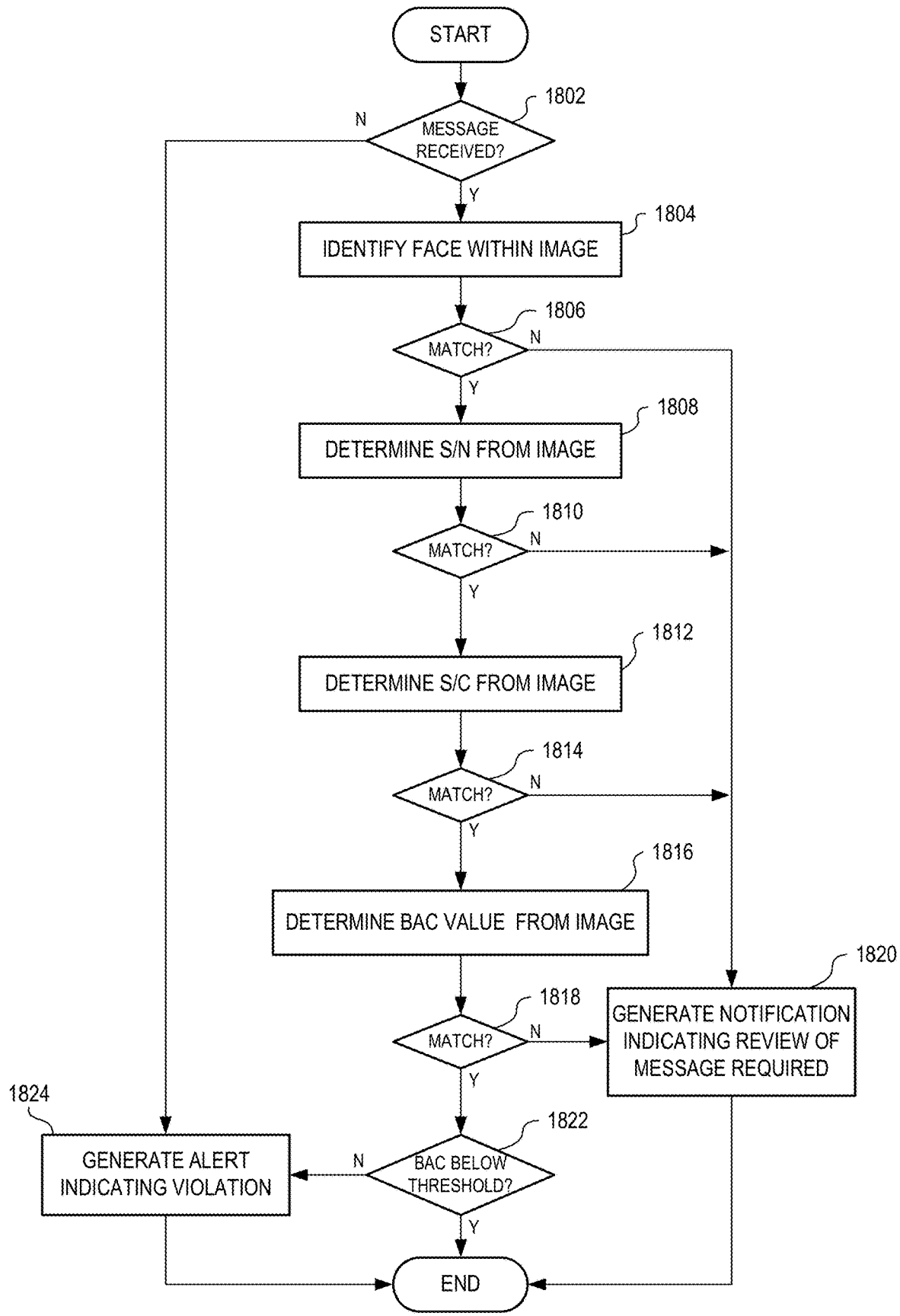
FIG. 18 is a flowchart illustrating one exemplary method for automatically processing information contained within the message of FIG. 1, in an embodiment.

FIG. 18 is a flowchart illustrating one exemplary method for automatically processing information contained within the message of FIG. 1. Method 1800 is for example implemented within web application 184 of server 180 and invoked when testing of a subject is due.

Step 1802 is a decision. If, in step 1802, method 1800 determines that a message has been received, method 1800 continues with step 1804; otherwise method 1800 continues with step 1824. In one example of step 1802, method 1800 continues with step 1804 when message 160 is received within server 180 from communication device 130.

In step 1804, method 1800 identifies a face within an image of the message. In one example of step 1804, web application 184 identifies a face within image 146 received in message 160. Step 1806 is a decision. If, in step 1806, the identified face matches a stored face of the test subject, method 1800 continues with step 1808; otherwise method 1800 continues with step 1820.

In step 1808, method 1800 identifies a serial number within the image. In one example of step 1808, web application 184 identifies a serial number within image 146. Step 1810 is a decision. If, in step 1810, the identified serial number matches the serial number (e.g., S/N 120) stored within database 182 in association with the test subject, method 1800 continues with step 1812; otherwise method 1800 continues with step 1820.

In step 1812, method 1800 identifies a security code within the image. In one example of step 1812, web application 184 identifies a security code within image 146. Step 1814 is a decision. If, in step 1814, the identified security code matches the security code (e.g., S/C 121) associated with the test subject, method 1800 continues with step 1816; otherwise method 1800 continues with step 1820.

In step 1816, method 1800 identifies a BAC value within the image. In one example of step 1816, web application 184 identifies a BAC value within image 146. Step 1818 is a decision. If, in step 1818, the identified BAC value matches the BAC value (e.g., BAC value 118) received in the message (e.g., message 160), method 1800 continues with step 1822; otherwise method 1800 continues with step 1820.

In step 1820, method 1800 generates a notification indicating a review of the message is required. In one example of step 1820, web application 184 generates a notification to an administrator and/or official associated with the test subject indicating that further review of message 160 is required. Method 1800 then terminates.

Step 1822 is a decision. If, in step 1822, method 1800 determines that the BAC value is below a defined threshold, method 1800 terminates; otherwise method 1800 continues with step 1824. In one example of step 1822, web application compares BAC value 118 against a defined threshold within database 182 and continues with step 1824 if BAC value 118 is above the defined threshold.

In step 1824, method 1800 generates an alert indicating a violation. In one example of step 1824, web application 184 generates a message indication violation of substance abuse control and sends the message to an administrator and/or official associated with the test subject. Web application 184 may also require another sample to be taken and/or initiate other actions. For example, web application 184 may send a message indicating the violation to a third party (e.g., a supervisor of the test subject). Method 1800 then terminates.

In one example of use, a court requires that an offender provide a BAC level at predefined intervals throughout the day. Software 144 is configured to remind the offender to provide a BAC level when directed. Upon receiving each sample, web application 184 evaluates the measured BAC value 118 and then processes image 146 to ensure that the sample from which the BAC was measured was provided by the offender.

By providing an automated tamper proof and secure means of BAC measurement, authorities are only alerted when a violation of the BAC is measured or when incorrect or no evidence is presented for authentication. For example, if a test subject fails to send a message 160 to web application 184, an alarm may be raised with authorities. In another example, BAC value 118 has a value of 0.02 when required to be less than 0.01, wherein web application 184 generates and sends an alert to the authorities.

Figure 3:
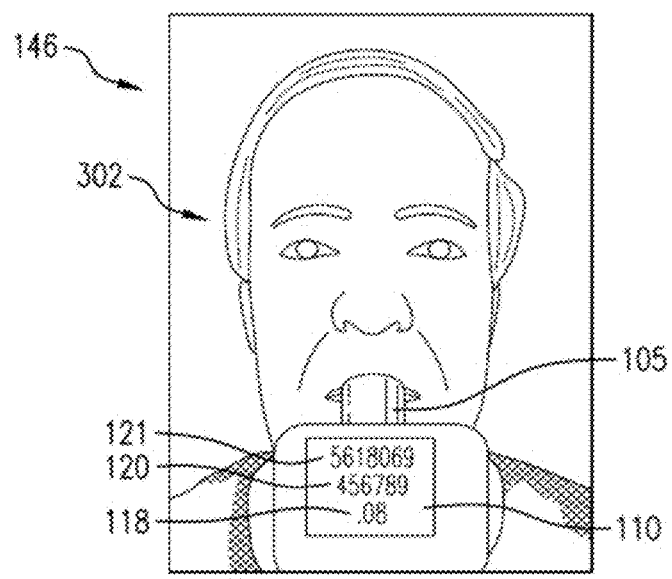
FIG. 3 shows an exemplary image, captured by the communication device of FIG. 1 during the BAC measurement, and illustrating a test subject, the tube, and the display showing a security code, the measured BAC value, and the serial number of the testing device.

FIG. 3 shows image 146, captured by communication device 130 during measurement of BAC value 118, and illustrating test subject 302, tube 105, and display 110. In particular, within image 146, display 110 is displaying S/C 121, serial number 120 and optionally BAC value 118. In certain embodiments, BAC value 118 may be omitted from display 110 where it is not desirable for the test subject to learn of measured BAC values. Physical coupling between testing device 102 and communication device 130 positions camera 138 to consistently capture the face of test subject 302, tube 105, BAC value 118 and serial number 120 within image 146 during operation of testing device 102. The physical coupling is preferably configured such that the camera captures enough of the user's face for verification of identity, e.g., by facial recognition software. In this regard, the illustrated system generally captures the user's face above the upper lip of the user. Further, communication between software 144 of communication device 130 and software 116 of testing device 102 coordinates capture of image 146 with measurement of BAC value 118, thereby ensuring that image 146 provides strong evidence of authenticity of BAC value 118 (i.e., that BAC value 118 corresponds to the test subject captured within image 146).

Figure 4:
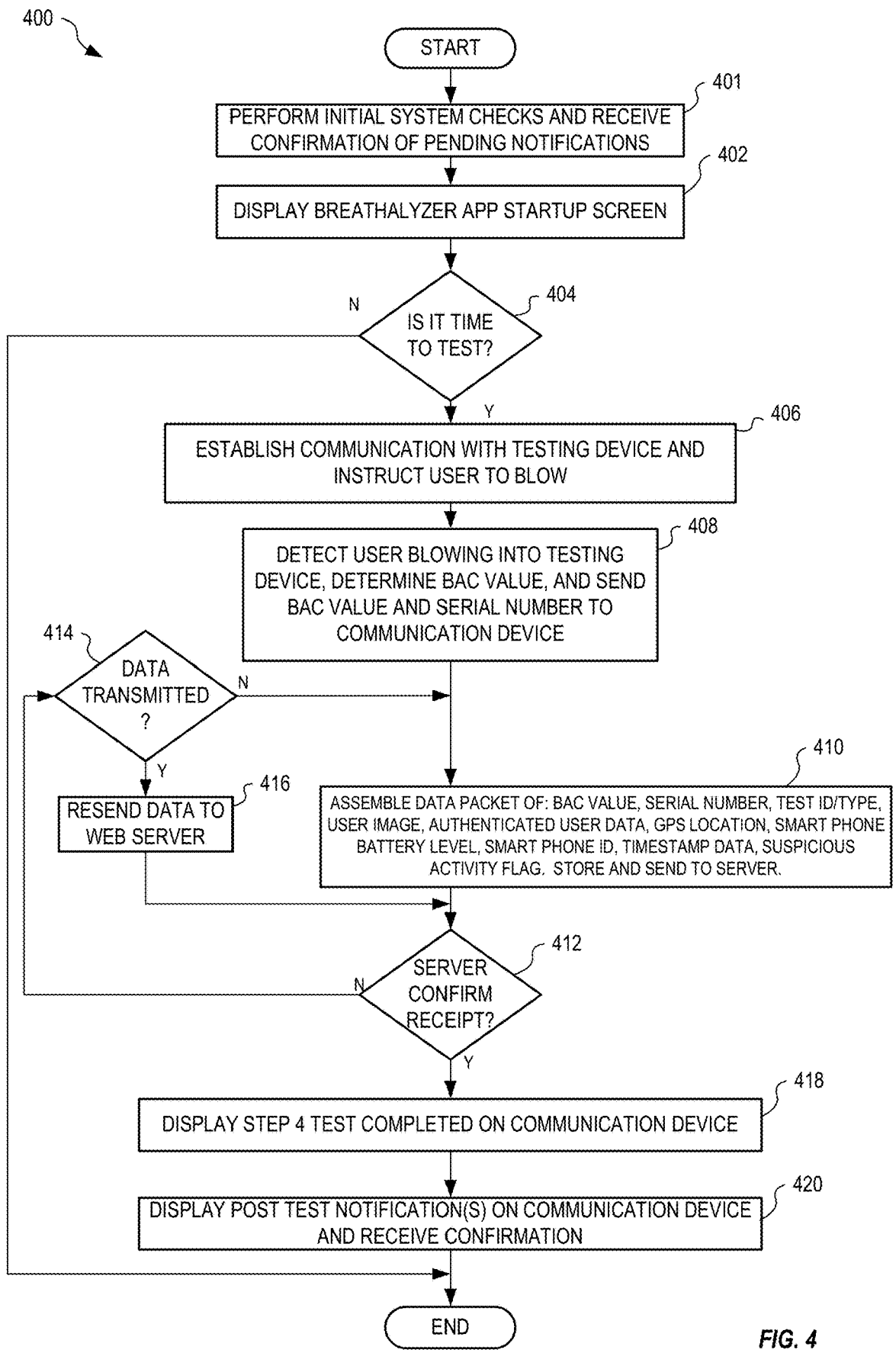
FIG. 4 is a flowchart illustrating one exemplary method for locating and determining substance use, in an embodiment.

FIG. 4 is a flowchart illustrating one exemplary method 400 for locating and determining use of controlled and uncontrolled substances. Method 400 is implemented within software 144 of communication device 130 and software 116 of testing device 102 for example. In step 401, a number of initial system checks may be performed and confirmation of pending notifications may be retrieved. The system first checks to see if Bluetooth and Location services are enabled. If not, the user is prompted to enable them and the system exits if they are not immediately enabled. The system also checks to see if it can take control of the front facing camera. If it fails after several tries the user is informed of the problem and the system exits. In addition, the system may check for a user profile and network connection. If no profile exists and the network is not available, the user is notified and the system exits. The system may also check for a stored Bluetooth device profile. If it does not exist, the system asks the user to select a paired device or pair a new device. If it does exist, a test screen is displayed. At any point until the data packet has been received from the test device, the user may press a button to select/pair a different Bluetooth device. Where the test subject has not responded to one or more previously issued notifications, software 116 may redisplay those notifications and request confirmation from the test subject that they have been read before proceeding further with method 400.

In step 402, method 400 displays a startup screen. In one example of step 402, software 144 displays screenshot 202 on display 142. If all of the initial system checks discussed above are satisfied, the system may proceed to step 404. Step 404 is a decision. If, in step 404, method 400 determines that it is not time to test, method 400 terminates; otherwise, method 400 continues with step 406. The time to test may correspond to a scheduled or an unscheduled test. In one example of step 404, where software 144 has been initiated before a defined testing time window, method 400 terminates.

In step 406, method 400 establishes communication between the communication device and the testing device. In one example of step 406, software 144 displays screenshot 204 on display 142 when communication has been established between communication device 130 and testing device 102 via interfaces 112 and 136. In step 408, method 400 determines a BAC value as the test subject blows into the testing device. In one example of step 408, testing device 102 senses, using sensor 104, breath as test subject blows into tube 105, determines BAC value 118, and then sends BAC value 118 and serial number 120 in a data packet to communication device 130 via interface 112 and interface 136. The data packet may include the BAC value 118, a BAC ID (e.g., security code and serial number), visual confirmation code, battery level, and timing/calibration information.

In step 410, method 400 receives and assembles a data packet of Authenticated User Data, GPS Location, Smart Phone Battery Level, Smart Phone ID, Timestamp Data, and Suspicious Activity Flag, stores the data packet in the memory of the communication device, and sends the data packet to a web application. In one example of step 410, software 144 receives at least BAC value 118 and serial number 120 from testing device 102, controls camera 138 to capture image 146 and creates message 160 containing at least BAC value 118, serial number 120, image 146. Optionally, software 144 also controls location device 148 to determine a current location, and includes the determined current location within message 160. Optionally, software 144 may also include a MAC address of communication device 130, a current time and date, identification of the test subject and a password (previously configured within software 144 and/or memory 134). The system may generate and display (e.g., by LED or LCD) a randomized security code for each test. In this manner, a user is substantially prevented from submitting a false sample from another person or source as the presence of the user can be verified at the time of the test. Software 144 then sends message 160 to server 180 for processing by web application 184.

At least part of the information within message 160 may also be encrypted without departing from the scope hereof. Further, information stored within memory 134 may also be encrypted to prevent duplication and/or modification.

The server may confirm receipt of the data packet and further respond with information regarding the next test. If the next test information is new, it is added to the set of scheduled tests. Step 412 is a decision. If, in step 412, method 400 determines that the web server application has not confirmed receipt of the data packet, method 400 continues with step 414; otherwise method 400 continues with step 418. Step 414 is a decision. If, in step 414, method 400 determines that the data packet has not been transmitted, method continues with step 410; otherwise method continues with step 416. In step 416, method 400 resends the data packet to the web server. In one example of step 416, software 144 resends message 160 to server 180 in this regard.

In step 418, method 400 displays a message indicating that the test is complete. In one example of step 418, software 144 displays screenshot 208 to indicate that the test is complete and that the test subject may disconnect testing device 102 from communication device 130. No matter how the method 400 ends, the system always schedules the next alert (assuming at least one alert remains).

In step 420, method 400 displays a post-test notification on the communication device. In one example of step 420, software 144 display a time of a next test and waits for confirmation from the test subject.

FIG. 5 shows one exemplary BAC web application report 500 generated by web application 184 of server 180 for example. Report 500 is shown containing: an image, name, address, and description of the test subject; a calendar; court and/or other relevant personal information; and detail of tests received from system 100, where each detailed item includes date and time, location, and BAC level of the test. Although FIG. 5 references SMS messages, such messages can be provided by local/push notifications. Notifications of failed or missed tests can be provided by SMS, email, or local/post notifications.

Figure 6:
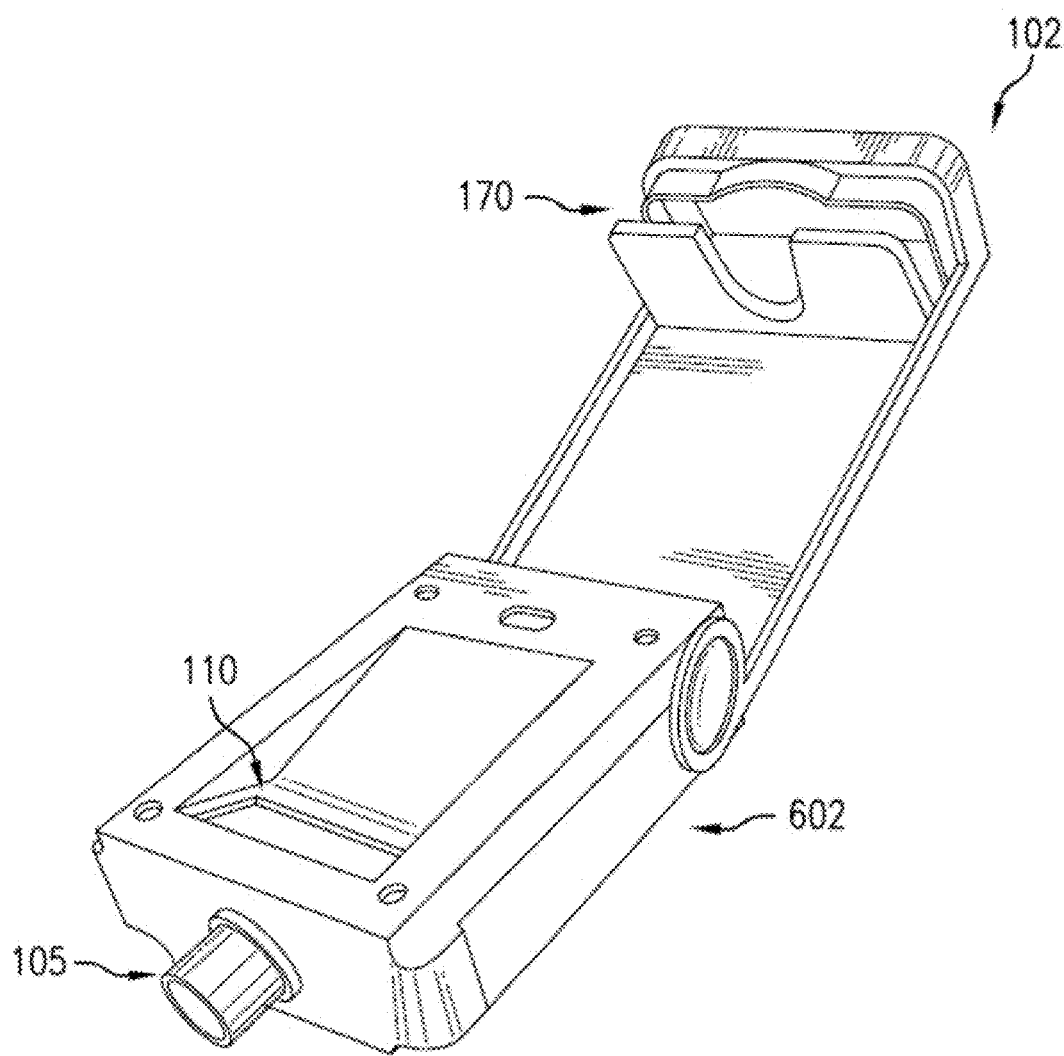
FIG. 6 shows one exemplary physical embodiment of the testing device of FIG. 1 illustrating a casing with the tube and the physical positioning mechanism.

FIG. 6 shows one exemplary physical embodiment of testing device 102 illustrating a casing 602 with tube 105 and physical positioning mechanism 170. As shown, physical positioning mechanism 170 is a cradle that positions communication device 130 such that camera 138 captures a face image of the test subject when blowing into tube 105. As described above, the captured image also includes display 110 indicating serial number 120 and S/C 121. Although FIG. 3 shows the display as further including a BAC value 118, in many cases it will not be desired to display the BAC value to the user and this display element may be eliminated.

In one embodiment, testing device 102 is collapsible to facilitate storage and portability, and to provide protection of certain parts of testing device 102. As shown in FIG. 6, the testing device 102 includes a central pivot such that the device flips between open and closed configurations. In the closed configuration, the device 102 easily fits into a user's pocket. In the open configuration, the physical positioning mechanism 170 positions the camera far enough away from the user's face (i.e., at least about 5 inches, for example, preferably, about 7 inches in the illustrated embodiment) to capture an image as the user supplies a sample at tube 105. A button release allows the device 102 to open smoothly without flopping or a jerky motion as may occur under spring control.

Figure 7:
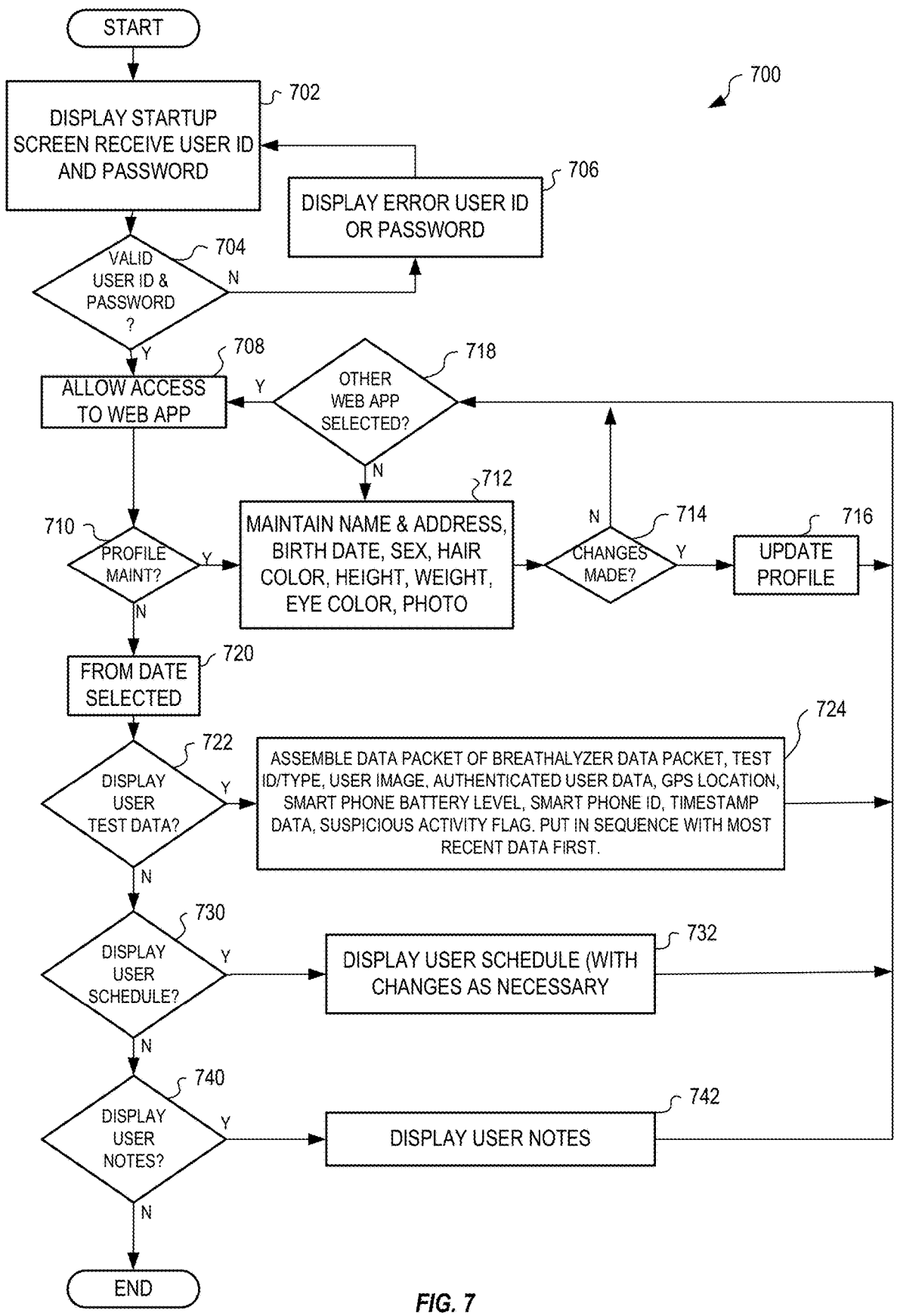
FIG. 7 is a flowchart illustrating one exemplary method for automatically receiving and automatically processing information contained within the message of FIG. 1, in an embodiment.

FIG. 7 is a flowchart illustrating one exemplary method 700 for automatically receiving and automatically processing information contained within message 160 of FIG. 1. Method 700 may display other information without departing from the scope hereof, such as one or more of: court date notifications, billing notifications, schedule change notifications, request (re)upload of test results not received, and so on. Method 700 is implemented within web application 184 of server 180, for example.

It will be appreciated that the method 700 implemented by the web application 184 and/or other software/logic may include a number of maintenance and housekeeping functions that are not shown in FIG. 7. For example, the method 700 may further include change password and create new profile functionality. The method 700 may also include device maintenance, login maintenance and agency maintenance functionality. The application may also manage a To Do list, for example, relating to test data requiring resolution.

Steps 702 through 706 of method 700 prevent unauthorized access to the functionality of steps 708 through 742 by requiring the user to log in. Steps 710 through 718 implement profile maintenance if the user selects the option to edit the profile. In step 712, a user may configure a profile for the test subject. In one example of step 712, a profile is configured within server 180 and stored within database 182 in step 716. In step 720, method 700 receives a selected date. Steps 722 and 724 allow the user to display received and/or stored data packets. In one example of step 724, the user of web application 184 displays message 160 as BAC web application report 500 of FIG. 5.

Steps 730 and 732 allow the user to display a schedule of the test subject. The displayed test schedule may be modified based on any new test scheduling information. Steps 740 and 742 allow the user to display user notes. These user notes may be used to provide the examiner of captured results with more information about circumstances surrounding a particular drug test or user situation, such as where a drug test has been missed. This is particularly important where system 100 is used for court monitored situations. Although not shown, the system may also display assigned devices and notification contacts.

In another embodiment, testing device 102 and communication device 130 communicate with a vehicle ignition system, wherein the vehicle is inoperable until the test subject provides a breath sample with satisfactory BAC value 118. This also provides rolling tests periodically during vehicle operation. All tests are communicated through the communication device 130 (e.g., by sending message 160) to server 180. In certain embodiments, communication device 130 may also display results of any automated verification processes (e.g., facial recognition, liveness detection, suspicious activity detection, security code validation, and so on).

Web application 184 may for example display a template photo of the test subject, taken at the time of enrollment of the test subject, and, for each received test result, display image 146, a scheduled test date and time, a received test date and time, a BAC, a status, and any notes. The user of web application 184 may thereby verify that the test subject has correctly taken the BAC test. Web application 184 may also sort information for display by one or more of: group, positive tests, and missed tests.

In certain embodiments, communication device 130 (e.g., software 144) may identify the presence and position of a face within a field of view of camera 138 based upon live images captured by camera 138. Once a face has been identified, software 144 may determine one or more parameters such as a distance of the face from camera 138, a direction that the face is pointing relative to camera 138, an angle of head tilt of the test subject, presence of additional faces within the field of view, a lighting level, a lighting quality, and/or whether the face is obscured such as by a hat or glasses. For example, software 144 may determine these parameters prior to and/or during facial recognition, liveness detection, and sample capture etc.

Using these parameters, software 144 may provide feedback to the test subject to improve the suitability of pictures being taken by camera 138 for authenticating the identity of the test subject, such as by ensuring that the information captured within the field of view of the camera 138 includes information usable for authenticating the identity of the test subject. For example, where the parameters indicate that the captured images may not be of sufficient quality, or not include the appropriate field of view, to authenticate the identity of the test subject, software 144 may provide one or more instructions to the test subject, such as to adjust a position of camera 138 (communication device 130) in relationship to the test subject's face, to adjust lighting of the test subject's face, to eliminate other people's faces from the field of view of camera 138, to change the orientation of the test subject's head (up/down/left/right), to remove a hat and/or glasses, and to perform an action such as smiling and blinking. Software 144 may provide these directions visually on display 142, audibly using speaker 143, and/or tactilely (by causing the communication device 130 to vibrate. Software 144 may require that these parameters meet a minimum set of requirements, before capturing a picture or permitting the test subject to take a test. Where the test subject requires additional help (or close monitoring), software 144 may stream information from camera 138 (e.g., images and face data) to support personnel such that they may provide further assistance (or review).

Ankle Bracelet

Figure 8:
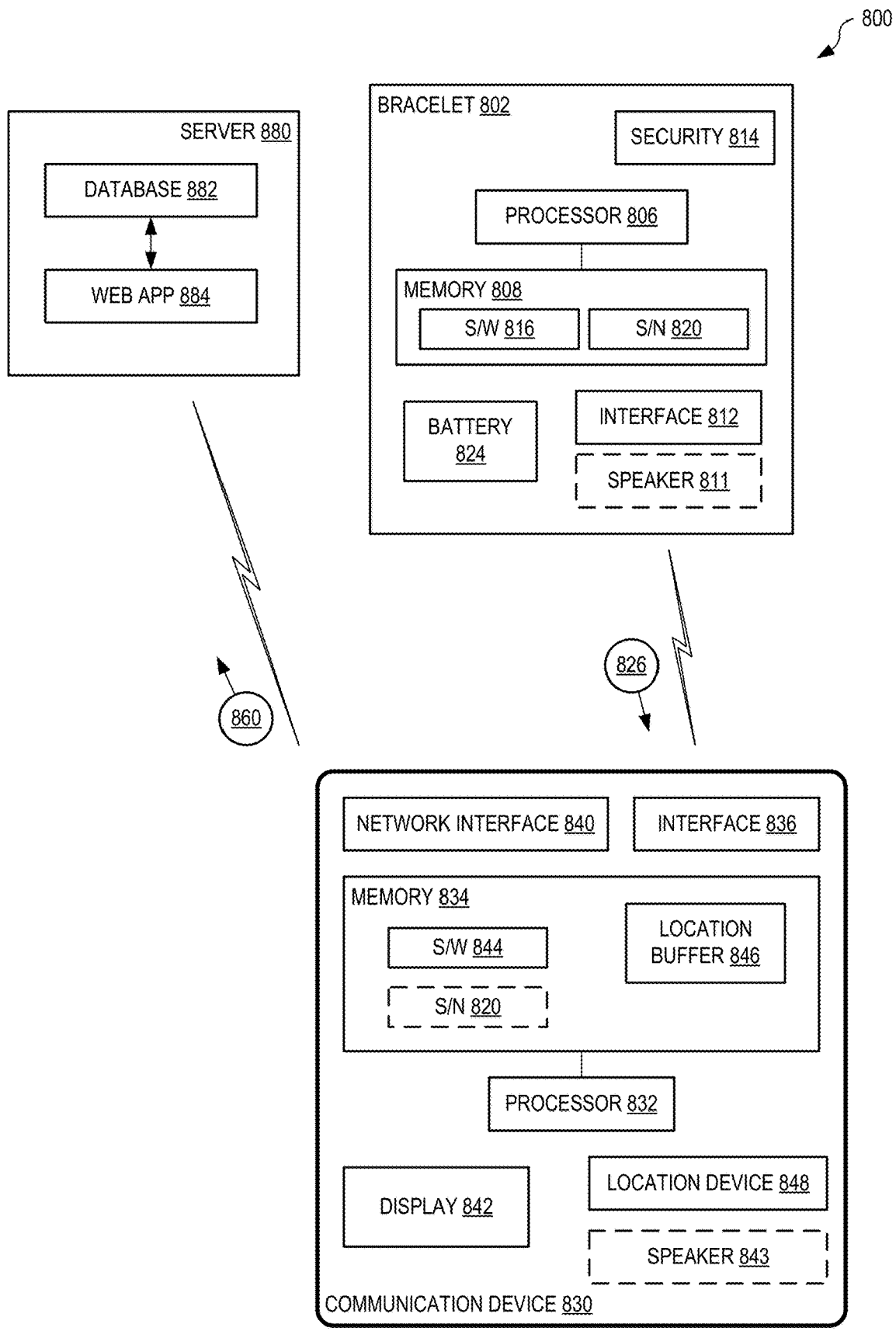
FIG. 8 shows one exemplary system for automatically monitoring movement of an individual, in an embodiment.
Figure 9:
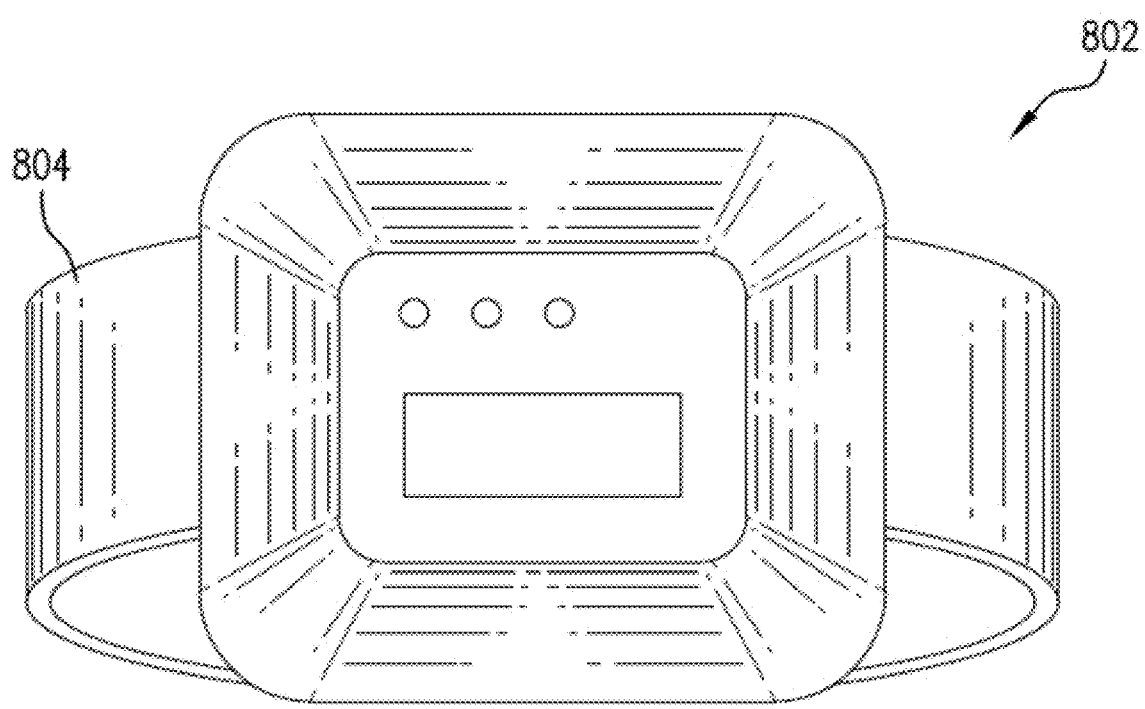
FIG. 9 shows one exemplary perspective view of the ankle bracelet of FIG. 8, in an embodiment.

FIG. 8 shows one exemplary system 800 for automatically monitoring movement of an individual. System 800 includes an ankle bracelet 802 that communicates with a communication device 830 to report the presence of the individual attached thereto. Communication device 830 is for example similar to communication device 130 of FIG. 1 and may represent a smart phone or other similar device that includes cellular communication, a location device (e.g., GPS) and one or more of a processor, an interface, a memory, and display capability (e.g., a user interface). FIG. 9 shows one exemplary perspective view of ankle bracelet 802 of FIG. 8, in an embodiment.

Ankle bracelet 802 includes a tamper evident clip that is destroyed when removal is attempted. Bracelet 802 may include an embedded fiber optic cable, thin copper wire, or other tamper prevention device, within its strap 804 that connects with a security circuit 814 to detect when bracelet 802 is removed, wherein security circuit 814 generates and sends a message 826, via interface 812, to communication device 830 indicating any attempted removal. Communication device 830 then immediately generates and sends (via a network interface 840) a message 860 indicating the removal of bracelet 802 to a web application 884 running on a server 880. Interface 812 is a wireless transceiver that implements a Bluetooth protocol for example. Polling between bracelet 802 and communication device 830 may be individually configured (e.g., between 1 second to 60 minutes), depending on the setting and may be defined by web application 884 for example. If communication device 830 does not receive a signal from bracelet 802 periodically, software 844 running within communication device 830 generates and sends message 860 to web application 884 to indicate the communication failure between bracelet 802 and communication device 830.

Bracelet 802 includes a battery 824 that lasts for up to 12 months for example. The battery may be rechargeable. Alternatively, a replacement battery may be used wherein exchange of the battery within bracelet 802 must be accomplished within one minute or bracelet 802 sends a message 826 to communication device 830 indicating an alarm condition. Each bracelet 802 includes a unique serial number 820 that is stored within memory 834 of communication device 830 when bracelet 802 is paired with communication device 830. Bracelet 802 is for example also waterproof or water resistant.

Optionally, one or both of bracelet 802 and communication device 830 includes a speaker 811, 843 that under control of software 816, 844, respectively, may generate audio to alert the individual. For example, web application 884 may send a message to communication device 830 that causes speaker 843 to generate a sound, for example to remind the individual of an approaching boundary. In another example of operation, upon receiving a message from web application 884, communication device 830 sends a message to bracelet 802 causing speaker 811 to generate a sound. Thus, system 800 allows a monitoring authority, via one or both of web application 884 and/or communication device 830, to audibly notify the individual of inclusion and exclusion restrictions imposed by the monitoring authority for example.

Figure 10:
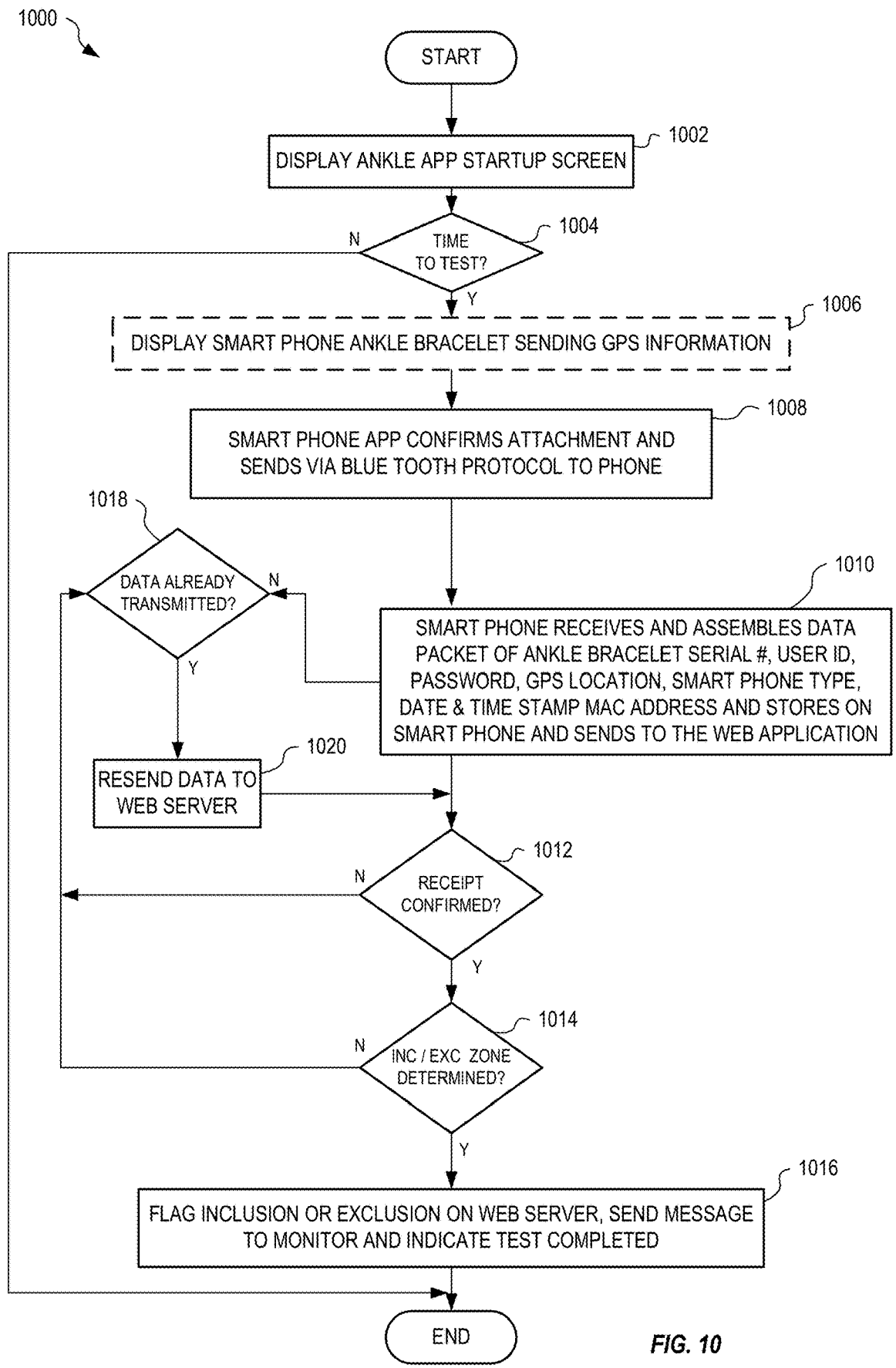
FIG. 10 is a flowchart illustrating one exemplary method for monitoring movement of an individual, in an embodiment.

FIG. 10 is a flowchart illustrating one exemplary method 1000 for monitoring movement of an individual. Steps 1002-1012 and 1016-1020 of method 1000 are for example implemented within software 844 of communication device 830 and step 1014 is implemented within server 880.

In step 1002, method 1000 displays an ankle bracelet application start-up screen. In one example of step 1002, software 844 displays a start-up screen indicating operation of software 844. Step 1004 is a decision. If, in step 1004, method 1000 determines that it is time to test, method 1000 continues with step 1006; otherwise, method 1000 terminates.

In certain embodiments, steps 1002 and 1006 are not included. For example, where tests are to occur without interaction with the test subject (i.e., "silent" testing), steps 1002 and 1006 may be omitted, wherein method 1000 performs automatically and without interaction with the test subject. Where interaction with the test subject is desired (e.g., to capture additional information of the test subject, such as an image and/or biometric data), steps 1002 and 1006 may be included and invoked to interact with the test subject. In certain embodiments, method 1000 may interact with the test subject using other devices, such as a smart watch or other similar device that communicates with communication device 830. If included, in step 1006, method 1000 displays an indication that the communication device is sending location information. In one example of step 1006, software 844 sends a message 860 containing location information, determined from location device 848, to server 880 and displays an indication of the location transfer on display 842. In an alternate embodiment, bracelet 802 also includes a location device for determining a current location of the bracelet, wherein the current location is also communicated to communication device 830 periodically.

In step 1008, method 1000 confirms attachment of bracelet 802 to the individual wirelessly with the communication device. In one example of step 1008, bracelet 802 sends message 826 to mobile device 830, via interfaces 812 and 836, to indicate presence and integrity (and thereby attachment of bracelet 802 to the individual) of bracelet 802. Communication device 830, upon receiving message 826, thereby confirms attachment and presence of bracelet 802 to the individual.

In step 1010, method 1000 assembles a data packet containing a serial number of the bracelet, a user Id, a password, a location, a communication device type, a date and time stamp, and a MAC address of the communication device. The communication device then stores the data packet and sends a message containing the data packet to a server. In one example of step 1010, software 844 generates message 860 to include serial number 820 of bracelet 802, location information from location device 848, a date and time stamp from a real-time clock of communication device 830, and a MAC address of communication device 830. The timestamp within message 860 is compared to the server time and an alarm may be raised when the timestamp is not within certain limits of the server time. In one embodiment, communication device 830 automatically sets its date a time, wherein web application 884 is notified by software 844 when this feature is turned off or overridden, as this may indicate that the individual is tampering with the communication device to defeat the system integrity.

Step 1012 is a decision. If, in step 1012, method 1000 determines that the server confirms receipt of the data, method 1000 continues with step 1014; otherwise, method 1000 continues with step 1018.

Step 1014 is a decision. If, in step 1014, method 1000 determines that the location is within an inclusion zone or without an exclusion zone, method 1000 continues with step 1016; otherwise method continues with step 1018. There could be an inclusion and/or an exclusion zone for any user. The same location information could trigger an inclusion and/or an exclusion zone. The web server software can notify the monitor of the user of a potential violation. The bracelet system may execute geo-fencing functionality.

Step 1018 is a decision. If, in step 1018, method 1000 determines that data has already been transmitted, method 1000 continues with step 1020; otherwise method 1000 continues with step 1010. In step 1020, method 1000 resends the data to the web server. In one example of step 1020, software 844 resends message 860 to server 880. Method 1000 then continues with step 1012.

Figure 11:
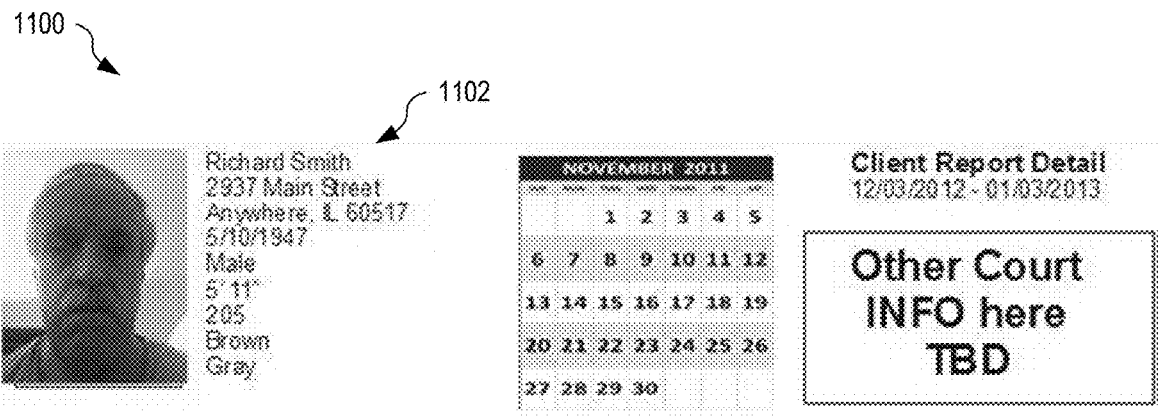
FIG. 11 shows an exemplary location activity report generated by the web application of FIG. 8 running on the server.

FIG. 11 shows an exemplary location activity report 1100 generated by web application 884 running on server 880. Report 1100 includes user identification information 1102 and a list 1104 of reported activity, each activity defining date, time, location, detailed description of activity, court or info, calendar and violations.

Figure 12:
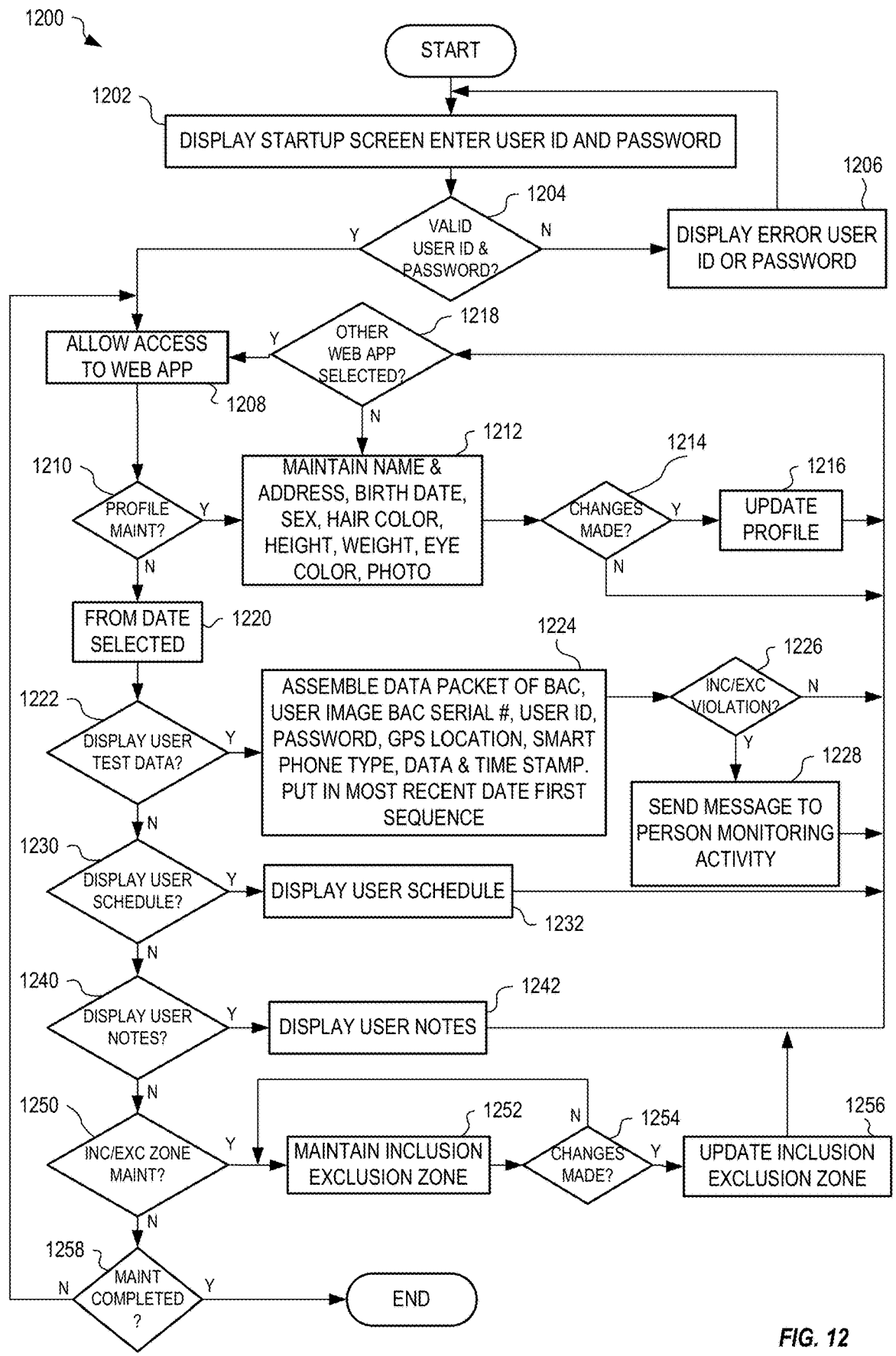
FIG. 12 is a flowchart illustrating one exemplary method for monitoring the location of an individual, in an embodiment.

FIG. 12 is a flowchart illustrating one exemplary method 1200 for monitoring the location of an individual, in an embodiment. Method 1200 is for example implemented within web application 884 running on server 880.

Steps 1202 through 1208 control access to functionality of web application 884, wherein a user (e.g., an administrator and/or official) of web application 884 is required to login with a username and a password. Other access control mechanisms (e.g., biometrics) may be used without departing from the scope hereof.

Step 1210 is a decision. If, in step 1210, method 1200 determines that the user has selected profile maintenance, method 1200 continues with steps 1212 through 1218 that allow the user to create or modify a profile stored within database 882 of server 880.

In step 1220, where profile maintenance is not selected by the user, method 1200 receives a from date. In one example of step 1220, the user selects a past date from which reports will be generated.

Steps 1222 through 1228 allow the user to display captured activity information of the subject. See for example report 1100 of FIG. 11 that shows an activity list for a subject.

Steps 1230 and 1232 allow the user to display the defined schedule for the subject. For example, the displayed schedule may include a reporting interval between location reports for the subject.

Steps 1240 and 1242 allow the user to display any recorded notes on the subject.

Steps 1250 through 1256 allow the user to maintain any defined inclusion and exclusion zones for the subject. For example, the user may define an exclusion zone that causes the communication device to generate an alert display and message when the subject enters a forbidden area. Although the process described above in some cases may involve interaction of the individual being monitored with a user interface of the communication device, it will be appreciated that monitoring events may be executed without generating user interfaces as the communication device, or with minimal user interfaces, as may be desired. For example, timed or notification based alerts can be broadcast (or otherwise delivered) and considered by the web server, communication device and the bracelet automatically. Unless a photo or user provided input is required it can all take place without the need to turn on the communication device display. This approach would also have the beneficial side-effect of consuming far less battery power.

Figure 13:
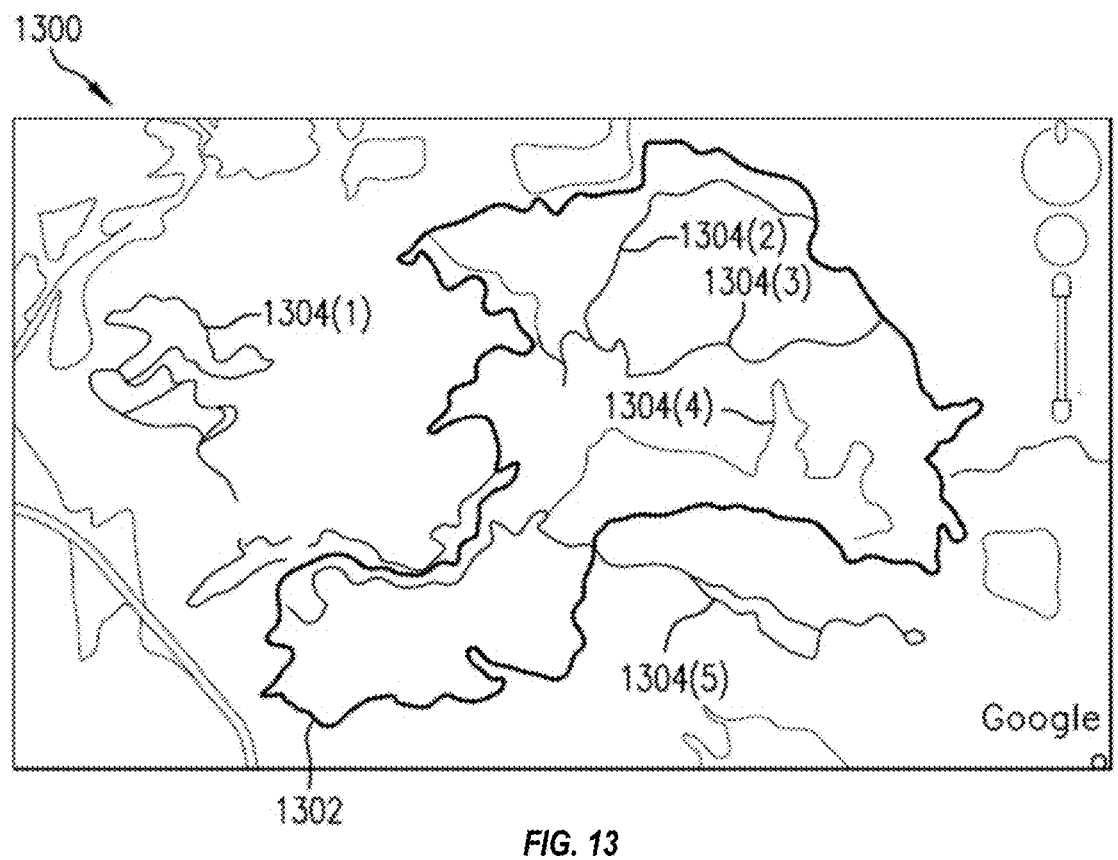
FIG. 13 shows one exemplary map generated by the system of FIG. 8 illustrating an inclusion zone indicated in blue outline, and a plurality of breadcrumb trails that represent the subject's recorded movement.

FIG. 13 shows one exemplary map 1300 within an inclusion zone 1302 indicated in blue outline, and a plurality of breadcrumb trails 1304 that represent the subject's recorded movement.

Figure 14:
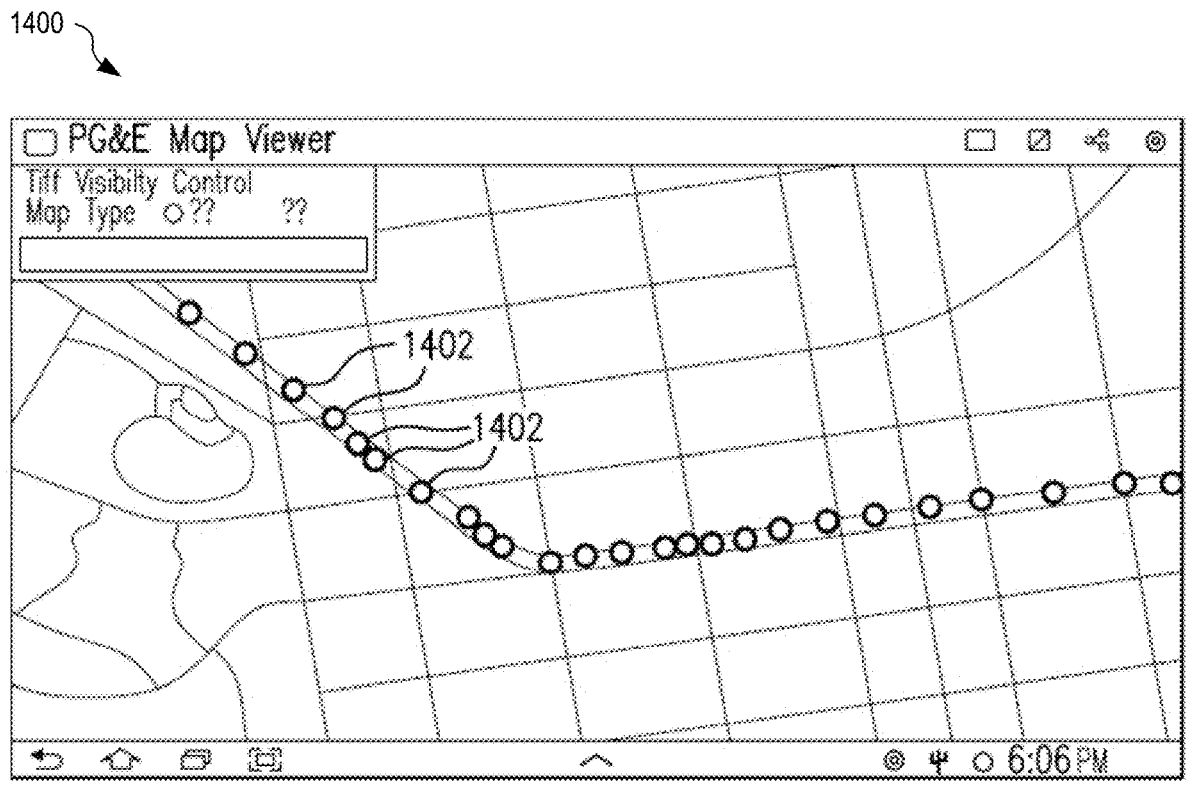
FIG. 14 shows an exemplary map generated by the system of FIG. 8 illustrating a plurality of recorded locations representing movement of the subject.

FIG. 14 shows an exemplary map 1400 indicating a plurality of recorded locations 1402 representing movement of the subject.

Figure 15:
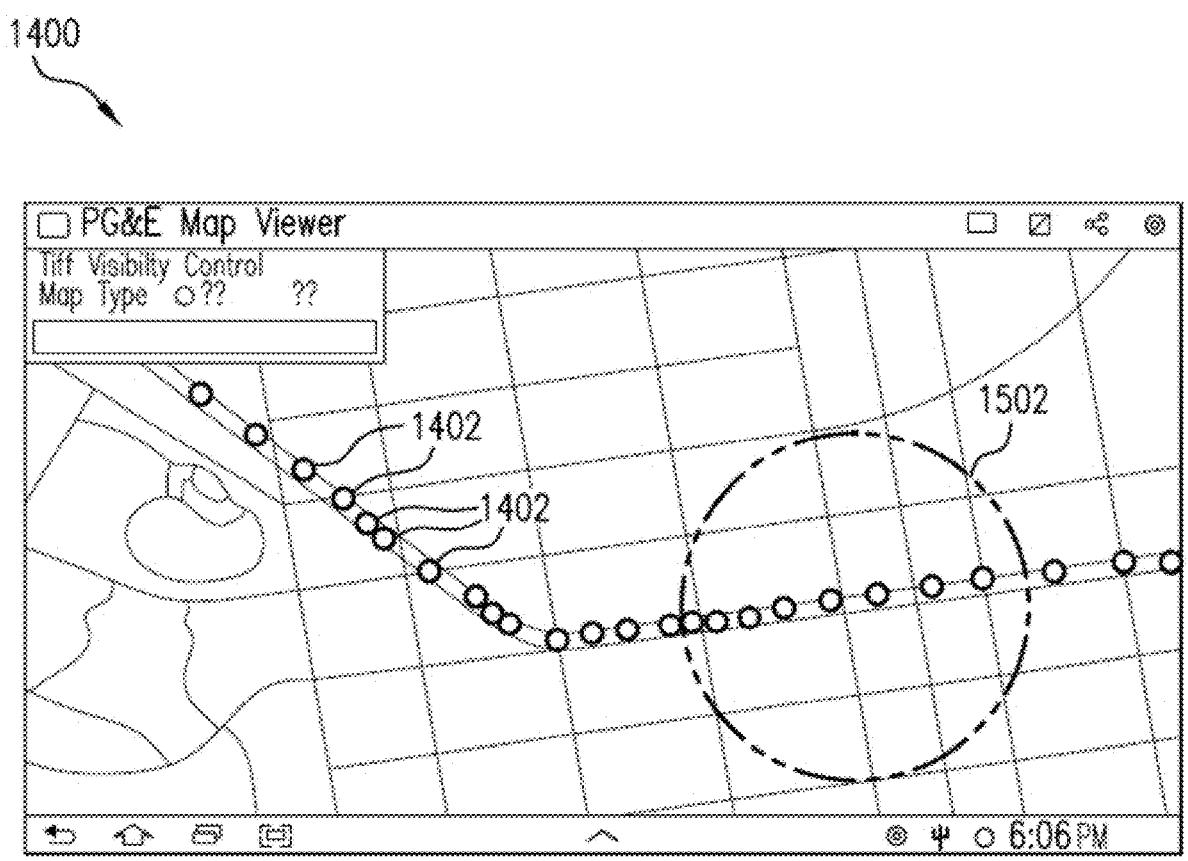
FIG. 15 shows the map of FIG. 14 with an exemplary exclusion zone.

FIG. 15 shows map 1400 of FIG. 14 with a defined exclusion zone 1502.

Web application 884 includes functionality for displaying and printing collected information based upon subject identification, date, time, location and indicated status of the subject. For example, web application 884 may allow the user to display a list of subjects that are currently in violation of defined inclusion and exclusion zones. Web application 884 may also allow the user to send one or more of text messages, audible messages, and indication tones to a tracked subject to prompt the subject to take a particular action (e.g., one or more of take a breath test, return to a defined inclusion zone, and exit from a defined exclusion zone).

Web application 884 may include a GPS tab that displays a map (e.g., a Google map) showing inclusion and exclusion zones for a subject and indicate any violations of the zones graphically. This map may also be interactive, wherein the user may position a mouse over (or click on) a breadcrumb trail or indicated location to display details such as when the location was recorded and whether any violation was reported. The GPS functionality may be used to track a subject and to determine whether the subject is within a certain radius of one or more defined locations (e.g., as defined by a court ruling). For example, within communication device 830, the GPS location may be used to determine if the subject is without an inclusion zone and/or within an exclusion zone and thereby determine that the subject is in violation. Where the subject is in violation of one or more zones, communication device 830 immediately transmits information of the violation to web application 884. The radius of these zones may be individually set for each subject. By communicating frequently with, and identifying within each communication, ankle bracelet 802, communication device 830 verifies that ankle bracelet 802 and communication device 830 are in close proximity (e.g., within communication range of interfaces 812 and 836). Since ankle bracelet 802 cannot be removed from the subject without detection of the removal by communication device 830, the communication device is able to verify that the subject is also in proximity and thereby determine the location of the subject. Communication device 830 may be configured remotely by web application 884. For example, communication device 830 may receive definitions of one or more inclusion zones and exclusion zones from web application 884. In another example, web application 884 may send a reporting interval to communication device 830, wherein the reposting interval may be dynamically adjusted based upon the determined location of the individual. In one embodiment, communication device 830 automatically adjusts the reporting interval based upon the location of the subject relative to one or more defined inclusion and/or exclusion zones. Communication device 830 may also determine and transmit a location of the subject when requested by web application 884.

In the disclosed embodiments, the use of the testing device and the ankle bracelet for reporting information based upon a court ordered procedure is by example only. Systems 100 and 800 may be used to monitor and report other information for other reasons without departing from the scope hereof. For example, parents may use system 800 to track the location of their child and may use system 100 to monitor the level of drug use by their child.

Vehicle Control Device

Figure 16:
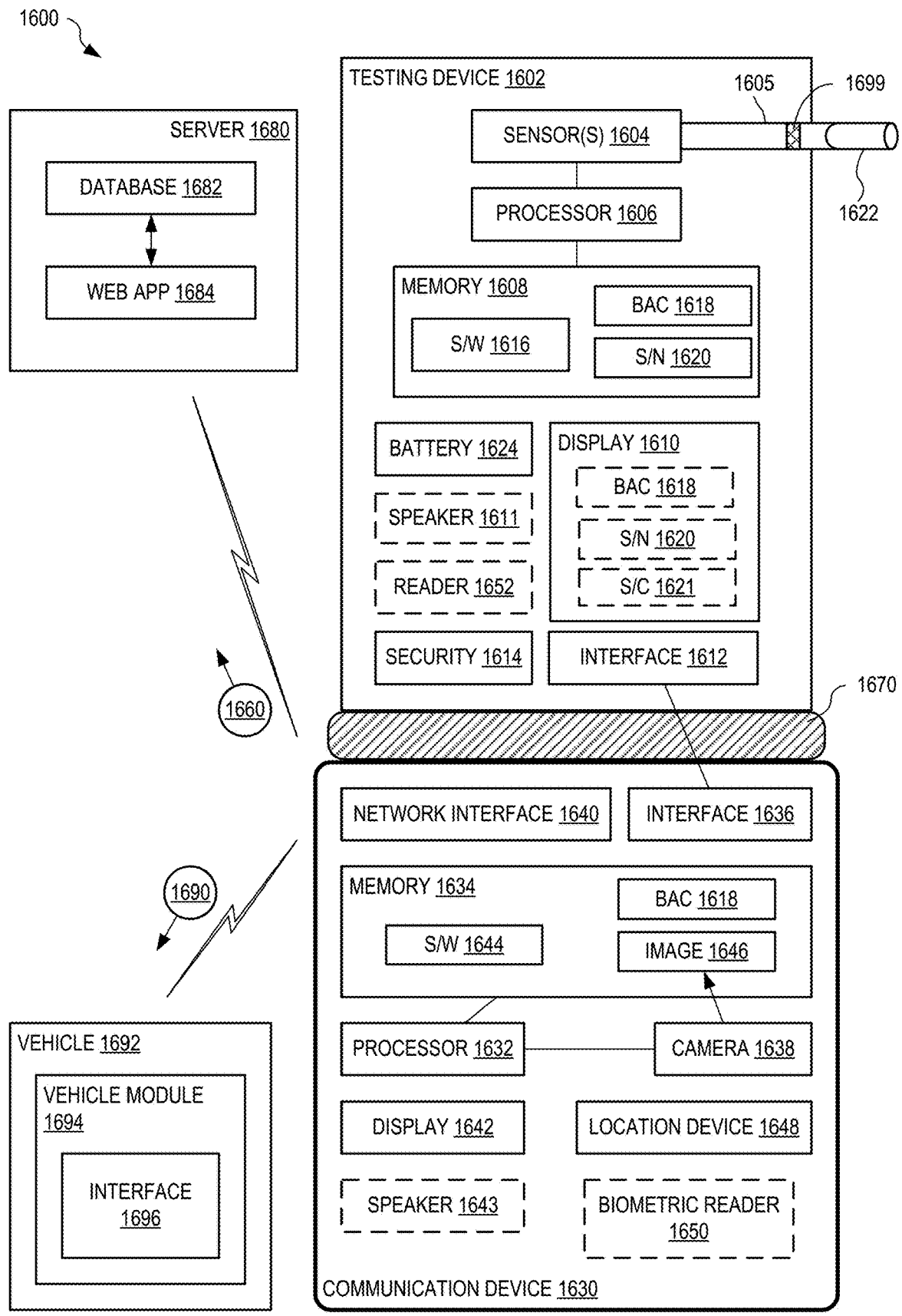
FIG. 16 shows one exemplary system for controlling operation of a vehicle based upon a measured condition of a test subject (e.g., a driver or operator of the vehicle), in an embodiment.

FIG. 16 shows one exemplary system 1600 for controlling operation of a vehicle based upon a measured condition of a test subject (e.g., a driver or operator of the vehicle). System 1600 may control operation of other devices, such as smart home appliances, industrial machinery, computers, and so on, where operation of these other device is not permitted by an impaired operator.

System 1600 includes a testing device 1602 that automatically senses a condition of the test subject. Testing device 1602 includes one or more sensors 1604, a processor 1606, a memory 1608, a display 1610, a secure interface 1612, and a battery 1624. Optionally, testing device 1602 includes a security unit 1614 for monitoring integrity of testing device 1602 and indicating whether testing device 1602 has been compromised (e.g., opened and/or tampered with). Battery 1624 is selected to be of a common type with a long life and that is easily replaceable. Calibration of testing device 1602 is quick and simple.

In one embodiment, sensor 1604 detects Breath Alcohol Concentration (BAC) and is for example implemented using fuel cell technology. Testing device 1602 thus operates as a breathalyzer and includes a tube 1605 that is coupled with sensor 1604 and a distal portion 1622 coupled with tube 1605 and into which the test subject blows. Base portion of tube 1605 is permanently coupled with testing device 1602 to prevent tampering and a distal portion 1622 is replaceable. Tube 1605 may be configured with sensor protection device 1699, such as a cross-hair or mesh, to prevent the test subject from tampering with sensor(s) 1604. For example, the cross-hair and/or mesh prevents the test subject from inserting a foreign object into tube 1605 in an attempt to damage sensor(s) 1604.

Testing device 1602 includes software 1616, stored within memory 1608, having machine readable instructions that when executed by processor 1606 control sensor 1604 to measure BAC value 1618. BAC value 1618 is stored in memory 1608 and displayed on display 1610, as illustratively shown in dashed outline. Software 1616 may also include instructions for operating testing device 1602 that are displayed on display 1610. Security unit 1614 may include a serial number 1620 (shown stored within memory 1608) and an integrity indication (e.g., from security unit 1614) that are also displayed on display 1610 to indicate authenticity of the measured BAC value 1618.

System 1600 also includes a communication device 1630 that is shown with a processor 1632, a memory 1634, an interface 1636, a camera 1638, a network interface 1640, and a display 1642 (e.g., a user interface). Network interface 1640 represents a wireless transceiver for communicating with a cellular communication network for example. Interface 1612 of testing device 1602 and interface 1636 of communication device 1630 communicate with one another and may represent either a wired electrical interface (e.g., using a physical plug and socket) or a wireless interface (e.g., wireless transceivers that implement Bluetooth). Testing device 1602 may include a flow meter or other device known in the art of breathalyzers for determining that a full breath has been applied through tube 1605.

Testing device 1602 also includes a physical positioning mechanism 1670 (that may include interface 1612 when interface 1612 is implemented as a physical connector) for physically coupling with communication device 1630. Communication device 1630 is for example one of an iPhone and an Android smart phone that is capable of determining its location (e.g., using a GPS receiver or other location determining device) and wherein camera 1638 is front facing. When physically coupled together, testing device 1602 and communication device 1630 are oriented such that camera 1638 may capture an image 1646 of the test subject providing a sample into tube 1605 of testing device 1602. In one embodiment, the image is a plurality of images (e.g., a video) captured during the provision of the sample. In particular, testing device 1602 is configured such that, when physically coupled with communication device 1630, tube 1605, distal portion 1622 and display 1610 are visible within image 1646 captured by camera 1638. Further, testing device 1602 is also configured such that camera 1638 also captures image 1646 to include a front view of the face of the test subject providing a breath sample into tube 1605. Camera 1638 may also capture portions (e.g., steering wheel, seat, etc.) of vehicle 1692 within image 1646.

Upon completion of a measurement, BAC value 1618 is communicated from testing device 1602 to communication device 1630 via interface 1612 and interface 1636. Testing device 1602 is controlled from communication device 1630 via interface 1612 and interface 1636. Software 1644, stored within memory 1634 of communication device 1630, includes machine readable instructions that when executed by processor 1632 interact with testing device 1602 to control sensing of BAC value 1618 within a breath sample and transfer of BAC value 1618 to memory 1634. Software 1616 and software 1644 communicate to synchronize operation of testing device 1602 and communication device 1630 to perform functionality described below.

Optionally, BAC value 1618, serial number 1620, and image 1646 are sent, via communication device 1630 under control of software 1644, as a message 1660 to a database 1682 and/or a web application 1684 running on a server 1680. That is, in one embodiment, system 1600 operates similar to system 100 of FIG. 1 to allow web application 1684 to track measurements of testing device 1602. One or more of web application 1684, software 1644 and software 1616 includes facial recognition functionality for automatically recognizing the face of the test subject within image 1646, wherein an alert may be automatically generated if the face of the test subject is not recognized.

A vehicle 1692 is fitted with a vehicle module 1694 that is hard wired to the ignition system of the vehicle for example. Vehicle 1692 represents any type of motorized vehicle with a motor, including a car, a motorcycle, an electric vehicle, a hybrid vehicle, and so on. Vehicle module 1694 prevents operation of the vehicle unless specifically enabled via a wired or wireless interface 1696 within vehicle module 1694 and may also activate the headlamps and/or the horn of vehicle 1692 when a test is required during vehicle operation and indicates a BAC value above a predetermined threshold. That is, system 1600 may operate to perform BAC tests, using testing device 1602, while the test subject operates vehicle 1692, wherein for safety reasons the headlamps and/or the horn of vehicle 1692 are activated instead of the vehicle being disabled.

In one embodiment, vehicle module 1694 communicates wirelessly, via interface 1696, with network interface 1640 of communication device 1630, wherein communication device 1630 sends an enable signal 1690 to vehicle module 1694 when BAC value 1618 has a value below a predefined threshold to allow unfettered operation of the vehicle. Communication between vehicle module 1694 and communication device 1630 is secure and tamper proof, thereby ensuring that enable signal 1690 cannot be provided by another device. Communication between vehicle module 1694 and communication device 1630 may also be implemented through wires and physical couplings (e.g., a dock for receiving communication device 1630) without departing from the scope hereof. For example, where wireless communication is not considered secure, a wired interface between communication device 1630 and vehicle module 1694 may be provided. Where vehicle module 1694 interfaces directly with a computer system of vehicle 1692, vehicle module 1694 and/or communication device 1630 may utilize added security encryption, for example as required by a vehicle manufacturer.

In one example of operation, communication device 1630 waits to receive a confirmation signal from web application 1684 before sending enable signal 1690 to vehicle module 1694. In one embodiment, the confirmation signal is granted by a third party via web application 1684, such as when a parent grants authority for a son or daughter to use vehicle 1692, or such as when, during an emergency situation, even when BAC value 1618 is above the predefined threshold, operation of vehicle 1692 is allowed.

In an alternate embodiment, vehicle module 1694 communicates directly with testing device 1602 via interfaces 1696 and interface 1612 (or via a hard-wired interface), wherein vehicle module 1694 includes intelligence (e.g., a processor, memory, and software) that determine whether the vehicle should be operable (i.e., enabled) based upon the BAC value 1618 received from testing device 1602 within enable signal 1690. In one example of operation, testing device 1602 and vehicle module 1694 form a secure communication link, wherein operation of testing device 1602 is controlled by vehicle module 1694 to periodically request BAC testing of samples from the test subject during operation of vehicle 1692. That is, testing device 1602 and vehicle module 1694 may operate independently of communication device 1630 in certain circumstances.

In one embodiment, for each operation of testing device 1602, a security code (S/C) 1621 that is a randomly generated number from communication device 1630 or server 1680 is received and stored within memory 1608. S/C 1621 is displayed on display 1610 such that it is captured within image 1646 by camera 1638 of communication device 1630, and optionally added to message 1660. Use of S/C 1621 prevents fraudulent use of testing device 1602 since S/C 1621 cannot be predicted and is generated for each use of testing device 1602.

In another embodiment, security unit 1614 (or software 1616) includes a pseudo random number generator that generates S/C 1621 that appears to be random to the test subject. In this embodiment, security unit 1614 generates a next number in the sequence for each use of testing device 1602, where the same sequence of numbers generated by security unit 1614 is also generated within server 1680 and thereby allows server 1680 to validate each use of testing device 1602 to detect misuse thereof. For example, upon receiving message 1660, web application 1684 automatically detects and recognizes S/C 1621 within image 1646 and compares the recognized value against the generated (or predicted) S/C 1621 and generates a notification when there is a mismatch. Thus, potential misuse (e.g., where the test subject attempts to reuse a previously determined BAC value and image or attempts to use a testing device assigned to another test subject) of testing device 1602 is quickly identified.

Optionally, one or both of testing device 1602 and communication device 1630 includes a speaker 1611, 1643 that under control of software 1616, 1644, respectively, may generate audio to alert the test subject. For example, web application 1684 may send a message to communication device 1630 that causes speaker 1643 to generate a sound, for example to remind the test subject that a next test is overdue. In another example of operation, upon receiving a message from web application 1684, communication device 1630 sends a message to testing device 1602 causing speaker 1611 to generate a sound. Thus, system 1600 allows web application 1684 and/or communication device 1630 to audibly notify the test subject of an overdue test for example.

Although shown as different devices, communication devices 130, 830, and 1630 may be the same device, wherein functionality of software 144, 844, and 1644 is combined to allow the communication device to operate with any one or more of devices 102, 802, and 1602. In one example, a communication device (e.g., one of communication devices 130, 830, and 1630) couples with a BAC testing device (e.g., one of testing devices 102 and 1602), a bracelet (e.g., bracelet 802) and a vehicle module (e.g., vehicle module 1694), wherein the communication device may also communicate with a web app (e.g., one or all of web applications 184, 884, and 1684) running on one or more servers (e.g., one or more of servers 180, 880, and 1680). In one example of operation, the communication device communicated with the testing device to measure BAC of the test subject, and may also communicate with the bracelet to ensure the proximity of the test subject to the communication device. That is, the communication device, testing device, and bracelet may operate concurrently to measure drug use of the test subject and monitor movement of the test subject. Where the test subject also wishes to operate a vehicle (e.g., vehicle 1692), the communication device and the vehicle module may communicate to enable the vehicle when BAC of the test subject if measured and below a predefined threshold.

Systems 100 and 1600 may also be adapted for monitoring body vitals including one or more of: Blood Sugar level, Heart conditions, Blood attributes, Brain Waves, animal drug levels, perspiration, respiration, and electromagnetic energy, and other body vitals without departing from the scope hereof. For example, communication devices 130, 1630 may communicate with other types of testing device (e.g., a heart rate monitor) such that the communication device may automatically generate an alert when a predefined heart rate threshold (low and/or high) is exceeded. In one embodiment, bracelet 802 includes additional sensors for monitoring certain vitals of the wearer and for sending the measured vitals periodically to communication device 830.

In one embodiment, communication device 1630 includes a biometric reader 1650 that is utilized by software 1644 to obtain a biometric image (e.g., a finger print, a retinal scan, and so on) of the test subject, wherein the biometric image may be used to provide additional verification of the identity of the test subject. In another embodiment, testing device 1602 includes a biometric reader 1652 that is utilized by software 1616 to capture a biometric image of the test subject, wherein the biometric image is used to provide additional verification of the identity of the test subject.

Where system 1600 includes one or both of biometric readers 1650 and 1652, the captured biometric image may also be included within message 1660, wherein web application 1684 of server 1680 may implement additional validation of the test subject based upon the biometric image and a master biometric image stored within database 1682 in association with the test subject, for example. Where the biometric image does not match the master biometric image, web application 1684 may generate an alert to an administrator and/or operator of system 1600. Thus, the alert indicating the possibility of fraudulent use of testing device 1602.

In one embodiment, one or more of testing device 1602, communication device 1630, and server 1680 may also require that the heart rate of the test subject be within a predefined range before vehicle module 1694 enables operation of vehicle 1692. For example, where heart rate of the test subject is measured by one of bracelet 802, fitness trackers, or other such monitors, vehicle module 1694 may require the measured heart rate to be within a range that excludes the possibility of substance abuse. Similarly, if, while the test subject is operating vehicle 1692 and the heart rate suddenly drops to be below the predefined range, operation of vehicle 1692 may be inhibited in a safe way.

Figure 17:
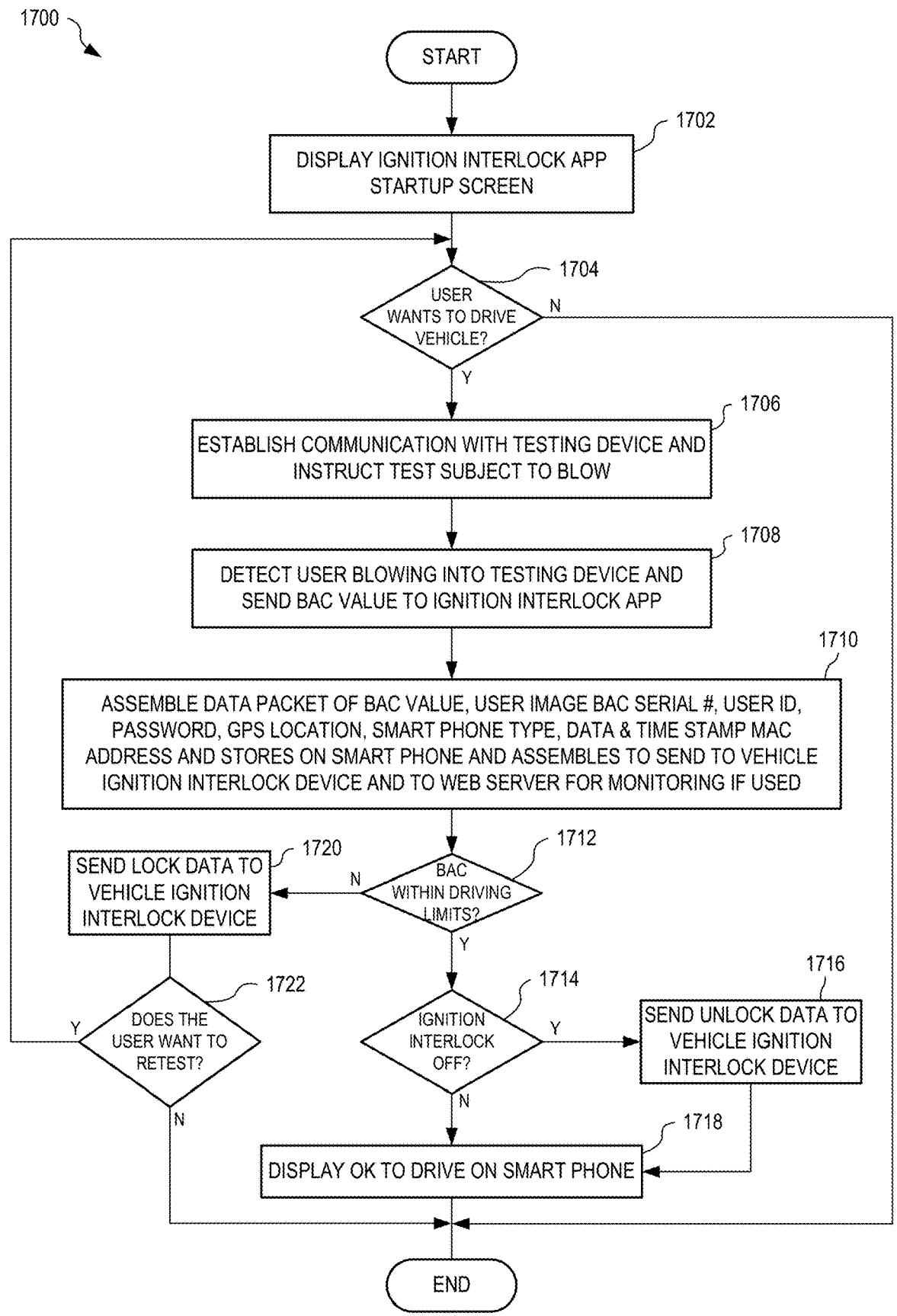
FIG. 17 is a flowchart illustrating one exemplary method for controlling operation of a vehicle based upon a measured condition of an operator of the vehicle, in an embodiment.

FIG. 17 is a flowchart illustrating one exemplary method 1700 for controlling operation of vehicle 1692 based upon a measured condition of a test subject (e.g., a driver or operator of the vehicle). Method 1700 is for example implemented in part within each of: software 1644 of communication device 1630, software 1616 of testing device 1602, and web application 1684 of server 1680.

In step 1702, method 1700 displays an ignition interlock app startup screen. In one example of step 1702, software 1644 displays a startup screen on display1 842 of communication device 1630 to indicate operation of system 1600. Step 1704 is a decision. If, in step 1704, method 1700 determines that the individual wants to drive vehicle 1692, method 1700 continues with step 1706; otherwise, method 1700 terminates.

In step 1706, method 1700 establishes communication between testing device 1602 and communication device 1630 and instructs the test subject to blow. In one example of step 1706, software 1644 displays instructions for the test subject to blow into tube 1605 via distal portion 1622 on display 1642. In step 1708, method 1700 detects the individual blowing into testing device 1602 and measures and sends the BAC to the communication device. In one example of step 1708, testing device 1602 detects the breath as the individual blows into tube 1605, measures BAC value 1618 using sensor 1604, and then sends BAC value 1618 to communication device 1630 via interfaces 1612 and 1636.

In step 1710, method 1700 receives, within the communication device, the BAC level from the testing device, assembles a data-packet containing the BAC, an image of the individual blowing into testing device 1602, and one or more of a BAC serial number, a user ID, a password, a location, a communication device type, a date and timestamp, and a MAC address, and sends the data-packet to a web application running on a server and to a vehicle ignition interlock device. In one example of step 1710, communication device 1630 receives BAC value 1618 from testing device 1602 via interfaces 1612 and 1636, assembles message 1660 containing BAC value 1618, image 1646, captured by communication device 1630 of the individual providing a sample into testing device 1602, serial number 1620, and a date and timestamp. Communication device 1630 then sends message 1660 to web application 1684 and optionally, where vehicle module 1694 contains intelligence, sends enable signal 1690 to vehicle module 1694.

Step 1712 is a decision. If, in step 1712, method 1700 determines that the BAC is within the limits for driving the vehicle, method 1700 continues with step 1714; otherwise, method 1700 continues with step 1720. In one example of step 1712, software 1644 compares BAC value 1618 with a predefined threshold to determine whether the individual has a low enough BAC to operate vehicle 1692.

Step 1714 is a decision. If, in step 1714, method 1700 determines that the ignition interlock has been turned off, method 1700 continues with step 1716; otherwise, method 1700 continues with step 1718. In one example of step 1714, communication device 1630 stores within memory 1634 a status of vehicle module 1694 that indicates whether the ignition interlock is enabled or disabled. In another example of step 1714, software 1644 interrogates vehicle module 1694 to determine the status of the ignition interlock.

In step 1716, method 1700 sends unlock data to the vehicle ignition interlock device. In one example of step 1716, software 1644 sends an unlock code within enable signal 1690 to vehicle module 1694 via interface 1636 to enable unfettered operation of vehicle 1692.

In step 1718, method 1700 displays an "OK to Drive" message on the communication device. In one example of step 1718, software 1644 displays the text "OK to Drive" on display 1642. Method 1700 then terminates.

In step 1720, method 1700 sends lock data to the vehicle ignition interlock device. In one example of step 1720, software 1644 sends enable signal 1690 containing a lock code to vehicle module 1694 to disable operation of the engine of vehicle 1692. Method 1700 then continues with step 1722.

Step 1722 is a decision. If, in step 1722, method 1700 determines that the user wishes to retest, method 1700 continues with step 1704; otherwise, method 1700 terminates. In one example of step 1722, software 1644 interacts with the individual by displaying, using display 1642, a message asking whether to retest, and receives a yes or no input from the individual.

Optionally, one or both of testing device 1602 and communication device 1630 includes a speaker 1611, 1643 that under control of software 1616, 1644, respectively, may generate audio to alert the test subject. For example, web application 184 may send a message to communication device 130 that causes speaker 143 to generate a sound, for example to remind the test subject that a next test is overdue. In another example of operation, upon receiving a message from web application 184, communication device 130 sends a message to testing device 102 causing speaker 111 to generate a sound. Thus, system 100 allows a monitoring authority, via one or both of web application 184 and/or communication device 130, to audibly notify the test subject of an overdue test or to request a random sampling for example.

In certain embodiments, communication device 1630 (e.g., software 1644) may identify the presence and position of a face within a field of view of camera 1638 based upon live images captured by camera 1638. Once a face has been identified, software 1644 may determine one or more parameters such as a distance of the face from camera 1638, a direction that the face is pointing relative to camera 1638, an angle of head tilt of the test subject, presence of additional faces within the field of view, a lighting level, a lighting quality, and/or whether the face is obscured such as by a hat or glasses. For example, software 1644 may determine these parameters prior to and/or during facial recognition, liveness detection, and sample capture etc.

Using these parameters, software 1644 may provide feedback to the test subject to improve the suitability of pictures being taken by camera 1638 for authenticating the identity of the test subject, such as by ensuring that the information within the field of view of the camera 1638 is adjusted to include information usable for authenticating the identity of the test subject. For example, where the parameters indicate that the captured images may not be of sufficient quality to authenticate the identity of the test subject, software 1644 may provide one or more instructions to the test subject, such as to adjust a position of camera 1638 (communication device 130) in relationship to the test subject's face, adjust lighting of the test subject's face, to eliminate other people's faces from the field of view of camera 1638, to change the orientation of the test subject's head (up/down/left/right), to remove a hat and/or glasses, and to perform an action such as smiling and blinking. Additionally, the software 1643 may instruct the test subject to capture a visual representation using the camera 1638 of their location (such as by capturing an image, video, panoramic, or 360-degree panoramic view of their surroundings). Software 144 may provide these directions visually on display 1642, audibly using speaker 1643, and/or tactilely (by causing the communication device 1630 to vibrate. Software 1644 may require that these parameters meet a minimum set of requirements, before capturing a picture or permitting the test subject to take a test. Where the test subject requires additional help (or close monitoring), software 1644 may stream information from camera 1638 (e.g., images and face data) to support personnel such that they may provide further assistance (or review). Furthermore, the software 1644 may, at any time within method 1700, initiate a communication between the communication device 1630 and a third-party device (such as a police officer, parole officer, etc.). This initiated communication may allow the user and/or third party to provide real-time written/verbal communication through the communication device 1630.

Liveness Detection

Increased reliability and reduced cost are always desirable for devices that are to be provided to test subjects. To achieve this, complexity has to be reduced without loss of functionality. For example, it is important to capture evidence that the test subject is providing the sample being tested. This may be in the form of a camera that captures an image of the test subject providing the test sample to the testing device.

Since most people carry a communication device (e.g., a smartphone) that includes a camera and a GPS location device, the camera and the location device may be omitted from the testing device and those of the communication device used to provide evidence of the test subject providing the test sample. This advantageously increases reliability by reducing complexity and cost of the testing device. However, where the camera is not physically included within the testing device, there is no direct and physical correlation for capturing evidence that the test subject is providing the test sample to the testing device.

For example, consider where two testing devices are identical in appearance; a first testing device is communicatively coupled with the communication device that includes a camera that captures one or more images when a test sample is provided to the first testing unit, and a second testing device that is not operational (i.e., a dummy testing device that is not communicatively coupled to the communication device or measuring substance levels).

The camera of the communication device captures the images to provide evidence that the test subject is providing the test sample being tested. However, where the test subject holds the communication device and blows into the second (dummy) testing device while a third party simultaneously provides a sample into the first testing device, the provided sample triggers the communication device to captures images of what appears to be the test subjected providing the test sample. However, in reality, the tested sample was not from the test subject, and thus the test subject has "fooled the system".

To ensure that this cannot occur, additional measures are needed. First, the testing device includes a physical positioning mechanism that positions the communication device such that the camera of the communication device captures: (a) at least part of the face of the test subject providing the sample into the testing device, (b) the distal tip of the tube through which the test sample is provided, and (c) a display of the testing device. That is, the testing device display is configured, positioned, and oriented such that it is captured in the same image as the face of the test subject providing the test sample. By displaying a particular value of the display (e.g., a random number received from a server or generated by the communication device) when the test sample is provided, the image captured of the test subject providing the test sample also includes the random number on the display of the testing device. Thus, the image provides evidence that the correct testing device is being used to receive the test sample from the test subject and that it is communicating with the communication device.

Thus, the position of the display on the testing device, the physical positioning mechanism, and the use of the random number, ensures that the evidence is strong and prevents the test subject from "fooling" the system. Without these features, any captured evidence is inconclusive leaving the system vulnerable to cheating by the test subject.

Additional features are added, as described below, to improve detection of fraudulent activity by the test subject when providing a test sample.

Figure 19:
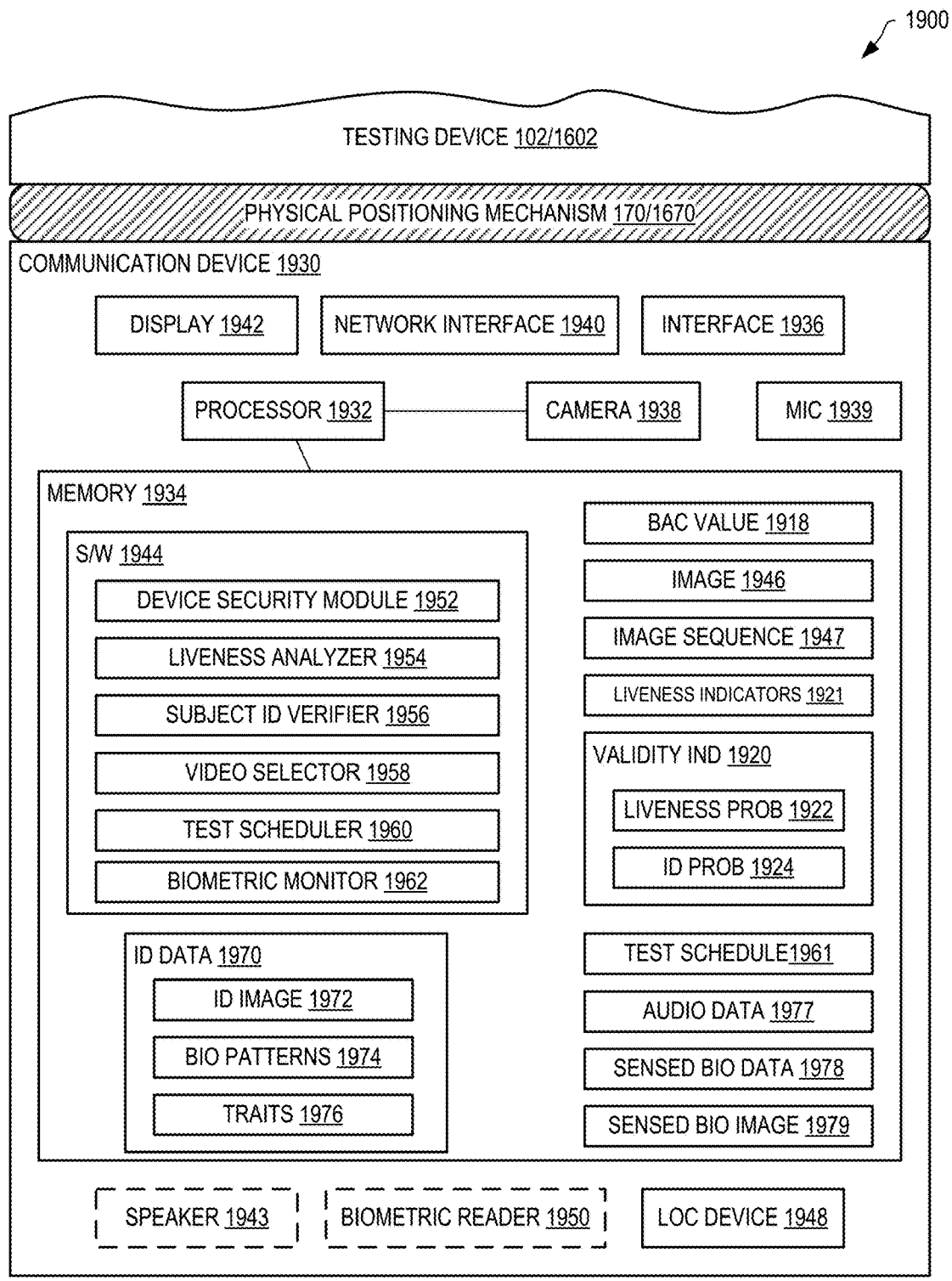
FIG. 19 shows one exemplary system for locating and determining substance abuse, in an embodiment.

FIG. 19 shows one exemplary system 1900 for locating and determining substance abuse. System 1900 includes testing device 102/1602 of FIGS. 1 and 16, respectively, and a communication device 1930 that is physically positioned relative to testing device 102/1602 by physical positioning mechanism 170/1670, as described above. Communication device 1930 may include functionality of one or more of communication devices 130, 830, and 1630 of FIGS. 1, 8, and 16, respectively, to operate with testing device 102/1602.

Communication device 1930 is shown with a processor 1932, a memory 1934, an interface 1936, a camera 1938, a network interface 1940, a display 1942, and a location device 1948 that are similar to processor 132, memory 134, interface 136, camera 138, network interface 140, display 142, and location device 148, respectively, of communication device 130. Memory 1934 is shown storing software 1944 that includes machine readable instructions that when executed by processor 1932 provide communication device 1930 with the functionality described below. Software 1944 is for example an app that is loaded and executed on communication device 1930.

Network interface 1940 represents a wireless transceiver for communicating with a cellular communication network for example. Interface 1936 may communicate with one or more external biometric sensors 1980 that measure one or more of heart rate monitor, respiration rate, perspiration rate, arterial oxygen saturation (SpO2), pulse rate (PR), perfusion index (PI), Plethysmograph Variability Index (PVI), glucose level, and so on. These one or more external biometric sensors 1980 may be configured with articles worn by the test subject, such as one or more of clothing, necklaces, bracelets (including bracelet 802 of FIGS. 8 and 9), and so on, such that data may be sensed continually and/or periodically without being intrusive to the test subject. In one embodiment, one or more external biometric sensors 1980 are configured to continuously and/or periodically detect a substance level within the test subject, wherein a biometric monitor 1962 of communication device 1930 processes the received biometric data and detected substance level to determine substance abuse.

Software 1944 is shown with a device security module 1952, a liveness analyzer 1954, a subject ID verifier 1956, a video selector 1958, a test scheduler 1960, and a biometric monitor 1962.

Device security module 1952 ensures that communication device 1930 connects with testing device 102/1602, and that BAC value 1918 is determined from the test subject providing the current sample. Device security module 1952 controls the start of the testing process and may interact with testing device 102/1602 to synchronize operation of the testing device 102/1602 with communication device 1930. For example, the synchronization between communication device 1930 and testing device 102/1602 ensures that the advanced features implemented by liveness analyzer 1954, subject ID verifier 1956, video selector 1958, test scheduler 1960, and biometric monitor 1962 occur at the appropriate time when the test subject provides the test sample to testing device 102/1602. In certain embodiments, testing device 102/1602 sends an indication to communication device 1930 when the test subject blows (e.g., as detected by a pressure sensor of testing device 102/1602) into distal portion 122/1622 of tube 105/1605, wherein device security module 1952 (or other portions of software 1944) invoke one or more of liveness analyzer 1954, subject ID verifier 1956, video selector 1958, test scheduler 1960, and biometric monitor 1962 to capture image 1946 and/or image sequence 1947, sensed biometric data 1978 and sensed biometric image 1979 and initiate processing thereof, as described below.

In one embodiment, device security module 1952 interacts with interface 1936 to ensure that, during testing of the test subject, communication device 1930 is connected only to one testing device 102/1602. For example, where interface 1940 is wireless and implements one or more of Bluetooth, WiFi, and other such protocols, device security module 1952 operates to exclude other testing devices from concurrently connecting to communication device 1930. Thus, only one testing deice 102/1602 may be used to submit test data to communication device 1930. Such connectivity restrictions ensure that testing device 102/1602 viewed by camera 1938 receiving the sample from the test subject is the one used to provide the test data (e.g., BAC value 1918) to communication device 1930. As described above, camera 1938 is positioned by physical positioning mechanism 170/1670 and controlled to capture image 1946 to simultaneously include both (a) a front view of the face of the test subject providing a breath sample into tube 105/1605 and (b) display 110/1610 of testing device 102/1602. Since, when acquiring the test sample, display 110/1610 is controlled to display security code (S/C) 1621, which is for example a randomly generated number received from server 180 via communication device 1930 or a pseudo random number generated within communication device 1930 and predictable only within server 180/1680 (i.e., not predictable by the test subject), testing device 102/1602 is verified as being the device receiving the test sample from the test subject and verified as being the only testing device 102/1602 in communication with communication device 1930.

In one embodiment, video selector 1958 selects image 1946 and image sequence 1947 from an image stream continually captured by camera 1938 as the test subject configures and utilizes testing device 102/1602 and communication device 1930. Much of this continual image stream is not important or informative, such as when the test subject does not appear within the captures images. Video selector 1958 uses intelligence to processes the continual image stream and determine which images are important and/or of value in identifying and evaluating the test subject and stores these images and image sequences as image 1946 and image sequence 1947.

In one example of operation, video selector 1958 selects image 1946 from the continual image stream when testing device 102/1602 indicates that the test subject is providing a sample. Video selector 1958 evaluates each image and selects one or more images that capture a clear view of the test subject's face with the eyes open (i.e., when the test subject is not blinking). Video selector 1958 also captures one or more image sequences 1947 from the continuous image stream when the test subject is determined to be doing something of interest. For example, video selector 1958 may detect when the test subject is having difficulty physically positioning communication device 1930 and testing device 102/1602 together prior to providing a sample, since such difficulty may indicate a level of sobriety of the test subject. Thus, by determining and selecting images of value from the continual image stream from camera 1938, video selector 1958 reduces the amount of image data that needs to be captured and sent to server 180/1680 for determining the identity of the test subject.

In certain embodiments, communication device 1930 (e.g., device security module 1952 and/or other modules of software 1944) may identify the presence and position of a face within a field of view of camera 1938 based upon live images captured by camera 1938. Once a face has been identified, software 1944 may determine one or more parameters such as a distance of the face from camera 1938, a direction that the face is pointing relative to camera 1938, an angle of head tilt of the test subject, presence of additional faces within the field of view, a lighting level, a lighting quality, and/or whether the face is obscured such as by a hat or glasses. For example, software 1944 may determine these parameters prior to and/or during facial recognition, liveness detection, and sample capture etc.

Using these parameters, software 1944 may provide feedback to the test subject to improve the suitability of pictures being taken by camera 1938 for authenticating the identity of the test subject, such as by ensuring that the information within the field of view of the camera 1938 includes information usable for authenticating the identity of the test subject. For example, where the parameters indicate that the captured images may not be of sufficient quality to authenticate the identity of the test subject, software 1944 may provide one or more instructions to the test subject, such as to adjust a position of camera 1938 (communication device 130) in relationship to the test subject's face, adjust lighting of the test subject's face, to eliminate other people's faces from the field of view of camera 1938, to change the orientation of the test subject's head (up/down/left/right), to remove a hat and/or glasses, and to perform an action such as smiling and blinking. Software 1944 may provide these directions visually on display 1942, audibly using speaker 1943, and/or tactilely (by causing the communication device 1930 to vibrate. Software 1944 may require that these parameters meet a minimum set of requirements, before capturing a picture or permitting the test subject to take a test. Where the test subject requires additional help (or close monitoring), software 1944 may stream information from camera 1938 (e.g., images and face data) to support personnel such that they may provide further assistance (or review).

Figure 20:
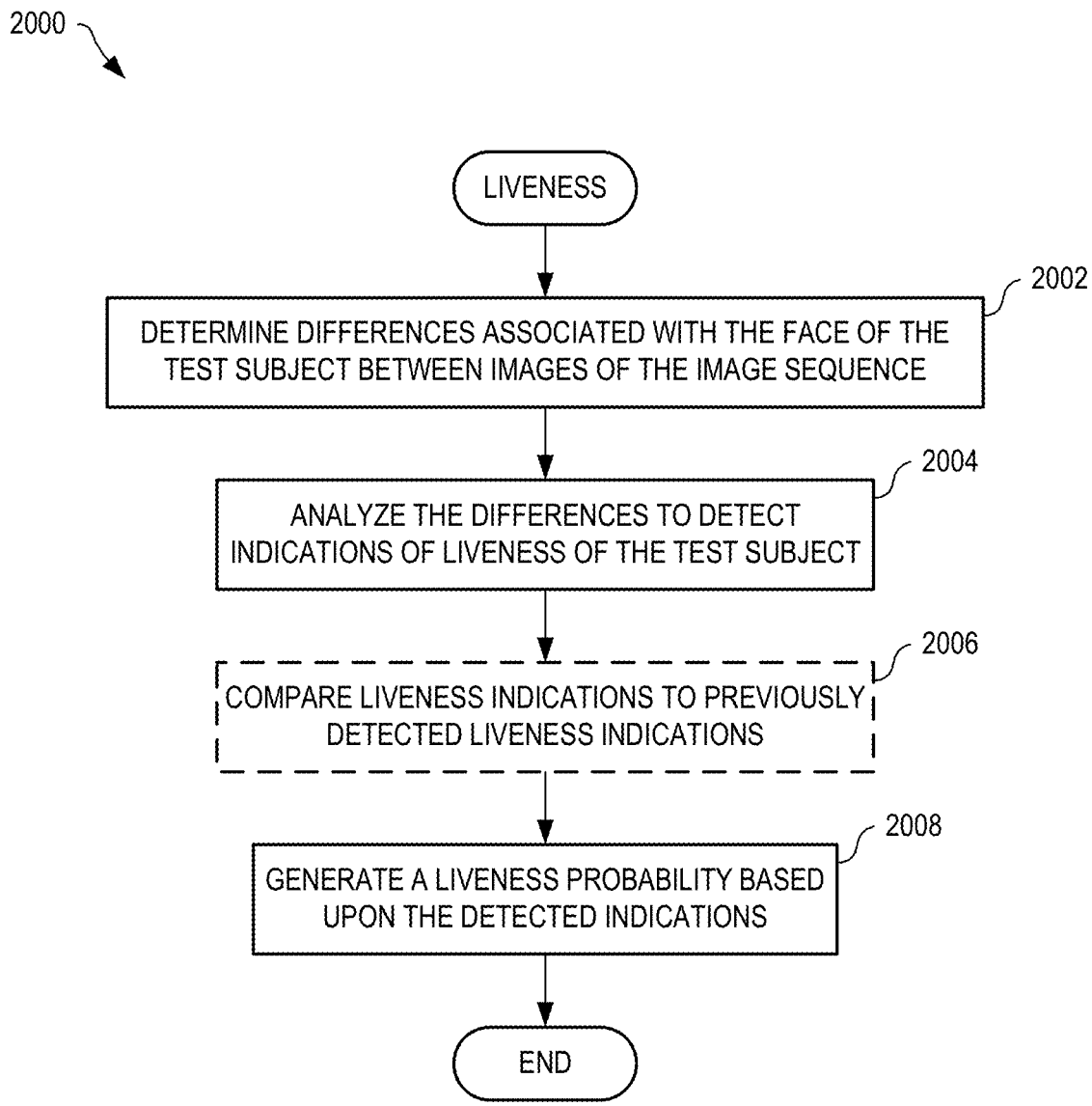
FIG. 20 is a flowchart illustrating one exemplary method for determining the liveness percentage of FIG. 19, which is indicative of liveness of the test subject captured within the image sequence of FIG. 19, in an embodiment.

FIG. 20 is a flowchart illustrating one exemplary method 2000 for determining liveness probability 1922 of FIG. 19, which is indicative of liveness of the test subject captured within image sequence 1947 of FIG. 19. Method 2000 is implemented within liveness analyzer 1954, for example. FIGS. 19 and 20 are best viewed together with the following description.

Liveness analyzer 1954 processes image sequence 1947 and/or image 1946 to determine "liveness" of the test subject providing the test sample. In step 2002 of method 2000, liveness analyzer 1954 compares images in image sequence 1947 to detect changes in the captured face of the test subject. For example, liveness analyzer 1954 processes image 1946 and image sequence 1947 to detect variations in facial features over time. For example, liveness analyzer 1954 may detect changes between images of image sequence 1947 resulting from eye movement and blinking of the test subject. In one embodiment, liveness analyzer 1954 counts blinks for each stage (e.g., before the test sample is provided, while the test sample is provided, and after the test sample is provided) of the testing process. The number of blinks detected at each stage may be used to determine a liveness probability. In another example, liveness analyzer 1954 may detect pulsing of blood flow beneath the skin of the face. When a mask with a likeness of the test subject is used by another individual providing the test sample to testing device 102 in an attempt to avoid detection of the controlled substance in the test subject, liveness analyzer 1954 will not detect indications of liveness within image sequence 1947. That is, even though a mask or image resembling the test subject is used in an attempt to fool system 1900 by replicating the likeness of the test subject within image 1946 and image sequence 1947, the mask cannot replicate movement and other changes in the facial features captured within image sequence 1947 that indicate liveness of the test subject.

Liveness analyzer 1954 may detect many different liveness indications within image sequence 1947, including changes in image intensity resulting from changes in ambient light, consistency in shading of facial features, changes in skin color resulting from blood flow beneath the skin, changes in cheek position during exhale into tube 105/1605, changes in facial expression (e.g., movement of facial muscles), regular movements resulting from breathing, and so on. In step 2004 of method 2000, liveness analyzer 1954 evaluates the detected changes (of step 2002 of method 2000) within image sequence 1947 to identify indicators of liveness, which are stored within memory as liveness indicators 1921.

In one embodiment, in optional step 2006 of method 2000, liveness analyzer 1954 compares currently detected liveness indicators 1921 against previously detected liveness indicators (i.e., detected for previously provided test samples by the test subject), wherein when a previously detected liveness indicator is not currently detected, liveness analyzer 1954 may raise an alarm indicating the change in behavior of the test subject.

Liveness analyzer 1954 may evaluate consistency in detected movement within image sequence 1947 to other sensed inputs, such as heart rate from biometric sensor 1980. For example, where a detected heart rate corresponds to the frequency of detected changes in skin color resulting from pulsing blood flow, liveness analyzer 1954 may increase probability of the corresponding liveness indicator 1921.

In step 2008 of method 2000, liveness analyzer 1954 generates liveness probability 1922 (stored within validity indicator 1920), based upon detected liveness indicators 1921. For example, where liveness indicators 1921 include many indications of liveness, liveness probability 1922 may be generated with a high value (e.g., eighty percent), indicating that it is likely that image sequence 1947 contain images of the live actual test subject, whereas where liveness indicators 1921 includes few indications of liveness, liveness analyzer 1954 may generate liveness probability 1922 with a low value (e.g., thirty percent), indicating that it is unlikely that image sequence 1947 contain images of a live test subject. Validity indicator 1920 is sent to server 180/1680 together with the test results as an indication of their validity.

In one example of operation, liveness analyzer 1954 may determine that where liveness indicators 1921 contains only an indication of detected eye movement, liveness analyzer 1954 generates liveness probability 1922 with a value of thirty percent. Similarly, where liveness indicators 1921 includes only an indication of detected movement of cheek muscles, liveness analyzer 1954 generates liveness probability 1922 with a value of 30 percent. Thus, where a single indication of liveness is detected within image sequence 1947, the probability of the images being of the live test subject is low. However, where liveness indicators 1921 include both eye movement and cheek muscle movement, liveness analyzer 1954 generates liveness probability 1922 with a value of sixty percent, for example, thereby indicating a higher probability that image sequence 1947 captured images of the live test subject.

Image sequence 1947 may further include images captured prior to, and after, the period when the test subject provides the test sample to testing device 102, and may thus show movement of the test subject's lips being position onto tube 105/1605. In one embodiment, liveness analyzer 1954 may select or identify one or more images within image sequence 1947 that provide additional evidence of the liveness of the test subject providing the test sample. By evaluating facial movements, colors and shading within the captured image sequences, liveness analyzer 1954 detects when a static image or mask is used in an attempt to fool system 1900 into believing that a sample was provided by the test subject when it was provided by a third party.

Subject ID verifier 1956 automatically verifies the identity of the test subject providing the test sample based upon sensed inputs. Subject ID verifier 1956 uses one or more images from image 1946, image sequence 1947, audio data 1977, sensed biometric data 1978, and sensed biometric image 1979 to recognize the test subject based upon identification (ID) data 1970 stored within memory 1934.

ID data 1970 stores one or more of ID image 1972 of the test subject, biometric patterns 1974 of the test subject, and traits 1976 of the test subject. ID Data 1970 may be downloaded from server 180 upon each use of software 1944 or stored within memory 1934 upon configuration of communication device 1930.

Subject ID verifier 1956 may verify the identity of the test subject before, during, and/or after, the test subject has provided the test sample. In one example of operation, subject ID verifier 1956 instructs the test subject to provide identification information using one or more of a biometric reader 1950 of communication device 1930, biometric reader 152 of testing device 102/1602, an external biometric sensor 1980, and/or camera 1938. For example, one or both of biometric reader 1950 and biometric reader 152 may be used to capture one or more finger print images of the test subject and store those images as sensed biometric image 1979. In another example, camera 1638 is used to capture an image of an iris/retina of the test subject and store those images as sensed biometric image 1979. In another example, camera 1938 is used to capture a facial image of the test subject and store those images as sensed biometric image 1979. In another example, one or more biometric sensors 1980 are used to capture other biometric data (E.g., ECG, EGG, etc.) from the test subject and store those images as sensed biometric data 1978. In another example, ancillary health and environmental data is collected from other 'smart' devices (iWatch, FitBit, ankle bracelet, vehicle interlock, etc.) and store those images as sensed biometric data 1978.

Sensed biometric data 1978 and/or sensed biometric image 1979 may be compared to ID data 1970. For example, subject ID verifier 1956 compares sensed biometric data 1978 against biometric patterns 1974 to determine if they match, and thereby authenticate the identity of the test subject. Where sensed biometric image 1979 contains an iris/retinal image, sensed biometric image 1979 is compared against an iris/retinal image defined within biometric patterns 1974. Where sensed biometric image 1979 includes a facial image, subject ID verifier 1956 compares sensed biometric image 1979 against ID image 1972 and determines traits within sensed biometric image 1979 for comparison against corresponding traits defined within traits 1976. Based upon matches between sensed biometric data 1978 and sensed biometric image 1979 to ID data 1970, subject ID verifier 1956 generates an ID probability 1924, stored within validity indicator 1920, to indicate a probability of identifying the test subject. For example, where ID probability 1924 is eighty percent, is it likely that sensed biometric data 1978 and sensed biometric image 1979 are from the test subject, whereas where ID probability 1924 is thirty percent, is it likely that sensed biometric data 1978 and sensed biometric image 1979 are not from the test subject.

In another example, a microphone 1939 of communication device 1930 is used to capture audio of the test subject speaking a requested phrase. The captured audio is stored as audio data 1977 and subject ID verifier 1956 uses voice analysis to match audio data 1977 with corresponding biometric patterns 1974.

Subject ID verifier 1956 may use a combination of biometric identification (fingerprint, iris/retinal, face recognition, voice recognition, vein matching, soft biometrics, etc.) in addition to, or as replacement of, photo/video identification and validation. In one embodiment, functionality of subject ID verifier 1956 is implemented within testing device 102/1602. In another embodiment, functionality of subject ID verifier 1956 is implemented within web application 184. Functionality of subject ID verifier 1956 may be implemented in other 'smart' devices without departing from the scope hereof.

Traits 1976 may define one or more physical conditions selected from the group including: skin color, eye color, hair color, presence of beard, presence of moustache, height, and weight. Traits 1976 may also define one or more adhered human characteristics selected from the group including: clothes color, tattoos, and accessories.

As shown in FIG. 19, communication device stores, within memory 1934, a test schedule 1961 that defines time when the test subject is expected to provide a test sample to testing device 102/1602. Test schedule 1961 may be received from remote server 180/1680 and/or configured directly within communication device 1930. Test scheduler 1960 maintains test schedule 1961 and prompts the test subject when it is time to take the next test. Test scheduler 1960 may also update test schedule 1961 automatically based upon one or both of a previous test result and a location of that test.

In one example of operation, where results of a previous test were marginal (i.e., not fails but not ideal), test scheduler 1960 may determine that the next test is to occur within two hours rather than after a previously scheduled four hour period. In another example, where a previous test occurred at a location that was not the user's home or work, test scheduler 1960 may determine that the next test is to occur within two hours rather than after a previously scheduled four hour period.

Where more than one previous test occurred at locations other than those expected (i.e., the user's home or work place), test scheduler 1960 may determine that the next test is to occur within one hour rather than after the default four hour period, wherein the results of the next test are used to validate the previous test results.

In one embodiment, test scheduler 1960 determines when the test subject is due to take the next test based upon a current location of the test subject (e.g., as determined from location device 1948). For example, where previous tests did not occur at expected location, test scheduler 1960 may determine when the test subject arrives at the expected location (e.g., using location device 1948), and schedule an immediate test.

In another example, test scheduler 1960 may automatically update test schedule 1961 to include random tests, such that the test subject is not aware when the next test will occur. For example, were the test subject has previously attempted to defeat identification and sample collection, test scheduler 1960 may be configured to request testing at random times and to have a random number of tests each day, such that the test subject cannot predict when the next test will occur and thereby the test subject cannot be prepared to attempt fraudulent testing.

Biometric monitor 1962 processes data from biometric sensors 1980 to identify effects of substance abuse on the test subject through more conventional biometric monitoring. For example, biometric monitor 1962 may detect a sudden increase in one or both of heart rate and respiration rate, when increased activity is not concurrently detected (e.g., as detected using data from fitness devices and other movement sensors), to determine that the test subject is using a substance. Similarly, biometric monitor 1962 may detect a sudden decrease in heart rate and/or respiration rate, at a time when the test subject is not determined to be asleep, that indicates use of a substance by the test subject. In another example, biometric monitor 1962 may detect when the measured heart rate drops below a level measured when the test subject is asleep to determine use of a substance by the test subject. Thus, biometric monitor 1962 may use biometric data from any available sensor to detect substance abuse at any time by the test subject.

Biometric monitor 1962 may also detect when a sensed condition (e.g., heart rate) is missing, indicating the removal of a device (e.g., ankle bracelet 802) by the test subject, wherein biometric monitor 1962 may attempt to interact with the test subject to correct the problem and/or raise an alarm.

Biometric sensors 1980 may represent sensors of other devices worn or used by the test subject. For example, where the test subject uses a fitness tracker and/or activity monitor, data from these other devices may be input into communication device 1930 and/or server 180 and correlated with data from other biometric sensors 1980 and/or test results generated by testing device 102/1602.

Enhanced Intelligent Testing Device

Figure 21:
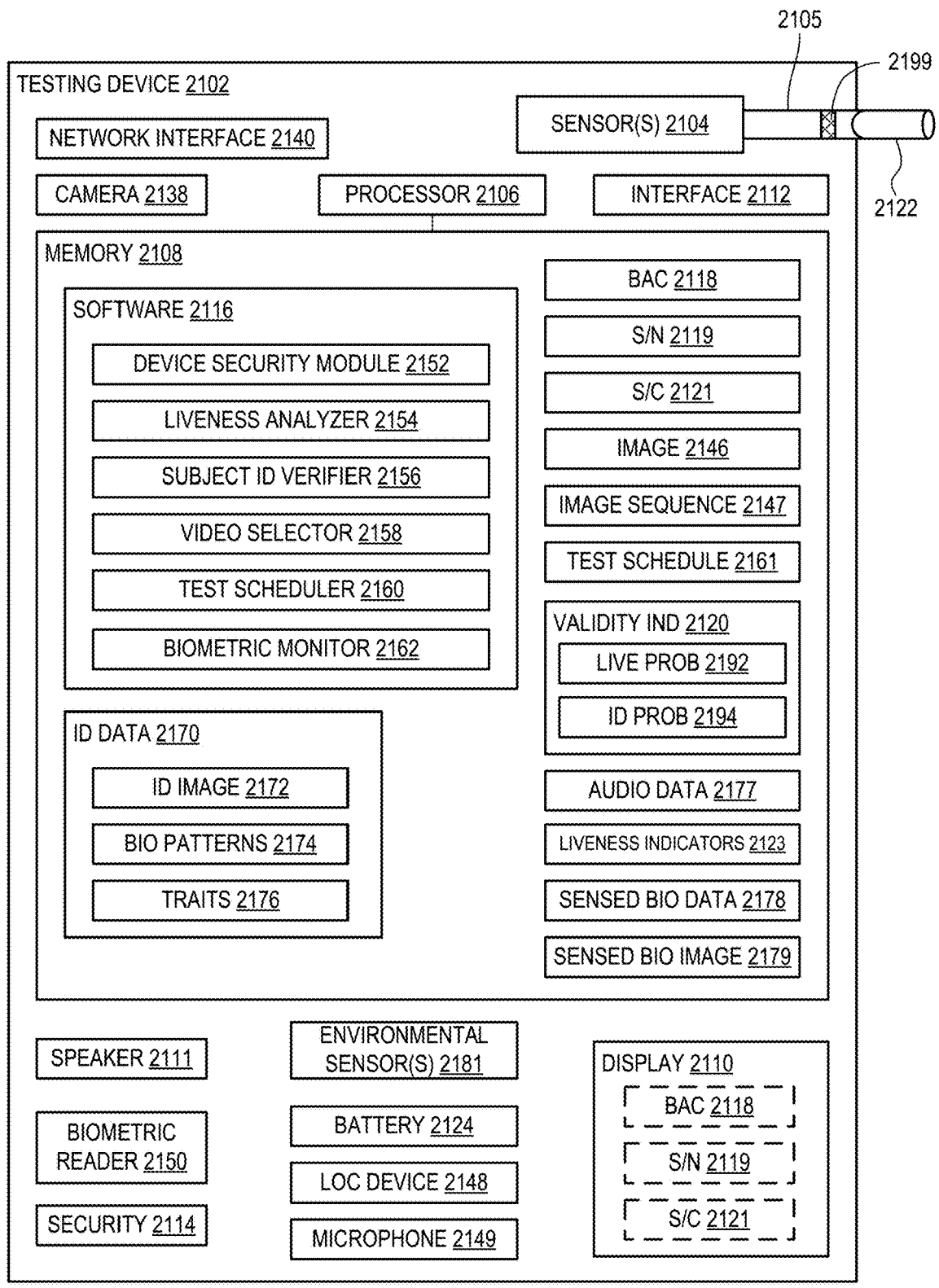
FIG. 21 shows one exemplary intelligent testing device that includes intelligence and communication functionality for locating and determining substance use, in an embodiment.

FIG. 21 shows one exemplary intelligent testing device that includes intelligence and communication functionality for locating and determining substance use. Testing device 2102 includes one or more sensors 2104, a tube 2105 with a distal end 2122, a processor 2106, a memory 2108, a display 2110, a secure interface 2112, a battery 2124, and a security unit 2114 for monitoring integrity of testing device 2102 and indicating whether testing device 2102 has been compromised (e.g., opened and/or tampered with). Tube 2105 may be configured with sensor protection device 2199, such as a cross-hair or mesh, to prevent the test subject from tampering with sensor(s) 2104. For example, the cross-hair and/or mesh prevents the test subject from inserting a foreign object into tube 2105 in an attempt to damage sensor(s) 2104. Battery 2124 is selected to be of a common type with a long life and that is easily replaceable. Testing device 2102 includes software 2116, stored within memory 2108, having machine readable instructions that when executed by processor 2106 provide functionality of testing device 2102 as described herein.

Processor 2106 executes software 2116 to control sensor 2104 to measure BAC value 2118 in a sample provided by the test subject to sensor 2104 via tube 2105. BAC value 2118 is stored in memory 2108 and optionally displayed on display 2110, as illustratively shown in dashed outline. Software 2116 may also include operational instructions that are displayed on display 2110 to instruct the test subject on how to operate testing device 2102. Display 2110 may have a touch sensitive screen and operate as an input device for testing device 2102. Security unit 2114 may include a serial number 2119 (shown stored within memory 2108) unique to testing device 2102 and an integrity indication (e.g., a symbol) that may be displayed on display 2110 to indicate authenticity of the measured BAC value 2118. Security unit 2114 bases the integrity indication upon integrity of testing device 2102. For example, where security unit 2114 detects tampering (e.g., opening) of testing device 2102, the integrity icon is not displayed on display 2110. Testing device 2102 includes functionality of testing device 102 and 1602, and also includes certain functionality of communication devices 130 and 1630, thereby alleviating the need for a separate communication device when communicating with server 180. That is, testing device 2102 may communicate directly with server 180 via wireless and/or wired networks.

Software 2116 is shown with a device security module 2152, a liveness analyzer 2154, a subject ID verifier 2156, a video selector 2158, a test scheduler 2160, and a biometric monitor 2162. Device security module 2152, liveness analyzer 2154, subject ID verifier 2156, video selector 2158, test scheduler 2160, and biometric monitor 2162 operate similarly to device security module 1952, liveness analyzer 1954, subject ID verifier 1956, video selector 1958, test scheduler 1960, and biometric monitor 1962 of communication device 1930 of FIG. 19. That is, certain functionality of communication device 1930 is incorporated into testing device 2102. For example, one or more biometric sensors 2180 are used to capture other biometric data (E.g., ECG, EGG, etc.) from the test subject and store those images as sensed biometric data 2178. In another example, ancillary health and environmental data is collected from other 'smart' devices (iWatch, FitBit, ankle bracelet, vehicle interlock, etc.) and store those images as sensed biometric data 2178.

Device security module 2152 and security unit 2114 may cooperate to ensure testing device 2102 has not been compromised or tampered with, and may include an indication of integrity of testing device 2102 within test results sent to server 180/1680.

Liveness analyzer 2154 processes image sequence 2147 and/or image 2146 to determine "liveness" of the test subject providing the test sample. For example, liveness analyzer 2154 processes image 2146 and image sequence 2147 to detect variations in facial features over time. For example, liveness analyzer 2154 may detect changes between images of image sequence 2147 resulting from eye movement and blinking of the test subject. In one embodiment, liveness analyzer 2154 counts blinks for each stage (e.g., before the test sample is provided, while the test sample is provided, and after the test sample is provided) of the testing process. The number of blinks detected at each stage may be used to determine a liveness probability. In another example, liveness analyzer 2154 may detect pulsing of blood flow beneath the skin of the face. Each detected liveness indication is stored within liveness indicators 2123.

Liveness analyzer 2154 may detect many different liveness indications within image sequence 2147, including changes in image intensity resulting from changes in ambient light, consistency in shading of facial features, changes in skin color resulting from blood flow beneath the skin, changes in cheek position during exhale into tube 2105, changes in facial expression (e.g., movement of facial muscles), regular movements resulting from breathing, and so on.

In one embodiment, liveness analyzer 2154 compares currently detected liveness indicators 2123 against previously detected liveness indicators (i.e., detected for previously provided test samples by the test subject), wherein when a previously detected liveness indicator is not currently detected, liveness analyzer 2154 may raise an alarm indicating the change in behavior of the test subject.

Liveness analyzer 2154 may evaluate consistency in detected movement within image sequence 2147 to other sensed inputs, such as heart rate from biometric sensor 2180. For example, where a detected heart rate corresponds to the frequency of detected changes in skin color resulting from pulsing blood flow, liveness analyzer 2154 may increase probability of the corresponding liveness indicator 2123.

Liveness analyzer 2154 generates a liveness probability 2192 (stored within validity indicator 2120), based upon detected liveness indicators 2123. Validity indicator 2120 is sent to server 180/1680 together with the test results as an indication of their validity.

Subject ID verifier 2156 automatically verifies the identity of the test subject providing the test sample based upon sensed inputs. Subject ID verifier 2156 uses one or more images from image 2146, image sequence 2147, audio data 2177, sensed biometric data 2178, and sensed biometric image 2179 to recognize the test subject based upon identification (ID) data 2170 stored within memory 2108. In one embodiment, a microphone 2149 of testing device 2102 is used to capture audio of the test subject speaking a requested phrase. The captured audio is stored as audio data 2177 and subject ID verifier 2156 uses voice analysis to match audio data 2177 with corresponding biometric patterns 2174.

Sensed biometric data 2178 and/or sensed biometric image 2179 may be compared to ID data 2170. For example, subject ID verifier 2156 compares sensed biometric data 2178 against biometric patterns 2174 to determine if they match, and thereby authenticate the identity of the test subject. Where sensed biometric image 2179 contains an iris/retinal image, sensed biometric image 2179 is compared against an iris/retinal image defined within biometric patterns 2174. Where sensed biometric image 2179 includes a facial image, subject ID verifier 2156 compares sensed biometric image 2179 against ID image 2172 and determines traits within sensed biometric image 2179 for comparison against corresponding traits defined within traits 2176. Based upon matches between sensed biometric data 2178 and sensed biometric image 2179 to ID data 2170, subject ID verifier 2156 generates an ID probability 2194, stored within validity indicator 2120, to indicate a probability of identifying the test subject. For example, where ID probability 2194 is eighty percent, is it likely that sensed biometric data 2178 and sensed biometric image 2179 are from the test subject, whereas where ID probability 2194 is thirty percent, is it likely that sensed biometric data 2178 and sensed biometric image 2179 are not from the test subject.

ID data 2170 stores one or more of ID image 2172 of the test subject, biometric patterns 2174 of the test subject, and traits 2176 of the test subject. ID Data 2170 may be downloaded from server 180 upon each use of software 2116 or stored within memory 2108 upon configuration of testing device 2102.

In one embodiment, video selector 2158 selects image 2146 and image sequence 2147 from an image stream continually captured by camera 2138 as the test subject utilizes testing device 2102. Much of this continual image stream is not important or informative, such as when the test subject does not appear within the captures images. Video selector 2158 uses intelligence to processes the continual image stream and determine which images are important and/or of value in identifying and evaluating the test subject and stores these images and image sequences as image 2146 and image sequence 2147.

In one example of operation, video selector 2158 selects image 2146 from the continual image stream when software 2116 detects that the test subject is providing a sample to testing device 2102. Video selector 2158 evaluates each image and selects one or more images that capture a clear view of the test subject's face with the eyes open (i.e., when the test subject is not blinking). Video selector 2158 also captures one or more image sequences 2147 from the continuous image stream when the test subject is determined to be doing something of interest. For example, video selector 2158 may detect when the test subject is having difficulty operating testing device 2102, since such difficulty may indicate a level of sobriety of the test subject. Thus, by determining and selecting images of value from the continual image stream from camera 2138, video selector 2158 reduces the amount of image data that needs to be captured and sent to server 180/1680 for determining the identity of the test subject.

Test scheduler 2160 maintains test schedule 2161 and prompts the test subject when it is time to take the next test. Test scheduler 2160 may also update test schedule 2161 automatically based upon one or both of a previous test result and a location of that test.

In one example of operation, where results of a previous test were marginal (i.e., not fails but not ideal), test scheduler 2160 may determine that the next test is to occur within two hours rather than after a previously scheduled four hour period. In another example, where a previous test occurred at a location that was not the user's home or work, test scheduler 2160 may determine that the next test is to occur within two hours rather than after a previously scheduled four hour period.

Where more than one previous test occurred at locations other than those expected (i.e., the user's home or work place), test scheduler 2160 may determine that the next test is to occur within one hour rather than after the default four hour period, wherein the results of the next test are used to validate the previous test results.

In one embodiment, test scheduler 2160 determines when the test subject is due to take the next test based upon a current location of the test subject (e.g., as determined from location device 2148). For example, where previous tests did not occur at expected location, test scheduler 2160 may determine when the test subject arrives at the expected location (e.g., using location device 2148), and schedule an immediate test.

In another example, test scheduler 2160 may automatically update test schedule 2161 to include random tests, such that the test subject is not aware when the next test will occur. For example, were the test subject has previously attempted to defeat identification and sample collection, test scheduler 2160 may be configured to request testing at random times and to have a random number of tests each day, such that the test subject cannot predict when the next test will occur and thereby the test subject cannot be prepared to attempt fraudulent testing.

Biometric monitor 2162 processes data from biometric sensors 2180 to identify effects of substance abuse on the test subject through more conventional biometric monitoring. For example, biometric monitor 2162 may detect a sudden increase in one or both of heart rate and respiration rate, when increased activity is not concurrently detected (e.g., as detected using data from fitness devices and other movement sensors), to determine that the test subject is using a substance. Similarly, biometric monitor 2162 may detect a sudden decrease in heart rate and/or respiration rate, at a time when the test subject is not determined to be asleep, that indicates use of a substance by the test subject. In another example, biometric monitor 2162 may detect when the measured heart rate drops below a level measured when the test subject is asleep to determine use of a substance by the test subject. Thus, biometric monitor 2162 may use biometric data from any available sensor to detect substance abuse at any time by the test subject.

Biometric monitor 2162 may also detect when a sensed condition (e.g., heart rate) is missing, indicating the removal of a device (e.g., ankle bracelet 802) by the test subject, wherein biometric monitor 2162 may attempt to interact with the test subject to correct the problem and/or raise an alarm.

Biometric sensors 2180 may represent sensors of other devices worn or used by the test subject. For example, where the test subject uses a fitness tracker and/or activity monitor, data from these other devices may be input into testing device 2102 and correlated with data from other biometric sensors 2180 and/or test results generated by testing device 2102.

Testing device 2102 may also include a network interface 2140, a camera 2138, a location device 2148, and environmental sensors 2181. Network interface 2140 represents a wireless transceiver for communicating with a cellular communication network for example. That is, testing device 2102 may communicate with server 180 via network interface 2140 and thereby not require the use of a separate communication device, such as one of communication devices 130, 830, 1630, and 1930. This allows testing device 2102 to operate independently.

Location device 2148 and environmental sensors 2181 may be used to determine a current location (e.g., geographic location) and environmental conditions of testing device 2102.

Testing device 2102 may also include a biometric reader 2150 (similar to reader 152 of FIG. 1) or may communicate with one or more external biometric sensors 2180 (similar to external biometric sensors 1980 of FIG. 19) and/or other sensing devices that operate to capture biometric images and/or patterns from the test subject. For example, environmental sensors 2181 may include a temperature sensor, an ambient light level sensor, a noise level sensor, and so on that may be used to determine conditions when the test subject takes a test by providing a test sample to testing device 2102. In one embodiment, biometric reader 2150 is physically positioned with testing device 2102 to capture biometric image 2179 of the test subject providing a test sample to testing device 2102. Thus, testing device 2102 may automatically confirm identity of the test subject when a test sample is provided based upon biometric image 2179.

Testing device 2102 communicates with one or more remote servers (e.g., server 180, FIG. 1, server 1680, FIG. 16, server 2280, FIG. 22), to report results including one or more of BAC value 2118, serial number 2119, security code 2121, image 2146, image sequence 2147, validity indicator 2120, sensed biometric data 2178, sensed biometric image 2179, and so on.

In certain embodiments, communication device 2130 (e.g., device security module 2152 and/or other modules of software 2116) may identify the presence and position of a face within a field of view of camera 2138 based upon live images captured by camera 2138. Once a face has been identified, software 2116 may determine one or more parameters such as a distance of the face from camera 2138, a direction that the face is pointing relative to camera 2138, an angle of head tilt of the test subject, presence of additional faces within the field of view, a lighting level, a lighting quality, and/or whether the face is obscured such as by a hat or glasses. For example, software 2116 may determine these parameters prior to and/or during facial recognition, liveness detection, and sample capture etc.

Using these parameters, software 2116 may provide feedback to the test subject to improve the suitability of pictures being taken by camera 2138 for authenticating the identity of the test subject, such as by ensuring that the information within the field of view of the camera 2138 includes information usable for authenticating the identity of the test subject. For example, where the parameters indicate that the captured images may not be of sufficient quality to authenticate the identity of the test subject, software 2116 may provide one or more instructions to the test subject, such as to adjust a position of camera 2138 (testing device 2102) in relationship to the test subject's face, adjust lighting of the test subject's face, to eliminate other people's faces from the field of view of camera 2138, to change the orientation of the test subject's head (up/down/left/right), to remove a hat and/or glasses, and to perform an action such as smiling and blinking. Software 2116 may provide these directions visually on display 2142, audibly using speaker 2143, and/or tactilely (by causing the testing device 2101 to vibrate. Software 2116 may require that these parameters meet a minimum set of requirements, before capturing a picture or permitting the test subject to take a test. Where the test subject requires additional help (or close monitoring), software 2116 may stream information from camera 2138 (e.g., images and face data) to support personnel such that they may provide further assistance (or review).

Server Functionality

Figure 22:
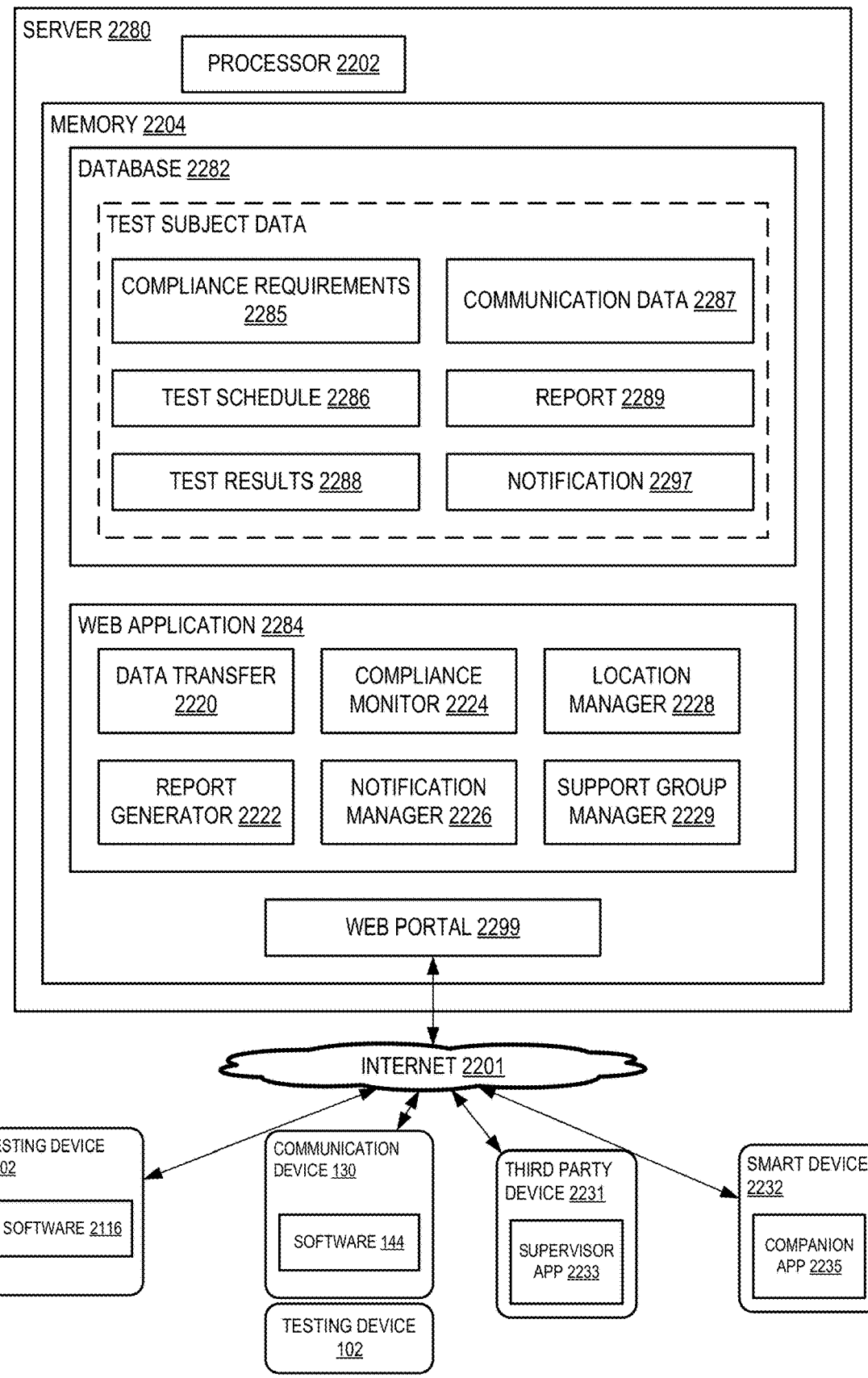
FIG. 22 shows one exemplary server, similar to the server of FIG. 1, showing a web application with compliance management, report generation, and notification management, in an embodiment.
Figure 23:
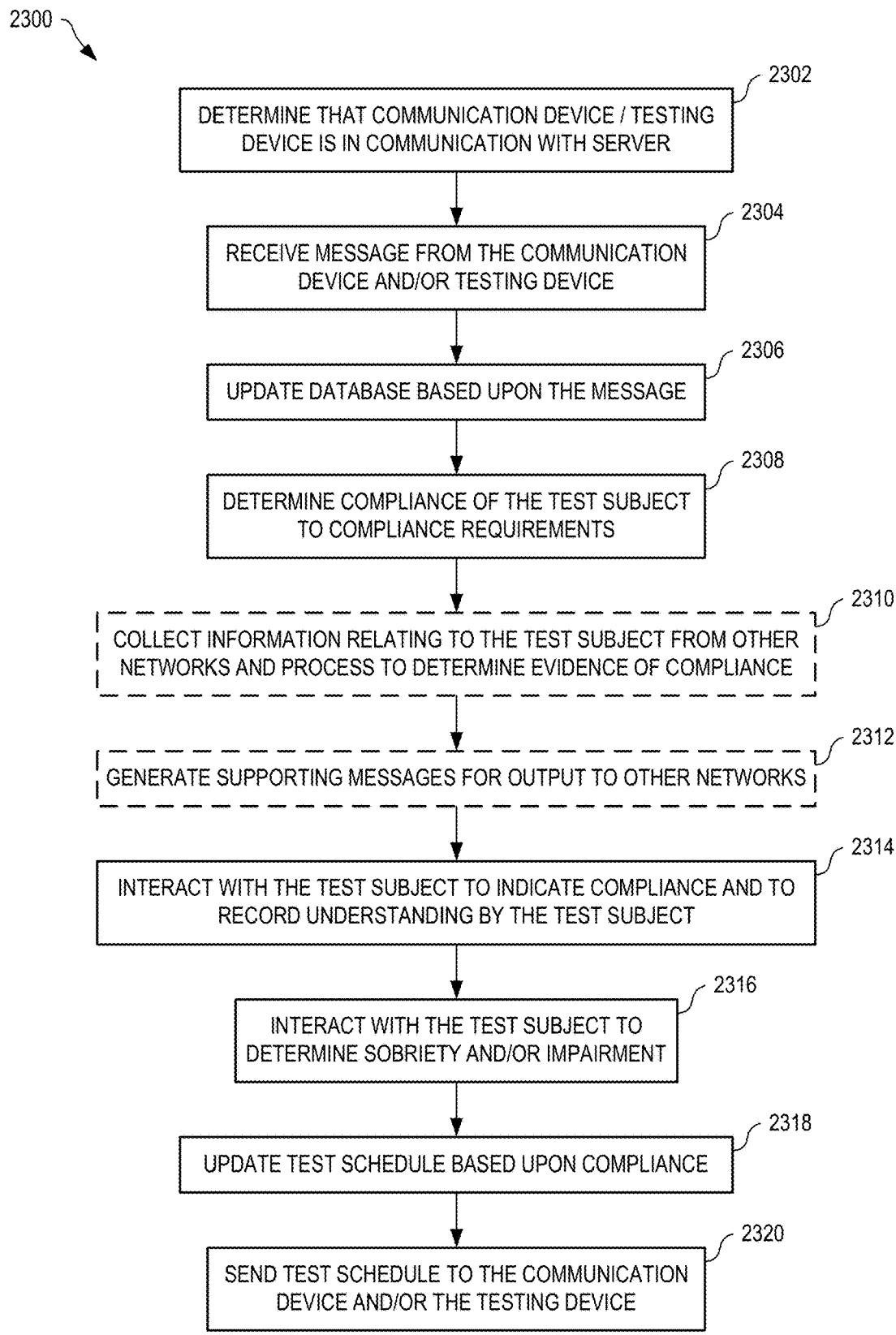
FIG. 23 is a flowchart illustrating one exemplary method for locating and determining substance use, in an embodiment.

FIG. 22 shows a server 2280, similar to server 180 of FIG. 1, showing functionality in further detail. FIG. 23 is a flowchart illustrating one exemplary method 2300 for locating and determining substance use. Method 2300 is implemented within server 2280. FIGS. 22 and 23 are best viewed together with the following description.

Server 2280 is a computer, or network of computers, that includes at least one processor 2202 and memory 2204 storing a database 2282 and a web application 2284. Web application 2284 includes machine readable instructions (i.e., software implementing method 2300) that are executed by processor 2202 to implement functionality of server 2280 as described herein. Web application 2284 may provide a web portal 2299 through which third party device 2231 communicates with web application 2284 and server 2280 via Internet 2201.

Web application 2284 includes a data transfer module 2220 (i.e., a software module) that transfers data between server 2280 and communication device 130, 830, 1630, 1930 and/or testing device 2102 when they are in communication with server 2280. For example, communication device 130, 830, 1630, 1930 and/or testing device 2102 may operate "off-line" from server 2280 when the test subject provides a sample for evaluation, wherein, once data transfer module 2220 determines, in step 2302 of method 2300, that communication device 130, 830, 1630, 1930 and/or testing device 2102 has established communication with server 2280, data transfer module 2220 receives, in step 2304 of method 2300, a message that may contain test results (e.g., location information, BAC value 118/818/1618/1918/2118/2218, image 146/846/1646/1946/2146/2246, image sequence 147/847/1647/1947/2147/2247, and so on) from communication device 130, 830, 1630, 1930 and/or testing device 2102. Data transfer module 2220 stores, in step 2306 of method 2300, information from the received message within database 2282. For example, where the message (e.g., message 160) from communication device 130 includes test results, data transfer module 2220 stores the information as test results 2288 within database 2282.

Upon determining that communication device 130, 830, 1630, 1930 and/or testing device 2102 is connected, data transfer module 2220 may also request and/or receive, in step 2304 of method 2300, location information of communication device 130, 830, 1630, 1930 and/or testing device 2102, and stores, in step 2306 of method 2300, this location information within database 2282. For example, software 144/844/1644 may respond to a location request from server 2280 by utilizing location device 148/848/1648/1948/2148 to determine a current location and send that determined location back to server 2280. This data transfer and location reporting may occur without interaction of the test subject with communication device 130, 830, 1630, 1930 and/or testing device 2102.

Web application 2284 includes a compliance monitor 2224 that, in step 2308 of method 2300, processes test results 2288 against compliance requirements 2285 to determine whether the test subject is complying with defined requirements. For example, compliance requirements 2285 define a maximum substance level and a testing frequency for the test subject. Compliance monitor 2224 may utilize artificial intelligence (e.g., learning algorithms) to analyze compliance requirements 2285, test schedule 2286, and test results 2288 to determine how well the test subject is managing the tests and how best to aid the test subject to comply with future testing.

Compliance monitor 2224 may also collect, in optional step 2310 of method 2300, information of the test subject from other sources (e.g., social networking) to determine evidence of compliance. For example, compliance monitor 2224 may identify, within the information from a social network, behavior of the test subject that supports or contradicts compliance with requirements. Compliance monitor 2224 may also generate and send, in optional step 2312 of method 2300, information to the social network to support, and stimulate compliance by, the test subject. For example, compliance monitor 2224 generates and sends messages to a social network that indicate one or more of success, progress, and future goals that may improve morale of the test subject, and thereby increase likelihood of success of the test subject to meet compliance requirements.

In one embodiment, server 2280 include a support group manager 2229 that provides a web interface (e.g., via web portal 2299) that allows the test subject to communicate with peers. Support group manager 2229 may interact with compliance monitor 2224 and/or notification manager 2226 to post messages to the test subject that provide positive reinforcement for achieving goals related to substance abuse. For example, support group manager 2229 may process test results 2288 and compliance requirements 2285 to automatically generate positive reinforcement messages for the test subject. Peers of the test subject may also post messages of reinforcement to the test subject and offer advice.

In one example of operation, where compliance monitor 2224 determines that the test subject is compliant with compliance requirements 2285, compliance monitor 2224 may generate a reward for the test subject, whereas when compliance monitor 2224 determines that the test subject has not complied with compliance requirements 2285, compliance monitor 2224 may define sanctions for the test subject.

Where compliance monitor 2224 determines that test results 2288 indicate a substance level that is below, but near, a defined substance level threshold at a certain time of day, but is well below the test level threshold at other times of the day, compliance monitor 2224 utilizes intelligence to add one or more "random" tests to test schedule 2286 of the test subject at times corresponding to times when previous test results indicated elevated substance levels. For example, if test results 2288 indicated elevated substance levels in tests performed late Wednesday afternoons, compliance monitor 2224 may add an early Wednesday afternoon test to test schedule 2286. Where compliance monitor 2224 determines that the test subject is fully in compliance with compliance requirements 2285, compliance monitor 2224 may reduce the number of tests within test schedule 2286. Continuing the above example where additional tests were added to test schedule 2286, compliance monitor 2224 may remove these tests after test results 2288 indicate improvement in compliance to compliance requirements 2285. Thus, compliance monitor 2224 may autonomously adjust test schedule 2286 based upon progress of the test subject to meet compliance requirements 2285.

Web application 2284 may also include a notification manager 2226 that generates one or more notifications 2297 that are sent to communication device 2230 used by the test subject. For example, upon receipt of test results 2288 from a scheduled test of the test subject, notification manager 2226 may generate and send notification 2297 to the test subject to indicate receipt of those results. In another example, compliance monitor 2224 may invoke notification manager 2226 to send notification 2297 to communication device 2230 to indicate compliance by the test subject to compliance requirements 2285.

Notification manager 2226 may interact with, in step 2314 of method 2300, the test subject, sending notification 2297 requesting a reply indicating understanding of notification 2297, wherein notification 2297 and any reply from the test subject are stored within communication data 2287 and may be submitted as evidence of test subject awareness of any non-compliance to compliance requirements 2285. Notification manager 2226 may resend notification 2297 when no reply is received from communication device 2230, storing an indication of the lack of reply within communication data 2287 for example. Communication data 2287 thereby contains both interaction and lack of interaction with the test subject.

Notification manager 2226 may also send notification 2297 to a companion app 2235 running on a smart device 2232 of a third party. For example, within server 2280, a victim of domestic abuse by the test subject may be associated with the test subject. For example, database 2282 may store, in association with the test subject, information identifying one or more third parties that has been harmed by the test subject. The victim may (e.g., after download permissions are granted by the Application developer, or its designee such as an agency administrator or supervisor of the test subject) to download and configure a companion app 2235 on smart device 2232 (or enter other contact information such as a text enabled phone number, a voice phone number, an email address, and so on), that enable notification manager 2226 to send notifications thereto.

Smart device 2232 is for example a mobile phone or other such mobile device that may be configured to send location information to web application 2284. Web application 2284 may include a location manager 2228 that receives both (a) location data from software 144 of communication device 130 and (b) location data from companion app 2235 of smart device 2232. For example, software 144 of communication device 130 may be configured to periodically utilize a GPS receiver (e.g., location device 148 of FIG. 1) to determine and send a current location of the test subject to server 2280. Similarly, companion app 2235 may be configured to periodically utilize a location device of smart device 2232 to periodically determine and send the current location to server 2280.

Location manager 2228 uses the received location information from both communication device 130 and smart device 2232 to determine proximity of the test subject to the victim. Location manager 2228 generates and sends notification 2297 indicating proximity of the test subject to the victim when the determined proximity is less than a predefined value. For example, location manager 2228 may send one or more of notification 2297, a text message, an email, and a voice call, to smart device 2232 of the victim, indicating proximity of the test subject thereto. Companion app 2235 may generate an audible alert upon receiving notification 2297 such that the victim becomes aware of the proximity of the test subject. Companion app 2235 may also include a dispatch call button that automatically calls the police dispatch when activated by the victim.

Notification manager 2226 may also interact, in step 2316 of method 2300, with the test subject, via software 144 running on communication device 130, to measure reaction time, response to questions, and other such responses to stimuli, and/or to collect other observations of the test subject, to determine sobriety, impairment of response, cognition, and mental faculty function, and so on, of the test subject. For example, notification manager 2226 may compare responses of the test subject to previously recorded response of the test subject, and/or expected responses, to determine whether the test subject is impaired in any way. Notification manager 2226 may also analyze video of the test subject (e.g., when responding to the questions and stimuli) to detect indications of impairment resulting from substance abuse.

Upon detecting lack of sobriety and/or impairment of the test subject, notification manager 2226 may generate and send notification 2297 to third party device 2231 (i.e., a supervisor of the test subject), may augment test results 2288 with this lack of sobriety and/or impairment information to indicate potential problems regarding compliance of the test subject to compliance requirements 2285. Compliance monitor 2224 and/or notification manager 2226 may initiate an immediate request for testing of the test subject via software 144 and testing device 102, and/or modify test schedule 2286 in step 2318 of method 2300. Compliance monitor 2224 and/or notification manager 2226 then sends, in step 2320 of method 2300, test schedule 2286, or at least part thereof, to communication device 130 and/or testing device 2102.

Web application 2284 includes a report generator 2222 that process test results and other data stored within database 2282 and generates a report on test results 2288. Report generator 2222 is configurable to generate these reports in any required format, such as a bulletin board format that collates information of a particular test subject.

Report generator 2222 may automatically, or on demand, generate a report 2289 summarizing test results 2288 and/or communication data 2287 corresponding to the test subject and send report 2289 to communication device 130 and/or a third-party device 2231. Third party device 2231 is for example one of a computer terminal, a computer, a smart device, and a mobile communication device of a supervisor (e.g., parole officer) of the test subject. In one embodiment, where third party device 2231 is a smart phone, a supervisor application 2233 may be loaded and executed to receive and display information of report 2289 to the user.

Tamper Resistant Mouthpiece

Figure 24:
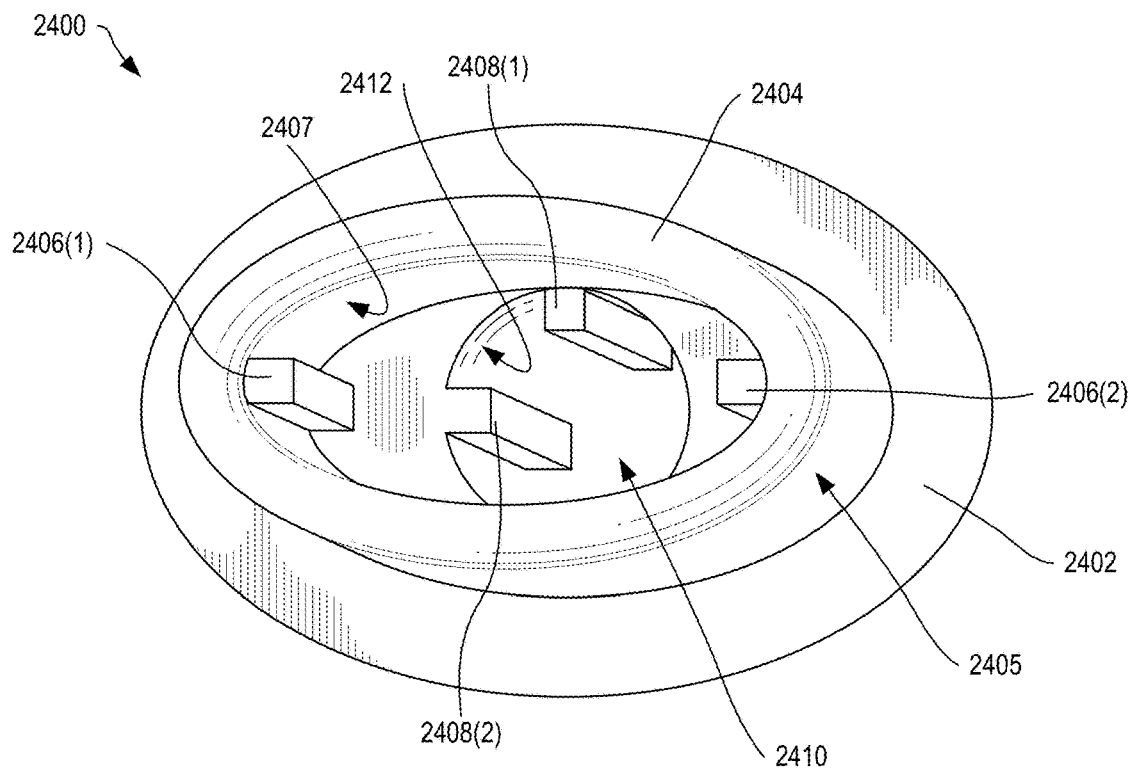
FIG. 24 shows one exemplary mouthpiece configured to hinder or prevent a test subject using a tube to cheat when providing a test sample to a testing device, in an embodiment.

FIG. 24 shows one exemplary mouthpiece 2400 configured to hinder or prevent a test subject using a tube to cheat when providing a test sample to a testing device. Mouthpiece 2400 may represent one or more of distal portion 122 that couples with tube 105 of testing device 102, distal portion 1622 that couples with tube 1605 of testing device 1602, and distal portion 2122 that couples with tube 2105 of testing device 2102.

Mouthpiece 2400 has a flange 2402 that adjoins an oval shaped lip ring 2404 that has an outer surface 2405, onto which the test subject places their lips when blowing into the testing device. An inner surface 2407 of has a substantially oval shape but includes two (or more) first protrusions 2406 that function to break up the smooth shape of inner surface 2407 and thereby make it difficult to utilize a tube within mouthpiece 2400. Mouthpiece 2400 has an inner passage 2410, through flange 2402, which allows a sample to pass from the test subject into the testing device. Inner passage 2410 has a round cross section with a substantially smooth inner surface 2412, except for at least two added protrusions 2408 that function to break up the smooth shape of inner surface 2412 and thereby make it difficult to utilize a tube within mouthpiece 2400.

In particular, protrusions 2406 and 2408 prevent an inserted tube from sealing against inner surfaces 2407 and 2412. By preventing the tube from sealing within mouthpiece 2400, a test subject cannot have someone else provide a test sample into the testing device without such miss-use being detected within images captured by the communication device. Further, the testing device includes a flow meter and/or pressure sensor that registers the test sample being provided based upon one to both of flow rate and pressure. Without a tube sealing within mouthpiece 2400, sufficient pressure and/or flow rate cannot be achieved.

Figure 25:
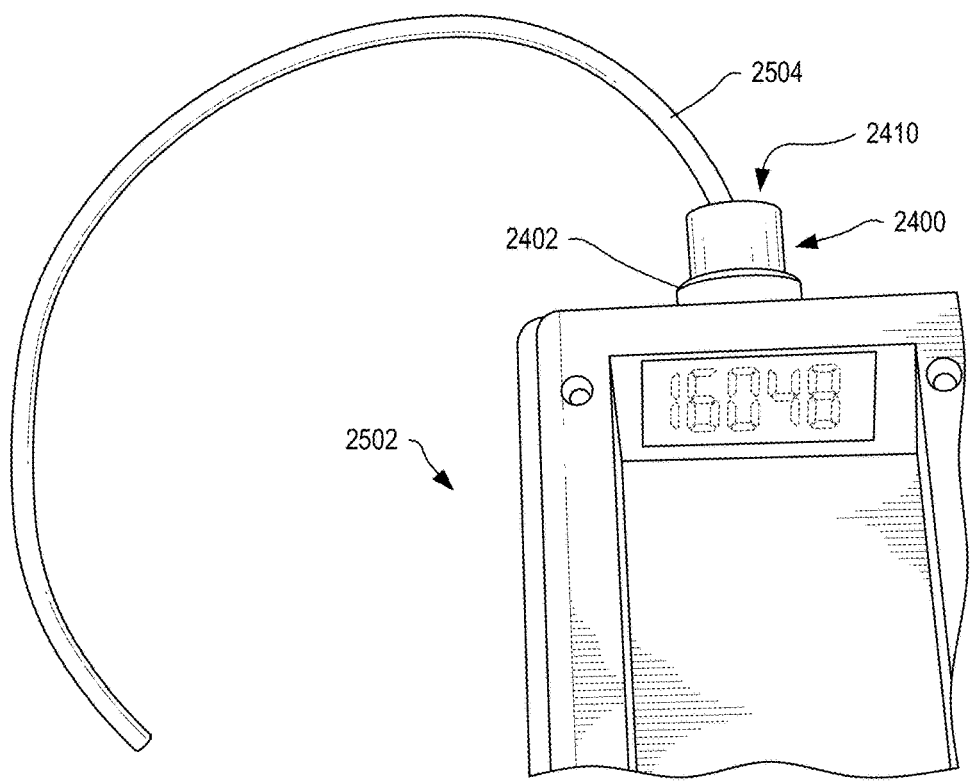
FIG. 25 shows the mouthpiece of FIG. 24 preventing a tube from providing a sample to a testing device.

FIG. 25 shows mouthpiece 2400 of FIG. 24 preventing a tube 2504 from coupling to provide a sample to testing device 2502. Due to protrusions 2406 and 2408 within mouthpiece 2400, to fit within inner passage 2410, tube 2504 is necessarily small and thus cannot seal within inner surface 2412 due to the irregular shape formed by the protrusions on inner surface 2412.

Figure 26:
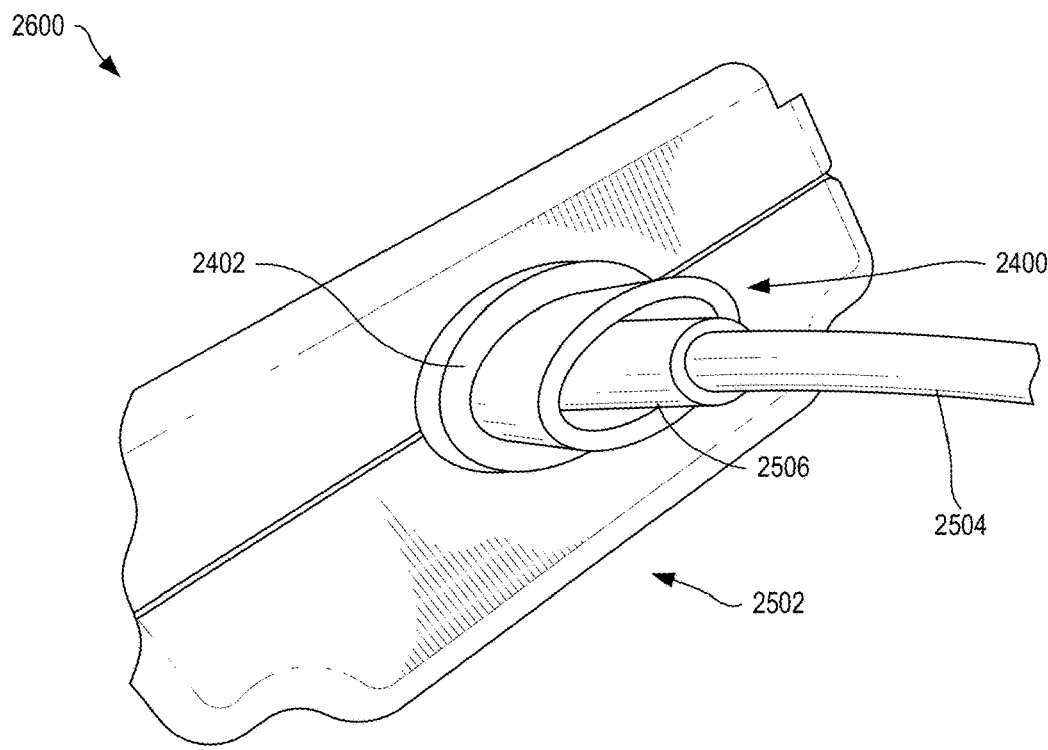
FIGS. 26 and 27 are schematics illustrating the mouthpiece of FIG. 24 preventing the use of a sealing product with the tube to provide a test sample to the testing device.
Figure 27:
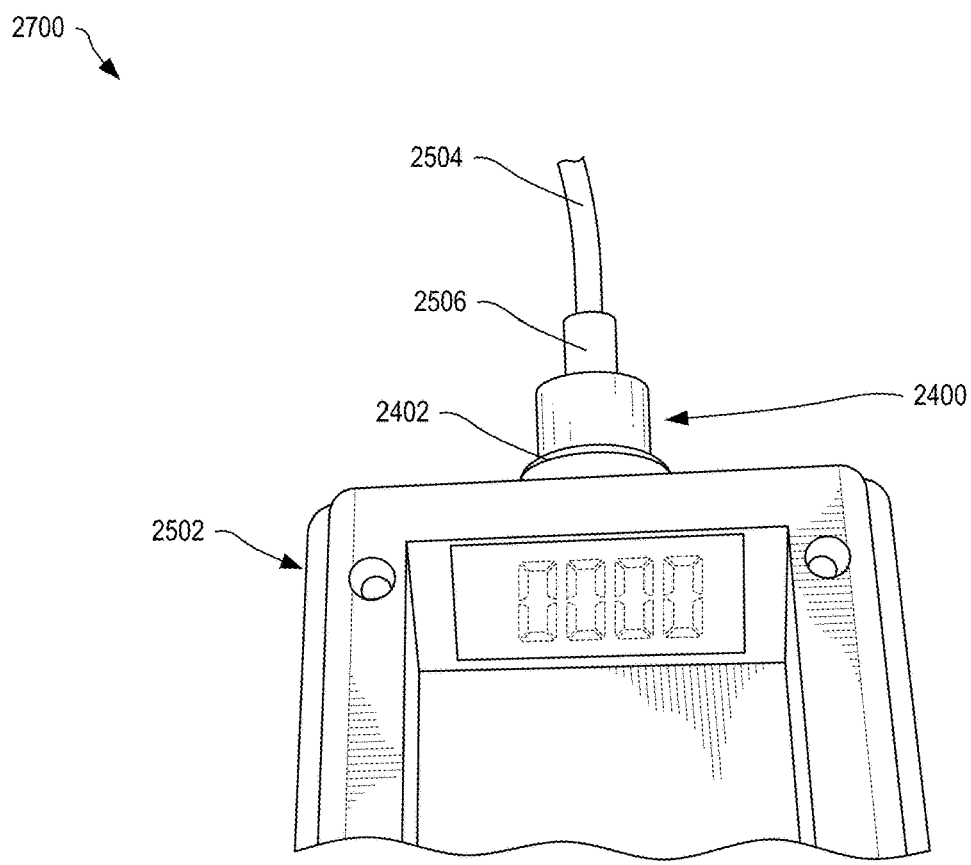

FIGS. 26 and 27 are schematics illustrating mouthpiece 2400 of FIG. 24 preventing the use of a sealing product 2506 with the tube to provide a test sample to testing device 2502. Tube 2504 wrapped in a sealing product 2506 (e.g., thread sealing tape) is inserted into mouthpiece 2400. Although this may provide sufficient sealing for a test sample to be provided through tube 2504, this attempt is difficult to implement and may be easily detected within images captured of the test subject providing the test sample.

Combination of Features

Features described above as well as those claimed below may be combined in various ways without departing from the scope hereof. The following examples illustrate possible, non-limiting combinations the present invention has been described above, it should be clear that many changes and modifications may be made to the process and product without departing from the spirit and scope of this invention:

(A) A software product includes stored instructions, stored on non-transitory computer-readable media, that, when executed by a digital processor of a communication device, perform steps for controlling a testing device separate and distinct from the communication device to determine a substance level in a test sample provided to the testing device by a test subject. The stored instructions include instructions for: generating, from the communication device, a prompt for the test subject to provide the test sample to the testing device; capturing, using a camera of the communication device, a sequence of images that include the test subject providing the test sample to the testing device, the camera being positioned by a physical positioning mechanism of the testing device to include a portion of a face of the test subject providing the test sample and a display of the testing device; detecting a position of the face within a field of view of the camera; instructing the test subject to reposition the camera when the position indicates that the image may be unsuitable for authenticating an identity of the test subject; receiving, within the communication device and from the testing device, a value indicative of the substance level detected within the test sample; determining a validity indicator defining validity of the value indicative of the substance level; determining, within the communication device, a current location; and sending, from the communication device, the value indicative of the substance level, the validity indicator, and the current location to a remote server.

(B) The software product denoted as (A), further including stored instructions for: determining a direction the face is pointing relative to the camera; and instructing the test subject to reposition the camera when the direction indicates that the image may be unsuitable for authenticating the identity of the test subject.

(C) In either of the software products denoted as (A) and (B), further comprising stored instructions for: determining a distance of the face from the camera; and instructing the test subject to reposition the camera when the distance of the face from the camera indicates that the image may be unsuitable for authenticating the identity of the test subject.

(D) In any of the software products denoted as (A)-(C), further comprising stored instructions for: determining an angle of head tilt relative to the camera; and instructing the test subject to reposition the camera when the angle of head tilt relative to the camera indicates that the image may be unsuitable for authenticating the identity of the test subject.

(E) In any of the software products denoted as (A)-(D), further comprising stored instructions for: detecting presence of additional faces within the field of view; and instructing the test subject to reposition the camera when the presence of additional faces within the field of view indicates that the image may be unsuitable for authenticating the identity of the test subject.

(F) In any of the software products denoted as (A)-(E), further comprising stored instructions for: determining a lighting level/quality within the field of view; and instructing the test subject to reposition the camera when the lighting level/quality within the field of view indicates that the image may be unsuitable for authenticating the identity of the test subject.

(G) In any of the software products denoted as (A)-(F), further comprising stored instructions for determining a liveness probability of the portion of the face in the sequence of images, the validity indicator being based on the liveness probability.

(H) In any of the software products denoted as (A)-(G), further comprising stored instructions for generating an ID probability indicative of at least one image of the sequence of images matching an ID image, the validity indicator being based upon the ID probability.

(I) A method for detecting fraudulent use of a testing device that measures a substance level within a test sample provided by a test subject, including: capturing, using a camera physically positioned to have a field of view of at least part of a face of the test subject providing the test sample, an image sequence of the test subject providing the test sample; detecting a position of the face within a field of view of the camera; instructing the test subject to reposition the camera when the position indicates that the image may be unsuitable for authenticating an identity of the test subject; determining, from detected differences between images of the image sequence, a liveness probability for the portion of the face in the image sequence; and sending the liveness probability together with the level of the substance within the test sample to a remote server.

(J) The method denoted as (I), further including: determining a direction the face is pointing relative to the camera; and instructing the test subject to reposition the camera when the direction indicates that the image may be unsuitable for authenticating the identity of the test subject.

(K) Either of the methods denoted as (I) and (J), further including: determining a distance of the face from the camera; and instructing the test subject to reposition the camera when the distance of the face from the camera indicates that the image may be unsuitable for authenticating the identity of the test subject.

(L) Any of the methods denoted as (I)-(K), further including: determining an angle of head tilt relative to the camera; and instructing the test subject to reposition the camera when the angle of head tilt relative to the camera indicates that the image may be unsuitable for authenticating the identity of the test subject.

(M) Any of the methods denoted as (I)-(L), further including: detecting presence of additional faces within the field of view; and instructing the test subject to reposition the camera when the presence of additional faces within the field of view indicates that the image may be unsuitable for authenticating the identity of the test subject.

(N) Any of the methods denoted as (I)-(M), further including: determining a lighting level/quality within the field of view; and instructing the test subject to reposition the camera when the lighting level/quality within the field of view indicates that the image may be unsuitable for authenticating the identity of the test subject.

(O) Any of the methods denoted as (I)-(N), further including: detecting eye movement of the test subject within images of the image sequence; and counting a first number of blinks made by the test subject while providing the test sample. The liveness probability being based upon the first number.

(P) Any of the methods denoted as (I)-(O), further including: counting a second number of blinks made by the test subject prior to providing the test sample; the liveness probability being based upon the first number and the second number.

(Q) Any of the methods denoted as (I)-(P), further including: counting a second number of blinks made by the test subject after providing the test sample; the liveness probability being based upon the first number and the second number.

(R) A testing device for detecting a substance level within a test sample provided by a test subject, including: at least one sensor for detecting the substance level within the test sample; a camera positioned to have a field of view that includes the test subject providing the test sample to the testing device; a location device for determining a current location of the testing device; a processor communicatively coupled with the at least one sensor and the camera; and a memory communicatively coupled with the processor and storing machine readable instructions that when executed by the processor perform the steps of: detecting a position of a face within the field of view of the camera; instructing the test subject to reposition the testing device when the position indicates that images captured by the camera may be unsuitable for authenticating an identity of the test subject; capturing, using the camera, a sequence of images that include the test subject providing the test sample to the testing device; determining, based upon the at least one sensor, a value indicative of the substance level detected within the test sample; determining, using the location device, a current location of the testing device; determining, based upon the sequence of images, a validity indicator indicative of validity of one or both of an identity of the test subject and a liveness of the test subject; and sending, to a remote server, the value indicative of the substance level, the current location, and the validity indicator.

(S) The testing device denoted as (R), the memory further storing machine readable instructions that when executed by the processor perform the steps of: determining a distance of the face from the camera; and instructing the test subject to reposition the camera when the distance indicates that the image may be unsuitable for authenticating the identity of the test subject.

(T) In either of the testing devices denoted as (R) and (S), the memory further storing machine readable instructions that when executed by the processor perform the steps of: determining an angle of head tilt relative to the camera; and instructing the test subject to reposition the camera when the angle of head tilt relative to the camera indicates that the image may be unsuitable for authenticating the identity of the test subject.

(U) In any of the testing devices denoted as (R) (T), the memory further storing machine readable instructions that when executed by the processor perform the steps of: detecting presence of additional faces within the field of view; and instructing the test subject to reposition the camera when the presence of additional faces within the field of view indicates that the image may be unsuitable for authenticating the identity of the test subject.

(V) In any of the testing devices denoted as (R) (U), the memory further storing machine readable instructions that when executed by the processor perform the steps of: determining a lighting level/quality within the field of view; and instructing the test subject to reposition the camera when the lighting level/quality within the field of view indicates that the image may be unsuitable for authenticating the identity of the test subject.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A software product comprising: stored instructions, stored on non-transitory computer-readable media, that, when executed by a digital processor of a communication device, perform steps for controlling a testing device separate and distinct from the communication device to determine a substance level in a test sample provided to the testing device by a test subject, the stored instructions comprising instructions for:

generating, from the communication device, a prompt for the test subject to provide the test sample to the testing device;

capturing, using a camera of the communication device, a sequence of images that include the test subject providing the test sample to the testing device, the camera being positioned by a physical positioning mechanism of the testing device to include a portion of a face of the test subject providing the test sample and a display of the testing device;

detecting a position of the face within a field of view of the camera;

instructing the test subject to reposition the camera when the position indicates that the image may be unsuitable for authenticating an identity of the test subject;

receiving, within the communication device and from the testing device, a value indicative of the substance level detected within the test sample;

determining a validity indicator defining validity of the value indicative of the substance level, the validity indicator including a liveness indication determinable by:

detecting eye movement of the test subject within images of the image sequence; and counting a first number of blinks made by the test subject while providing the test sample;

the liveness indication being based upon the first number;

determining, within the communication device, a current location; and sending, from the communication device, the value indicative of the substance level, the validity indicator, and the current location to a remote server.

2. The software product of claim 1, further comprising stored instructions for:

determining a direction the face is pointing relative to the camera; and instructing the test subject to reposition the camera when the direction indicates that the image may be unsuitable for authenticating the identity of the test subject.

3. The software product of claim 1, further comprising stored instructions for:

determining a distance of the face from the camera; and instructing the test subject to reposition the camera when the distance of the face from the camera indicates that the image may be unsuitable for authenticating the identity of the test subject.

4. The software product of claim 1, further comprising stored instructions for:

determining an angle of head tilt relative to the camera; and instructing the test subject to reposition the camera when the angle of head tilt relative to the camera indicates that the image may be unsuitable for authenticating the identity of the test subject.

5. The software product of claim 1, further comprising the stored instructions for:

detecting presence of additional faces within the field of view; and instructing the test subject to reposition the camera when the presence of additional faces within the field of view indicates that the image may be unsuitable for authenticating the identity of the test subject.

6. The software product of claim 1, further comprising stored instructions for:

determining a lighting level/quality within the field of view; and instructing the test subject to reposition the camera when the lighting level/quality within the field of view indicates that the image may be unsuitable for authenticating the identity of the test subject.

7. The software product of claim 1, further comprising stored instructions for generating an ID probability indicative of at least one image of the sequence of images matching an ID image, the validity indicator being based upon the ID probability.

8. A method for detecting fraudulent use of a testing device that measures a substance level within a test sample provided by a test subject, comprising:

capturing, using a camera physically positioned to have a field of view of at least part of a face of the test subject providing the test sample, an image sequence of the test subject providing the test sample;

detecting a position of the face within a field of view of the camera;

instructing the test subject to reposition the camera when the position indicates that the image may be unsuitable for authenticating an identity of the test subject;

determining, from detected differences between images of the image sequence, a liveness probability for the portion of the face in the image sequence by:

detecting eye movement of the test subject within images of the image sequence; and counting a first number of blinks made by the test subject while providing the test sample;

the liveness probability being based upon the first number; and sending the liveness probability together with the level of the substance within the test sample to a remote server.

9. The method of claim 8, further comprising:

determining a direction the face is pointing relative to the camera; and instructing the test subject to reposition the camera when the direction indicates that the image may be unsuitable for authenticating the identity of the test subject.

10. The method of claim 8, further comprising:

determining a distance of the face from the camera; and instructing the test subject to reposition the camera when the distance of the face from the camera indicates that the image may be unsuitable for authenticating the identity of the test subject.

11. The method of claim 8, further comprising:

determining an angle of head tilt relative to the camera; and instructing the test subject to reposition the camera when the angle of head tilt relative to the camera indicates that the image may be unsuitable for authenticating the identity of the test subject.

12. The method of claim 8, further comprising:

detecting presence of additional faces within the field of view; and instructing the test subject to reposition the camera when the presence of additional faces within the field of view indicates that the image may be unsuitable for authenticating the identity of the test subject.

13. The method of claim 8, further comprising:

determining a lighting level/quality within the field of view; and instructing the test subject to reposition the camera when the lighting level/quality within the field of view indicates that the image may be unsuitable for authenticating the identity of the test subject.

14. The method of claim 8, further comprising:

counting a second number of blinks made by the test subject prior to providing the test sample;

the liveness probability being based upon the first number and the second number.

15. The method of claim 8, further comprising:

counting a second number of blinks made by the test subject after providing the test sample;

the liveness probability being based upon the first number and the second number.

16. A testing device for detecting a substance level within a test sample provided by a test subject, comprising:

at least one sensor for detecting the substance level within the test sample;

a camera positioned to have a field of view that includes the test subject providing the test sample to the testing device;

a location device for determining a current location of the testing device;

a processor communicatively coupled with the at least one sensor and the camera; and a memory communicatively coupled with the processor and storing machine readable instructions that when executed by the processor perform the steps of:

detecting a position of a face within the field of view of the camera;

instructing the test subject to reposition the testing device when the position indicates that images captured by the camera may be unsuitable for authenticating an identity of the test subject;

capturing, using the camera, a sequence of images that include the test subject providing the test sample to the testing device;

determining, based upon the at least one sensor, a value indicative of the substance level detected within the test sample;

determining, using the location device, a current location of the testing device;

determining, based upon the sequence of images, a validity indicator indicative of validity of a liveness probability of the test subject by:

detecting eye movement of the test subject within images of the sequence of images; and counting a first number of blinks made by the test subject while providing the test sample;

the liveness probability being based upon the first number; and sending, to a remote server, the value indicative of the substance level, the current location, and the validity indicator.

17. The testing device of claim 16, the memory further storing machine readable instructions that when executed by the processor perform the steps of:

determining a distance of the face from the camera; and instructing the test subject to reposition the camera when the distance indicates that the image may be unsuitable for authenticating the identity of the test subject.

18. The testing device of claim 16, the memory further storing machine readable instructions that when executed by the processor perform the steps of:

determining an angle of head tilt relative to the camera; and instructing the test subject to reposition the camera when the angle of head tilt relative to the camera indicates that the image may be unsuitable for authenticating the identity of the test subject.

19. The testing device of claim 16, the memory further storing machine readable instructions that when executed by the processor perform the steps of:

detecting presence of additional faces within the field of view; and instructing the test subject to reposition the camera when the presence of additional faces within the field of view indicates that the image may be unsuitable for authenticating the identity of the test subject.

20. The testing device of claim 16, the memory further storing machine readable instructions that when executed by the processor perform the steps of:

determining a lighting level/quality within the field of view; and instructing the test subject to reposition the camera when the lighting level/quality within the field of view indicates that the image may be unsuitable for authenticating the identity of the test subject.

* * * * *